United States Patent
Takalo

(10) Patent No.: US 10,365,286 B2
(45) Date of Patent: Jul. 30, 2019

(54) CHROMOPHORIC STRUCTURES FOR LANTHANIDE CHELATES

(71) Applicant: RADIOMETER TURKU OY, Turku (FI)

(72) Inventor: Harri Takalo, Turku (FI)

(73) Assignee: Radiometer Turku Oy, Turku (FI)

( * ) Notice: Subject to any disclaimer, the term of this patent is extended or adjusted under 35 U.S.C. 154(b) by 158 days.

(21) Appl. No.: 15/308,458

(22) PCT Filed: Apr. 24, 2015

(86) PCT No.: PCT/EP2015/058970
§ 371 (c)(1),
(2) Date: Nov. 2, 2016

(87) PCT Pub. No.: WO2015/165826
PCT Pub. Date: Nov. 5, 2015

(65) Prior Publication Data
US 2017/0089913 A1    Mar. 30, 2017

(30) Foreign Application Priority Data

May 2, 2014 (DK) ................................ 2014 00242

(51) Int. Cl.
*G01N 33/58* (2006.01)
*C09K 11/06* (2006.01)
*G01N 21/64* (2006.01)

(52) U.S. Cl.
CPC ............ *G01N 33/582* (2013.01); *C09K 11/06* (2013.01); *C09K 2211/1011* (2013.01);
(Continued)

(58) Field of Classification Search
CPC ............ C09K 11/06; C09K 2211/1096; C09K 2211/1011; C09K 2211/1029;
(Continued)

(56) References Cited

U.S. PATENT DOCUMENTS

2010/0314994 A1    12/2010   Che et al.
2012/0100628 A1     4/2012   Sun et al.
(Continued)

FOREIGN PATENT DOCUMENTS

JP      2012-530077         11/2012
WO   WO 2013/026790 A1      2/2013
WO   WO 2013/092992 A1      6/2013

OTHER PUBLICATIONS

Picot et al. Two-photon antenna effect induced in octupolar europium complexes. Inorg. Chem. 2007, vol. 46, pp. 2659-2665. (Year: 2007).*

Picot, Alexandre et al., "Two-Photon Antenna Effect Induced in Octupolar Europium Complexes," Inorganic Chemistry, vol. 46, No. 7, pp. 2659-2665 (2007).
English language abstract of JP 2012-530077, Nov. 19, 2012.
(Continued)

*Primary Examiner* — Shafiqul Haq
(74) *Attorney, Agent, or Firm* — Finnegan, Henderson, Farabow, Garrett & Dunner, LLP

(57) ABSTRACT

The present application discloses novel lanthanide chelate designs (Formula (I) and Formula (III)) having fluorenyl-, fluorenylethynyl-, 9H-carbazolyl-, 9H-carbozolylethynyl-, dibenzothiophenyl-, dibenzothiophenylethynyl-, dibenzofuranyl or dibenzofuranylethynyl pyridine chromophores around an emitting lanthanide ion, e.g. an europium(III) ion. The three-membered ring chromophores exhibit high molar absorptivity and luminescence with lanthanide ions. The application also discloses a detectable molecule comprising a biospecific binding reactant useful in bioaffinity based binding assay, luminescent lanthanide chelating ligands, as well as a solid support conjugated with the chelates.

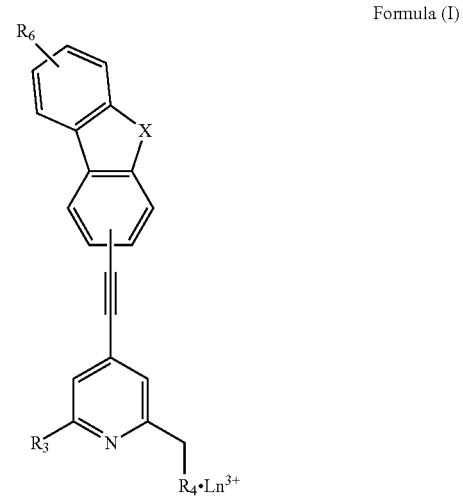

Formula (I)

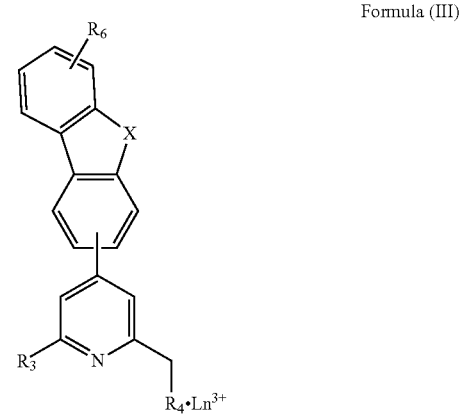

Formula (III)

10 Claims, No Drawings

(52) U.S. Cl.
CPC ........... *C09K 2211/1029* (2013.01); *C09K 2211/1044* (2013.01); *C09K 2211/1048* (2013.01); *C09K 2211/1059* (2013.01); *C09K 2211/1074* (2013.01); *C09K 2211/1088* (2013.01); *C09K 2211/1092* (2013.01); *C09K 2211/1096* (2013.01); *C09K 2211/182* (2013.01); *G01N 21/6408* (2013.01); *G01N 21/6428* (2013.01); *G01N 2458/40* (2013.01)

(58) Field of Classification Search
CPC .... C09K 2211/1088; C09K 2211/1092; C09K 2211/182; C09K 2211/1074; C09K 2211/1059; C09K 2211/1048; C09K 2211/1044; G01N 33/582; G01N 21/6428; G01N 2458/40; G01N 21/6408
See application file for complete search history.

(56) References Cited

U.S. PATENT DOCUMENTS

2013/0183771 A1   7/2013   Meltola et al.
2013/0210165 A1   8/2013   Meltola et al.

OTHER PUBLICATIONS

International Search Report for International Application No. PCT/EP2015/058970, dated Jul. 23, 2015.

Written Opinion of the International Search Authority for International Application No. PCT/EP2015/058970.

Zhou, Yong-Hui et al., "Synthesis and Photoluminescence Properties of Europium(III) Complexes Based on 2, 2':6', 2"-Terpyridine Derivatives with Hole Transport Moieties," Chinese Journal of Inorganic Chemistry, vol. 29, No. 4, pp. 201-708 (2013).

Treibs, von Wilhelm et al., "Isoazalene, I. 4-Aryl-3-carboxy-pyridine als Ausgangssubstanzen für N-Methyl-1.2-benzisoazalene," Justus Liebigs Annalen der Chemie, vol. 652, Issue 1, pp. 192-203 (1962).

Hovinen, J., et al., "Bioconjugation with Stable Luminescent Lanthanide(III) Chelates Comprising Pyridine Subunits," *Bioconjugate Chem.*, 2009, 20, pp. 404-421.

* cited by examiner

CHROMOPHORIC STRUCTURES FOR LANTHANIDE CHELATES

This application is a national stage filing under 35 U.S.C. § 371 of International Application No. PCT/EP2015/058970, filed on Apr. 24, 2015, which claims priority of Danish Patent Application No. PA2014/00242, filed May 2, 2014. The contents of both applications are each incorporated herein by reference.

The invention relates to a novel lanthanide chelate design having fluorenyl-, fluorenylethynyl, 9H-carbazolyl-, 9H-carbozolylethynyl-, dibenzothiophenyl-, dibenzothiophenylethynyl-, dibenzofuranyl or dibenzofuranylethynyl pyridine chromophores around an emitting lanthanide ion. The three-membered ring chromophores have high molar absorptivity and luminescence with lanthanide ions. The invention also relates to chelates to be attached to a biospecific reactant and their use in various assays.

BACKGROUND OF THE INVENTION

For Time-resolved fluorometry (TRF) applications an optimal luminescent lanthanide chelate has to fulfill several requirements 1) it has to be photochemical stable both in ground and excited state, 2) it has to be kinetically and chemically stable, 3) the excitation wavelength has to be as high as possible, preferable over 300 nm, 4) it has to have efficient cation emission i.e. high luminescence yield i.e. brightness (excitation coefficient x quantum yield, $\varepsilon\varphi$), 5) the luminescence decay time has to be long, 6) the chelate has to have good water solubility, 6) for labeling it should have a reactive group to allow covalent attachment to a biospecific binding reactant, and 7) the affinity and nonspecific binding properties of the labeled biomolecules have to be retained.

Generally, the excited energy transfers from a ligand to a specific lanthanide ion through the ligand's triplet state. However, if the ligand presents a low-energy charge-transfer (CT) state, the sensitization can occur directly from the relaxed CT state without any participation of the triplet (Andraud, C., Maury, O., Eur. J. Inorg. Chem 2009, 4357). Also, excitation directly through the ligand's singlet state has been demonstrated.

Since the publication of label chelates which contain 1-3 separate 4-(phenylethynyl)pyridines (U.S. Pat. No. 4,920, 195; Takalo, H., et al., 1996, Helv. Chim.Acta., 79, 789) and 4-phenylpyridines (EP 0195413; WO 87/07955), the designed ligand structures have been applied in many patents, patent applications and publications. One generally used method to improve luminescence intensity is to enhance chelate's molar absorptivity by having several independent chromophoric moieties i.e. 4-(phenylethynyl) pyridines and 4-phenylpyridines combined in structure designs, which offer high stabilities and luminescence quantum yields (see e.g. US 2013/210165 A1 and US 2013/183771 A1).

It is generally known that the luminescence intensity is improved also by increasing chromophore's molar absorptivity together with quantum yield. The molar absorptivity can be enhanced by increasing the it-electron conjugation of the aromatic chromophore. At the same time, the excitation wavelength is normally red shifted. However, the increased conjugation normally decreases the triplet state and/or CT's energy level and decreased quantum yield and decay time are observed. For this reason, in practical bio-label applications the molar absorptivities of the used single chromophores in the lanthanide chelates are in best cases few tens of thousands. Moreover, the increased aromatic conjugation of chromophore decreases the chelate's water solubility, increases unspecific binding properties and formation of aggregates of lanthanide labels as well as the labeled biomolecule. Regarding 4-phenylethynylpyridine and 4-phenylpyridine based chelate labels the higher aromatic conjugation chromophore candidates such as 4-[4-(phenylethynyl)phenylethynyl]pyridine, 4-(4-phenyl-1,3-butadiyne-1,4-diyl)pyridine, 4-(biphenyl-ethynyl)pyridine, 4-biphenylpyridine, 4-(benzoylphenylethynyl)pyridine, naphthylethynylpyridine and 4-(2-fluorenylethynyl)-pyridine (see e.g. Takalo, H., at al. J. Alloys and Compounds, 225(1995)511; D'Aleo, A., et al. Inorg Chem., 47(2008) 10269; Picot A., et al. lnorg. Chem. 46(2007)2659) have been published. However, the disclosed chelate designs have not shown any significant improved luminescence intensity compared to the parent basic chelates. For example, Picot et al. describes that for the europium chelate of 4-(2-(7-hexyloxy-9,9'-dihexylfluorenyl)ethynyl)-2,6-bis(diethylcarbamoyl)pyridine.[OTf]$_3$ no significant emission is observed at room temperature" and that "[it is likely that either the CT or the triplet state of the pyridine ligand] at room temperature lies too low in energy to sensitize the europium ion".

A well-known challenge with chelates and ligands having many chromophores is to find out a suitable structure design, which offers high water solubility and at the same time being inert towards any possible bioprocesses. It is known, that the addition of chromophores decreases the solubility of ligands and chelates in water, increases the formation of bio-specific binding reactant aggregates during the labeling process and non-specific binding properties of labeled biomolecules. Aggregates will produce purification problems and reduced yield of labeled material. Moreover, increased non-specific binding of labeled biomolecule will enhance back-ground luminescence of biospecific assays and thus reduces assay sensitivity.

Contrary to earlier published structures the new chromophoric lanthanide chelate designs have shown improved luminescence intensities i.e. brightness as well as high excitation wavelengths. Those chromophores have shown surprisingly high molar absorptivities the main reason behind the observed luminescence intensities.

SUMMARY OF THE INVENTION

A first aspect of the invention relates to a luminescent lanthanide chelate comprising one or more chromophoric moieties of the formula (I) or of the formula (III)

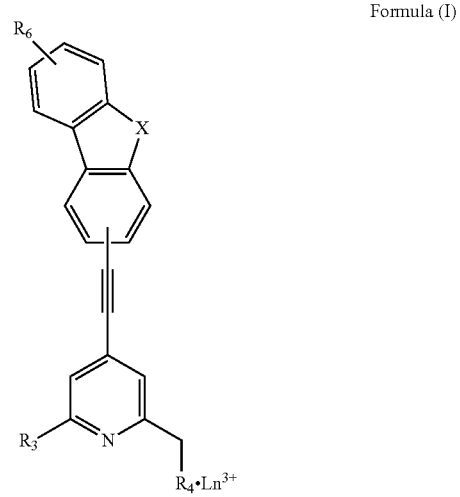

Formula (I)

Formula (III)

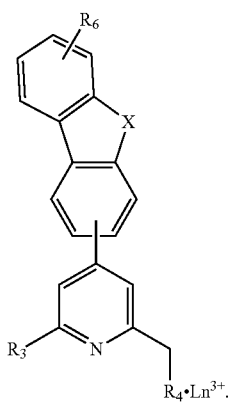

A second aspect of the invention relates to a detectable molecule comprising a biospecific binding reactant conjugated to a luminescent lanthanide chelate comprising one or more moieties of the formula (I) or (III) as defined herein.

A third aspect of the invention relates to a luminescent lanthanide chelating ligand comprising one or more chromophoric moieties of the formula (II) or of the formula (IV)

Formula (II)

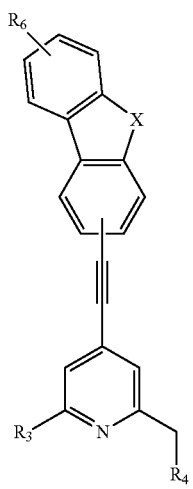

Formula (IV)

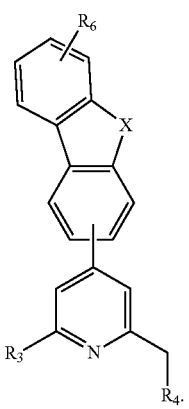

A fourth aspect of the invention relates to a method of carrying out a biospecific binding assay, said method comprising the steps of: a) forming a biocomplex between an analyte and a biospecific binding reactant labelled with a luminescent lanthanide chelate as defined herein; b) exciting said biocomplex with radiation having an excitation wavelength, thereby forming an excited biocomplex; and c) detecting emission radiation emitted from said excited biocomplex.

A fifth aspect of the invention relates to the use of a detectable molecule as defined herein in a specific bioaffinity based binding assay utilizing time-resolved fluorometric determination of a specific luminescence e.g. based on one or two photon excitation.

A sixth aspect of the invention relates to a solid support material conjugated with a luminescent lanthanide chelate as defined herein.

The structural modification according to the present invention has been employed in several different chelate structures (see the Examples). For these chelates where the modification was introduced, significant increase of molar coefficient ($\varepsilon$, i.e. absorptivity) compared to chelates having a conventional substitution pattern. Surprisingly, absorptivity even over 100 000 $cm^{-1}M^{-1}$/chromophore has been obtained with the new lanthanide labels where the absorptivity typically lies from 5 000 to 30 000 $cm^{-1}M^{-1}$. Although the high conjugation of aromatic structures, the observed triplet states have been high enough to offer at least moderate quantum yields ($\Phi$). As a consequence of these features, the observed overall luminescence yields ($\varepsilon\Phi$, i.e. brightness) are significant higher compared to the other comparable label designs. Moreover, excitation wavelengths ($\lambda_{exc}$) even over 340 nm have been obtained, which offers excitation by low-priced LED based instrumentation.

DETAILED DISCLOSURE OF THE INVENTION

The aim of the present invention is to provide means to obtain improved lanthanide chelate labels to be used in specific bioaffinity based binding assays, such as immunoassays (both homogeneous and heterogeneous), nucleic acid hybridization assays, receptor-binding assays, enzymatic assays, immunocytochemical, immunohistochemical assays and cell based assays utilizing fluorometric or time-resolved fluorometric determination of specific luminescence. Chelates of the present invention provide means to obtain improved bioaffinity based binding assays related to e.g. assay sensitivity, and background, even at wavelengths above 340 nm.

Luminescent Lanthanide Chelate

One aspect of the present invention relates to a luminescent lanthanide chelate comprising one or more chromophoric moieties of the formula (I) or of the formula (III)

Formula (I)

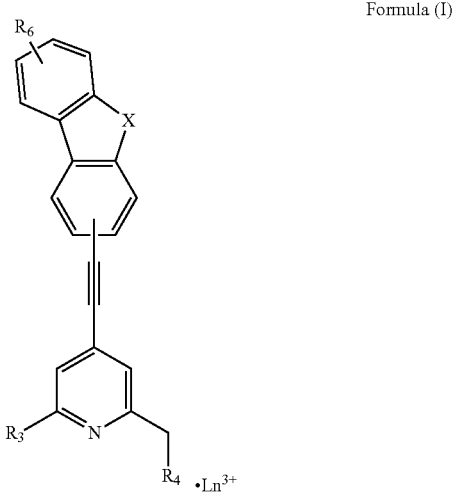

-continued

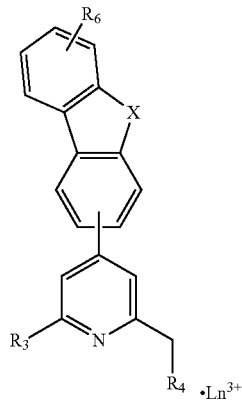

Formula (III)

wherein X is selected from —S—, —O—, —CR$_1$R$_2$—, >C=O, and >C=N—O—R$_1$ (an oxime of >C(=O));
wherein R$_1$ and R$_2$ each independently are selected from hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3$H$^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$EtR$_5$, —(CH$_2$)$_{1-6}$N(R$_5$)$_2$, —(CH$_2$)$_{1-6}$N$^+$(CH$_3$)$_2$R$_5$, —(CH$_2$)$_{1-6}$OH, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is selected from hydrogen, C$_{1-12}$-alkyl (in particular C$_{1-6}$-alkyl), —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$N$^+$(CH$_3$)$_2$(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, a hydrophilic group (optionally including a spacer), a reactive group (optionally including a spacer), an oligopeptide, a polypeptide and a nucleotide;

R$_3$ and R$_4$ each represent a bond between the chromophoric moiety and other moieties of the chelate, R$_6$ is selected from hydrogen —Cl, —Br, —F, —I, —CH$_3$, —(CH$_2$)$_{1-6}$OH, —(CH2)$_{1-6}$OCH$_3$—CF$_3$, —CN, —NO$_2$, —OH, —OCH$_3$, —(CH$_2$)$_{1-6}$OH, —O(CH$_2$)$_{1-6}$OCH$_2$, —O(CH$_2$)$_{1-6}$COOH, —O(CH$_2$)$_{1-6}$COO$^-$, —SCH$_3$, —S(CH$_2$)$_{1-6}$OH, —S(CH$_2$)$_{1-6}$OCH$_2$, —S(CH$_2$)$_{1-6}$COOH, —S(CH$_2$)$_{1-6}$COO$^-$, —CONH$_2$, —CONHCH$_3$, —CON(CH$_3$)$_2$, —CONH(CH$_2$)$_{1-6}$OH, —CONHCH(CH$_2$OH)$_2$, —CONHC(CH$_2$OH)$_3$, —NHCOCH$_3$, —NHCO(CH$_2$)$_{1-6}$OH, —NHCO(CH$_2$)$_{1-6}$COOH, —NHCO(CH$_2$)$_{1-6}$COO$^-$, a reactive group Z, and a hydrophilic group; and Ln$^{3+}$ is a lanthanide ion.

In one embodiment, R$_1$ and R$_2$, if present, are each independently selected from hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3^H{_2}$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$N$^+$(CH$_3$)$_2$R$_5$, —(CH$_2$)$_{1-6}$OH, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is selected from hydrogen, C$_{1-12}$-alkyl (in particular C$_{1-6}$-alkyl), —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$N$^+$(CH$_3$)$_2$(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, and —(CH$_2$)$_{1-6}$PO$_3^{2-}$.

In another embodiment, R$_1$ and R$_2$, if present, are each independently selected from hydrogen, —(CH$_2$)$_{1-6}$COOH, —(CH$_2$)$_{1-6}$COO$^-$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$N$^+$(CH$_3$)$_2$R$_5$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is selected from —(CH$_2$)$_{1-6}$COOH, and —(CH$_2$)$_{1-6}$COO$^-$.

In embodiments (which may be combined with other embodiments), one of R$_1$ and R$_2$, if present, is selected from —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$N$^+$(CH$_3$)$_2$R$_5$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is a reactive group (optionally including a spacer), in particular R$_5$ is —NCS, while the other of R$_1$ and R$_2$ is as defined above, except that any R$_5$ is not a reactive group. In one variant hereof, one of R$_1$ and R$_2$ is —(CH$_2$)$_{1-6}$—C$_6$H$_4$—NCS, —CO(CH$_2$)$_{1-6}$—C$_6$H$_4$—NCS in particular —CH$_2$—C$_6$H$_4$—NCS.

In still another embodiment, R$_1$ and R$_2$, if present, each independently are selected from hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$N$^+$(CH$_3$)$_2$(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$ PO$_3$H$_2$, —(CH$_2$)$_{1-6}$PO$_3^{2-}$, —(CH$_2$)$_{1-6}$OH, —(CH$_2$)$_{1-6}$C(=O)N(CH$_2$COOH)$_2$, —(CH$_2$)$_{1-6}$C(=O)N(CH$_2$COO$^-$)$_2$, —(CH$_2$CH$_2$O)$_{1-4}$CH$_2$CH$_2$OH, and —(CH$_2$CH$_2$O)$_{1-4}$CH$_2$CH$_2$OCH$_3$; in particular R$_1$ and R$_2$, if present, are each independently selected from hydrogen, —CH$_2$COOH, —CH$_2$COO$^-$, —CH$_2$SO$_3$H, —CH$_2$SO$_3^-$, —CH$_2$—O—PO$_3$H$_2$, —CH$_2$—O—PO$_3^{2-}$, —CH$_2$ PO$_3$H$_2$, —CH$_2$PO$_3^{2-}$, —CH$_2$OH, —CH$_2$C(=O)N(CH$_2$COOH)$_2$, —CH$_2$C(=O)N(CH$_2$COO$^-$)$_2$, —(CH$_2$CH$_2$O)$_{1-4}$CH$_2$CH$_2$OH, and —CH$_2$CH$_2$O)$_{1-4}$CH$_2$CH$_2$OCH$_3$.

When referred to herein, —(CH$_2$)$_{1-6}$ means a straight alkyl chain having 1, 2, 3, 4, 5 or 6 carbon atoms. Preferred examples hereof are —CH$_2$—, —CH$_2$—CH$_2$— and —CH$_2$—CH$_2$—CH$_2$—, in particular —CH$_2$—.

It is presently believed that some types of substituents, i.e. those of the carboxylic acid and sulfonic acid type, are especially interesting. Hence, in a preferred embodiment, R$_1$ and R$_2$ are each independently selected from hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —CH$_2$CONHCH$_2$COOH, —CH$_2$CONHCH$_2$COO$^-$, —CH$_2$CON(CH$_2$COOH)$_2$, —CH$_2$CON(CH$_2$COO$^-$)$_2$, —COCH$_2$NHCH$_2$COOH, —COCH$_2$NHCH$_2$COO$^-$, —COCH$_2$N(CH$_2$COOH)$_2$, and —COCH$_2$N(CH$_2$COO$^-$)$_2$, in particular from —CH$_2$—COOH, —CH$_2$—COO$^-$, —CH$_2$CON(CH$_2$COOH)$_2$, and —CH$_2$CON(CH$_2$COO$^-$)$_2$.

In one embodiment $R_1$ and $R_2$ are each independently selected from —$CH_2$—COOH and —$CH_2$—COO$^-$.

In another embodiment, X is —$CR_1R_2$— wherein both of $R_1$ and $R_2$ are hydrogen.

In one embodiment $R_1$ and $R_2$ are each independently selected from —$(CH_2CH_2O)_{1-4}CH_2CH_2OH$, —$(CH_2CH_2O)_{1-4}CH_2CH_2OCH_3$ in particular from —$(CH_2CH_2O)_2CH_2CH_2OCH_3$.

It should be understood that when the substituents are carboxylates, sulfonates, phosphonates, phosphates and the like, the chelates may include cations as counter ions, e.g. Na$^+$, K$^+$, Ca$^{2+}$ and the like.

In one embodiment, X is >C=O corresponding to a fluorenone chromophore.

In another embodiment, X is >C=N—OR$_1$ corresponding to a fluorenone oxime chromophore. In one variant within this embodiment, $R_1$ is selected from hydrogen, —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}N^+(CH_3)_2(CH_2)_{1-6}SO_3^-$, —$(CH_2CH_2O)_{1-4}CH_2CH_2OH$, —$(CH_2CH_2O)_{1-4}CH_2CH_2OCH_3$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)N(R_5)_2$, —$(CH_2)_{1-6}C(=O)NCH_3R_5$, —$(CH_2)_{1-6}NHC(=O)NHR_5$, —$(CH_2)_{1-6}NHC(=O)N(R_5)_2$, —$(CH_2)_{1-6}NHC(=S)NHR_5$, —$(CH_2)_{1-6}NHC(=S)N(R_5)_2$, —$(CH_2)_{1-6}C(=O)R_5$, wherein $R_5$ is selected from hydrogen, $C_{1-12}$-alkyl (in particular $C_{1-6}$-alkyl), —$(CH_2)_{1-6}COOH$, —$(CH_2)_{1-6}COO^-$, —$(CH_2)_{1-6}SO_3H$, and —$(CH_2)_{1-6}SO_3^-$.

In another embodiment, X is —S— corresponding to a dibenzothiophene.

In still another embodiment, X is —O— corresponding to a dibenzofurane.

In still another embodiment, X is —NR$_1$— corresponding to a 9H-carbazolyl. In one variant within this embodiment, $R_1$ is selected from hydrogen, —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}N^+(CH_3)_2(CH_2)_{1-6}SO_3^-$, —$(CH_2CH_2O)_{1-4}CH_2CH_2OH$, —$(CH_2CH_2O)_{1-4}CH_2CH_2OCH_3$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)N(R_5)_2$, —$(CH_2)_{1-6}C(=O)NCH_3R_5$, —$(CH_2)_{1-6}NHC(=O)NHR_5$, —$(CH_2)_{1-6}NHC(=O)N(R_5)_2$, —$(CH_2)_{1-6}NHC(=S)NHR_5$, —$(CH_2)_{1-6}NHC(=S)N(R_5)_2$, —$(CH_2)_{1-6}C(=O)R_5$, wherein $R_5$ is selected from hydrogen, $C_{1-12}$-alkyl (in particular $C_{1-6}$-alkyl), —$(CH_2)_{1-6}COOH$, —$(CH_2)_{1-6}COO^-$, —$(CH_2)_{1-6}SO_3H$, and —$(CH_2)_{1-6}SO_3^-$.

In still another embodiment, X is —$CR_1R_2$— corresponding to a fluorene. In one variant within this embodiment, $R_1$ and $R_2$ are preferably independently selected from hydrogen, —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}N^+(CH_3)_2(CH_2)_{1-6}SO_3^-$, —$(CH_2CH_2O)_{1-4}CH_2CH_2OH$, —$(CH_2CH_2O)_{1-4}CH_2CH_2OCH_3$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)N(R_5)_2$, —$(CH_2)_{1-6}C(=O)NCH_3R_5$, —$(CH_2)_{1-6}NHC(=O)NHR_5$, —$(CH_2)_{1-6}NHC(=O)N(R_5)_2$, —$(CH_2)_{1-6}NHC(=S)NHR_5$, —$(CH_2)_{1-6}NHC(=S)N(R_5)_2$, —$(CH_2)_{1-6}C(=O)R_5$, wherein $R_5$ is selected from hydrogen, $C_{1-12}$-alkyl (in particular $C_{1-6}$-alkyl), —$(CH_2)_{1-6}COOH$, —$(CH_2)_{1-6}COO^-$, —$(CH_2)_{1-6}SO_3H$, and —$(CH_2)_{1-6}SO_3^-$.

Examples of hydrophilic groups are mono- and oligosaccharides, such as monosaccharides and disaccharides, oligoalkylene glycols (e.g. those having 1-20 repeating units) such as oligoethylene glycol and oligopropylene glycol, etc.

In one embodiment, the hydrophilic group is selected from monosaccharides, disaccharides, —$(CH_2)_{1-6}CH_2OH$, —$CH(CH_2OH)_2$, —$C(CH_2OH)_3$—$(CH_2)_{1-3}$—O—$(CH_2CH_2O)_{0-5}$—H, —$(CH_2)_{1-3}$—O—$(CH_2CH_2O)_{0-5}$—$C_{1-4}$-alkyl, —O—$(CH_2CH_2O)_{1-6}$—H, and —O—$(CH_2CH_2O)_{1-6}$—$C_{1-4}$-alkyl, in particular monosaccharides.

In the present context, the term "monosaccharide" is intended to mean $C_5$-$C_7$ carbohydrates being either in the acyclic or in cyclic form. Examples of monosaccharides are $C_6$ carbohydrates, e.g. those selected from

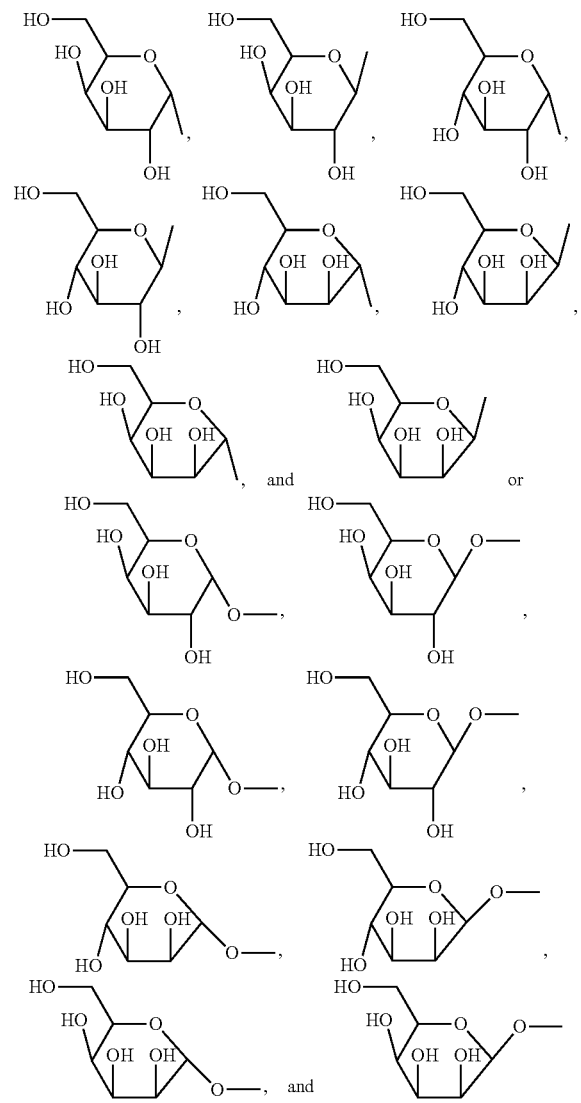

In the present context, the term "disaccharide" is intended to mean two monosaccharides (cf. above) linked together, preferably via glycosidic bonds.

In other possible embodiments, a hydrophilic group (as specified) is present in the chelate structure, but not in the chromophoric moiety of formula (I) or (III).

In some alternative embodiments, the substituents $R_1$ and/or $R_2$ include a reactive group Z, preferably including a spacer (see further below). In such instances, the reactive group Z is facilitating the labelling of a biospecific binding reactant, or is facilitating the formation of a covalent bond to a solid support material. In case the chelate has a polymerizing group as reactive group, then the chelate may be introduced in the solid support, e.g. a particle, simultaneously with the preparation of the particles.

If present, the reactive group Z is typically selected from azido (—$N_3$), alkynyl (—C≡CH), alkylene (—CH=$CH_2$), amino (—$NH_2$), aminooxy (—O—$NH_2$), carboxyl (—COOH), aldehyde (—CHO), hydrazide (—$CONHNH_2$), mercapto (—SH), maleimido, activated derivatives of maleimido, isocyanato (—NCO), isothiocyanato (—NCS), diazonium (—$N^+N$), bromoacetamido, iodoacetamido, reactive esters, pyridyl-2-dithio, and 6-substituted 4-chloro-1,3,5-triazin-2-ylamino, in particular, the reactive group comprises a isothiocyanato (—NCS) group. The substituents in 6-substituted 4-chloro-1,3,5-triazin-2-ylamino can be selected from the group consisting of hydrogen, halogen, alkoxy, aryloxy, amino, $C_{1-6}$-alkyl, substituted amino or thioethers, and preferable selected from the group consisting of chloro, fluoro, ethoxy, 2-methoxyethoxy, 2-cyanoethoxy, 2,2,2-trifluoroethoxy, thiophenoxy or ethoxycarbonyl-thiomethoxy. The substituted amino or thioether is preferable mono- or disubstituted each substituent being preferable independently selected from $C_{1-6}$-alkyl, $C_{1-6}$-alkyl-O—, phenyl, carbonyl or carboxyl.

It follows that upon reaction with a biospecific binding reactant (see further below), the reactive group Z establishes a link to said biospecific binding reactant, e.g. of one of the following types: a thiourea (—NH—C(=S)—NH—), an aminoacetamide (—NH—CO—$CH_2$—NH—), an amide (—NH—CO—, —CO—NH—, —$NCH_3$—CO— and —CO—$NCH_3$—), oxime (—O—N=CH—), hydrazone (—CO—NH—NH=CH—) (and aliphatic thioether (—S—), a disulfide (—S—S—), a 6-substituted-1,3,5-triazine-2,4-diamine, a

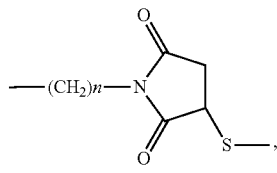

wherein n=1-6; and a triazole (e.g. formed by the so-called "click" chemistry).

In other possible embodiments, a reactive group Z (as specified) is present in the chelate structure, but not in the chromophoric moiety of formula (I).

It should be understood that when a reactive group Z is present, the group Z may include a spacer, i.e. a distance-making biradical, so as—if necessary or desirable—to position the reactive group Z in a position accessible for reaction with the biospecific binding reactant. Similarly, when any of $R_1$ and $R_2$ includes a hydrophilic group, the hydrophilic group may include a spacer. In both instances, the spacer may be readily introduced in the course of the synthesis of the ligand or the chelate.

The term "spacer" is intended to mean a distance-making group between, e.g., a conjugating group or a pyridine moiety of the core structure and, e.g. the reactive group Z or a hydrophilic group. The spacer typically has a length of 1-20 bonds between the attachment point and reactive group (or hydrophilic group), such as 3-15 bonds, or 5-12 bonds. The said spacer is formed of one to five moieties, each moiety selected from the group consisting of phenylene, —$C_{1-10}$-alkylene-, an ethynediyl (—C≡C—), an ethylenediyl (—C=C—), an ether (—O—), a thioether (—S—), a disulfide (—S—S—), an amide (—C(=O)—NH—, —NH—C(=O)—, —C(=O)—$NCH_3$— and —$NCH_3$—C(=O)—), a carbonyl (—CO—), an ester (—COO— and —OOC—), a sulfoamide (—$SO_2$—NH—, —$SO_2$—NR—), a sulfone (—$SO_2$—), a phosphate (—O—$PO_2$—O—), a diaza (—N=N—), a tertiary amine, a thiourea (—NH—C(=S)—NH—), oxime (—O—N=CH—), hydrazone (—CO—NH—NH=CH—) and a triazole, in which R represents an alkyl group consisting 1-10 carbon atoms In some embodiments, at least one of the substituents $R_1$ and/or $R_2$ include an oligopeptide, a polypeptide or a polynucleotide.

$R_3$ and $R_4$ each represent a bond between the chromophoric moiety and other moieties of the chelate, e.g. chromophoric moieties and chelating moieties. The chelating moiety comprising at least two carboxylic acid or phosphoric acid groups, esters, amides or salts of said acids, attached to an aromatic unit of the chromophoric moiety, either directly or via a cyclic or acyclic N- and/or O-containing hydrocarbon chain. It should be understood that the chromophoric moiety of formula (I) and/or (III) may replace any other chromophoric moiety(ies) in conventional chelates. Hence, it is appreciated that the chromophoric moiety of formula (I) and/or (III) can simply be incorporated in conventional chelates having other chromophoric moieties either similar or different to the chromophoric moiety of formula (I) or (III). Illustrative examples are provided in the examples section.

$R_3$ and $R_4$ each represent a bond to other moieties of the chelate, e.g. to another chromophoric moiety, typically via a linker, or to a complexing group (e.g. —COOH/—COO⁻), or simply to an end group or a hydrogen atom.

In one variant, one or both of $R_3$ and —$CH_2$—$R_4$ may be —$(CH_2)_{1-3}$N($R_7$)—$(CH_2)_{1-3}$— wherein $R_7$ is —$(CH_2)_{1-6}$-aryl where aryl (e.g. phenyl) may be substituted with a reactive group Z as defined above.

In another variant, one or both of $R_3$ and —$CH_2$—$R_4$ may be —$(CH_2)_{1-3}$N($R_8$)—$(CH_2)_{1-3}$—Chr, —$(CH_2)_{1-3}$O$(CH_2)_{1-3}$—Chr, or —$(CH_2)_{1-3}$S$(CH_2)_{1-3}$—Chr, wherein $R_8$ is selected from —$(CH_2)_{1-6}$COOH, —$(CH_2)_{1-6}$COO⁻, —$(CH_2)_{1-6}$$SO_3$H, —$(CH_2)_{1-6}$$SO_3^-$, —$(CH_2)_{1-6}$—O—$PO_3H_2$, —$(CH_2)_{1-6}$—O—$PO_3^{2-}$, —$(CH_2)_{1-6}$$PO_3H_2$, —$(CH_2)_{1-6}$$PO_3^{2-}$, —$(CH_2)_{1-6}$NH$R_5$, —$(CH_2)_{1-6}$$NCH_3R_5$, —$(CH_2)_{1-6}$NEt$R_5$, —$(CH_2)_{1-6}$N($R_5$)$_2$, —$(CH_2)_{1-6}$NHC(=O)$R_5$, —$(CH_2)_{1-6}$$NCH_3$C(=O)$R_5$, —$(CH_2)_{1-6}$C(=O)NH$R_5$, —$(CH_2)_{1-6}$C(=O)$NCH_3R_5$, —$(CH_2)_{1-6}$NHC(=O)NH$R_5$, —$(CH_2)_{1-6}$NHC(=S)NH$R_5$, —$(CH_2)_{1-6}$C(=O)$R_5$, —$(CH_2)_{1-6}$—$C_6H_4$—$R_5$, —COR$_5$, —CO(CH$_2$)$_{1-6}$NH$R_5$, and —CO(CH$_2$)$_{1-6}$NCH$_3R_5$, —$(CH_2)_{1-10}$OH, —$(CH_2)_{1-10}$OR$_5$, —$(CH_2)_{1-10}$NH$_2$, —$(CH_2)_{1-10}$NH$R_5$, —$(CH_2)_{1-10}$NCH$_3R_5$, —$(CH_2)_{1-10}$SH, —$(CH_2)_{1-10}$SR$_5$ wherein $R_5$ is selected from —$(CH_2)_{1-6}$COOH, —$(CH_2)_{1-6}$COO⁻, —$(CH_2)_{1-6}$$SO_3$H, —$(CH_2)_{1-6}$hu $SO_3^-$, —$(CH_2)_{1-6}$—O—$PO_3H_2$, —$(CH_2)_{1-6}$—O—$PO_3^{2-}$, —$(CH_2)_{1-6}$$PO_3H_2$, —$(CH_2)_{1-6}$$PO_3^{2-}$, and a reactive group Z, and wherein Chr represents another chromophoric moiety.

In still another variant (which may be combined with other embodiments), one or both of $R_3$ and —$CH_2$—$R_4$ are independently selected from —$CH_2$—N(CH$_2$COOH)$_2$ and —$CH_2$—N(CH$_2$COO⁻)$_2$, In still another variant (which may be combined with other embodiments) in which one or both $R_3$ and $R_4$ are independently selected from —COOH, —COO⁻, —$PO_3H_2$—$PO_3^{2-}$, —P(CH$_3$)O$_2$H, —P(CH$_3$)O$_2^-$, —P(Ph)O$_2$H and —P(Ph)O$_2^-$.

Examples of representative $R_3$ and $R_4$ and chelate designs in which the disclosed pyridine based chromophoric moieties can be replaced by the chromophores of present invention are e.g. in following publications Hovinen, J., et al., Bioconjugate Chem., 20(2009)404; He., S., et al., Organic Lett., 13(2011), 5036; Wang., Q., et al., Inorg. Chem., 52 (2013)8461; Butler, S. J., et al., Chem Eur. J., 19(2013)9511 and WO 2013/011236.

In one embodiment, the groups —$R_3$ and —$CH_2$—$R_4$ each independently are selected from —$(CH_2)_{1-6}H$, —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}$—O—$PO_3H_2$, —$(CH_2)_{1-6}$—O—$PO_3^{2-}$, —$(CH_2)_{1-6}PO_3H_2$, —$(CH_2)_{1-6}PO_3^{2-}$, —$(CH_2)_{1-6}NHR_5$, —$(CH_2)_{1-6}NCH_3R_5$, —$(CH_2)_{1-6}NEtR_5$, —$(CH_2)_{1-6}N(R_5)_2$, —$(CH_2)_{1-6}OH$, —$(CH_2)_{1-6}OR_5$, —$(CH_2)_{1-6}SH$, —$(CH_2)_{1-6}SR_5$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}NHC(=O)NHR_5$, —$(CH_2)_{1-6}NHC(=S)NHR_5$, —$(CH_2)_{1-6}C(=O)R_5$, and —$(CH_2)_{1-6}$—$C_6H_4$—$R_5$, or the groups —$R_3$ and —$R_4$ each independently are selected from —$(CH_2CH_2O)_{1-4}CH_2CH_2OH$, —$(CH_2CH_2O)_{1-4}CH_2CH_2OCH_3$, —$COR_5$, —$CO(CH_2)_{1-6}NHR_5$, —$CO(CH_2)_{1-6}NCH_3R_5$, —$CONH(CH_2)_{1-6}OH$, —$CONH(CH_2)_{1-6}OR_5$, —$CONH(CH_2)_{1-6}SH$, —$CONH(CH_2)_{1-6}SR_5$, —$CONH(CH_2)_{1-6}NH_2$, and —$CONH(CH_2)_{1-6}NHR_5$, wherein $R_5$ is selected from hydrogen, $C_{1-12}$-alkyl, —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}$—O—$PO_3H_2$, —$(CH_2)_{1-6}$—O—$PO_3^{2-}$, —$(CH_2)_{1-6}PO_3H_2$, —$(CH_2)_{1-6}PO_3^{2-}$, a hydrophilic group (optionally including a spacer), a reactive group (optionally including a spacer), an oligopeptide, a polypeptide and a nucleotide.

In one particularly interesting variant, the groups —$R_3$ and —$CH_2$—$R_4$ each independently are selected from —$(CH_2)_{1-6}COOH$, —$(CH_2)_{1-6}COO^-$, —$(CH_2)_{1-6}SO_3H$, —$(CH_2)_{1-6}SO_3^-$, —$(CH_2)_{1-6}$—O—$PO_3H_2$, —$(CH_2)_{1-6}$—O—$PO_3^{2-}$, —$(CH_2)_{1-6}PO_3H_2$, —$(CH_2)_{1-6}PO_3^{2-}$, —$(CH_2)_{1-6}NHR_5$, —$(CH_2)_{1-6}NCH_3R_5$, —$(CH_2)_{1-6}NEtR_5$, —$(CH_2)_{1-6}N(R_5)_2$, —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}NHC(=O)NHR_5$, —$(CH_2)_{1-6}NHC(=S)NHR_5$, —$(CH_2)_{1-6}C(=O)R_5$, and —$(CH_2)_{1-6}$—$C_6H_4$—$R_5$, or the groups —$R_3$ and —$R_4$ each independently are selected from —$COR_5$, —$CO(CH_2)_{1-6}NHR_5$, and —$CO(CH_2)_{1-6}NCH_3R_5$, wherein $R_5$ is selected from —$(CH_2)_{1-6}COOH$, —$(CH_2)_{1-6}COO^-$, —$(CH_2)_{1-6}SO_3H$, —$(CH_2)_{1-6}SO_3$, —$(CH_2)_{1-6}$—O—$PO_3H_2$, —$(CH_2)_{1-6}$—O—$PO_3^{2-}$, —$(CH_2)_{1-6}PO_3H_2$, and —$(CH_2)_{1-6}PO_3^{2-}$.

In one embodiment (which may be combined with other embodiments), one of $R_3$ and —$CH_2$—$R_4$ are independently selected from —$(CH_2)_{1-6}NHC(=O)R_5$, —$(CH_2)_{1-6}NCH_3C(=O)R_5$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=N(R_5)_2$, —$(CH_2)_{1-6}NHC(=O)NHR_5$, —$(CH_2)_{1-6}NHC(=S)NHR_5$, —$(CH_2)_{1-6}C(=O)R_5$, and —$(CH_2)_{1-6}$—$C_6H_4$—$R_5$, wherein $R_5$ is selected from a hydrophilic group (optionally including a spacer), a reactive group (optionally including a spacer), an oligopeptide, a polypeptide and a nucleotide. In one variant $R_5$ is a reactive group (optionally including a spacer).

The substituent(s) $R_6$ is/are typically selected from hydrogen —Cl, —Br, —F, —I, —$CH_3$, —$CF_3$, —CN, —$NO_2$, —OH, —$OCH_3$, —$SCH_3$, —$CONH_2$, —$CONHCH_3$, —$CON(CH_3)_2$, —$NHCOCH_3$, a reactive group Z, and a hydrophilic group. In some embodiments, $R_6$ is absent. In other embodiments, one $R_6$ is a reactive group, cf. above.

In some interesting embodiments, the chelate has a total of two or three chromophoric groups, e.g. as illustrated with the compounds 47, 48, 49, 50, 53, 54, 57, 58, 64, 65, 66, 78, 79 and 80.

The term "lanthanide ion" or "$Ln^{3+}$" is intended to mean a trivalent ion of the lanthanide series of the Periodic Table of Elements, e.g. europium(III), terbium(III), samarium(III) and dysprosium(III), i.e. $Eu^{3+}$, $Tb^{3+}$, $Sm^{3+}$ or $Dy^{3+}$. In many embodiments europium(III) ($Eu^{3+}$) is preferred.

Moreover, the invention provides highly luminescent labels for all lanthanides which provides multi-label possibilities.

Particular Embodiments

In some particular embodiments, the chelate has one of the structural formulae (A-I), (A-III), (B-I), (B-I*), (B-III), (B-III*), (C-I), (C-III), (D-I) and (D-III) below:

(A-I) corresponding to compounds of 14, 40, 41, 42:

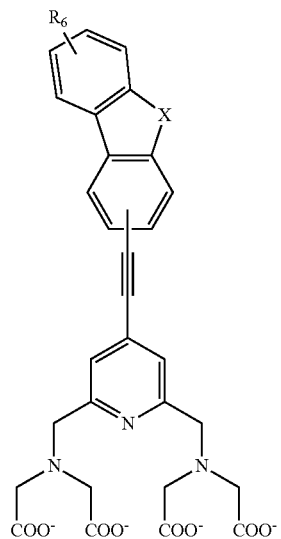

(A-III) corresponding to compounds 11, 12, 26, 27, 28, 30:

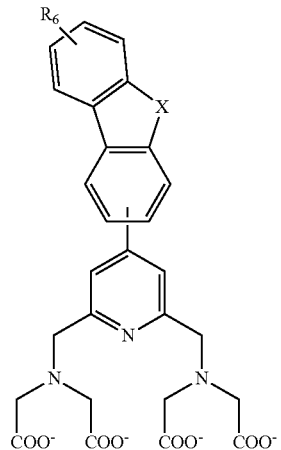

(B-I) corresponding to compounds 45, 46, 47, 48, 49, 50:
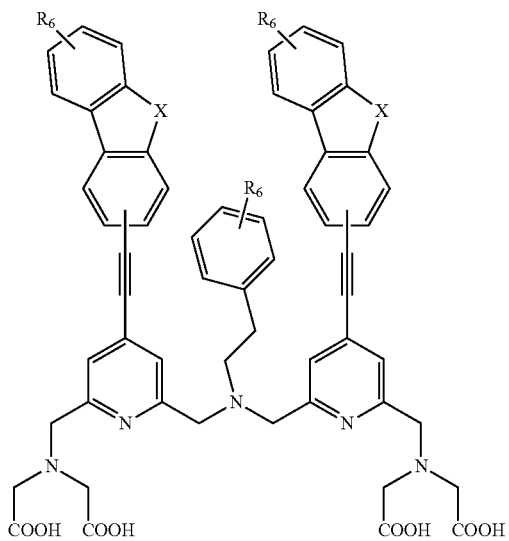
(B-I*):
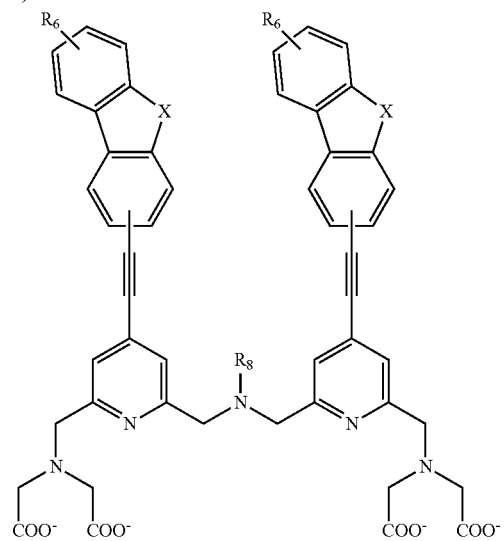
(B-III) corresponding to compounds 52, 53, 54, 56, 57, 58:
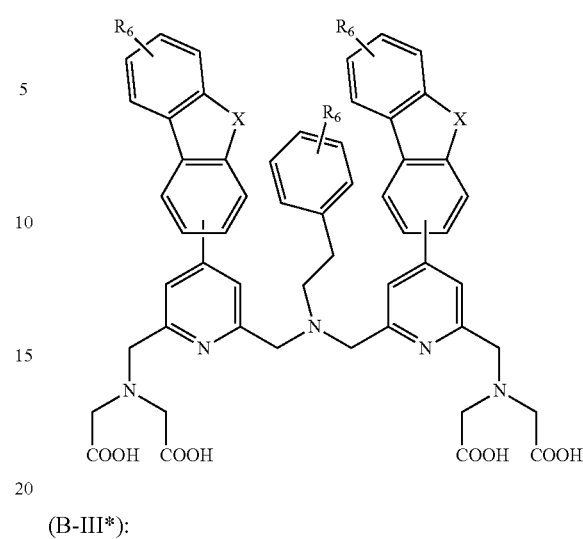
(B-III*):
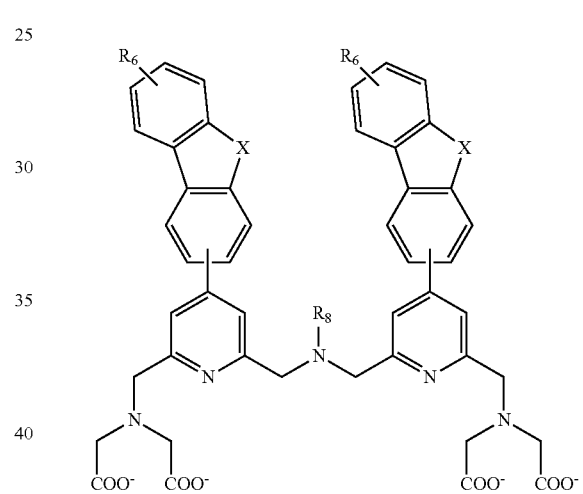
(C-I) corresponding to compounds 64, 65, 66
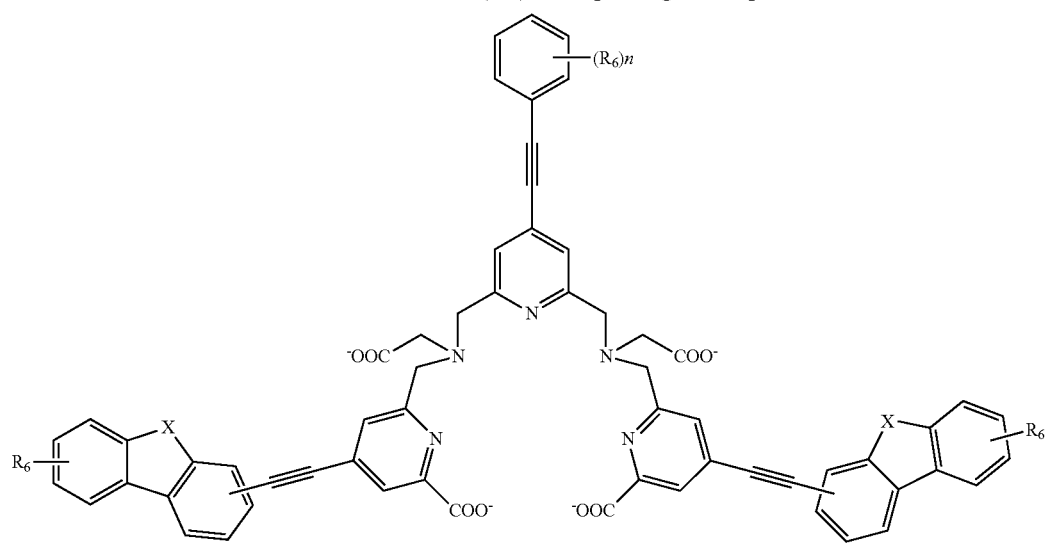
wherein n=1-5

(C-III):
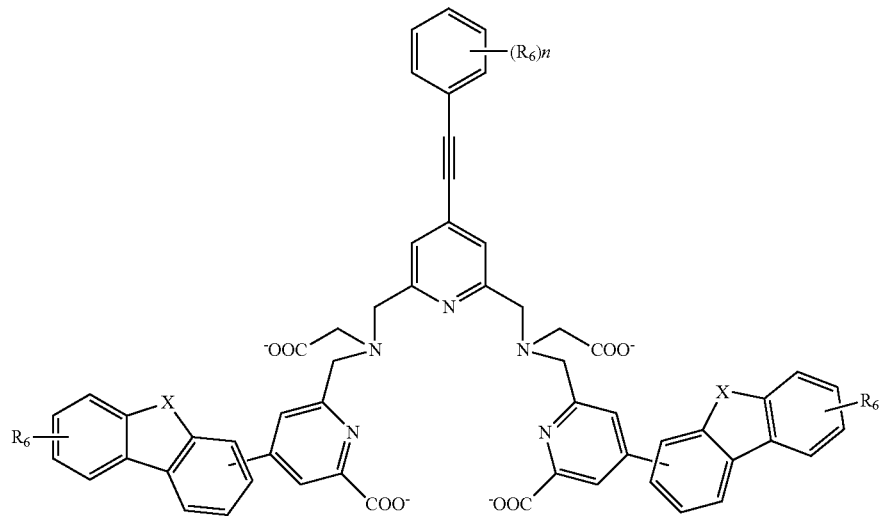
wherein n=1-5
(D-I) corresponding to compounds 78, 79:
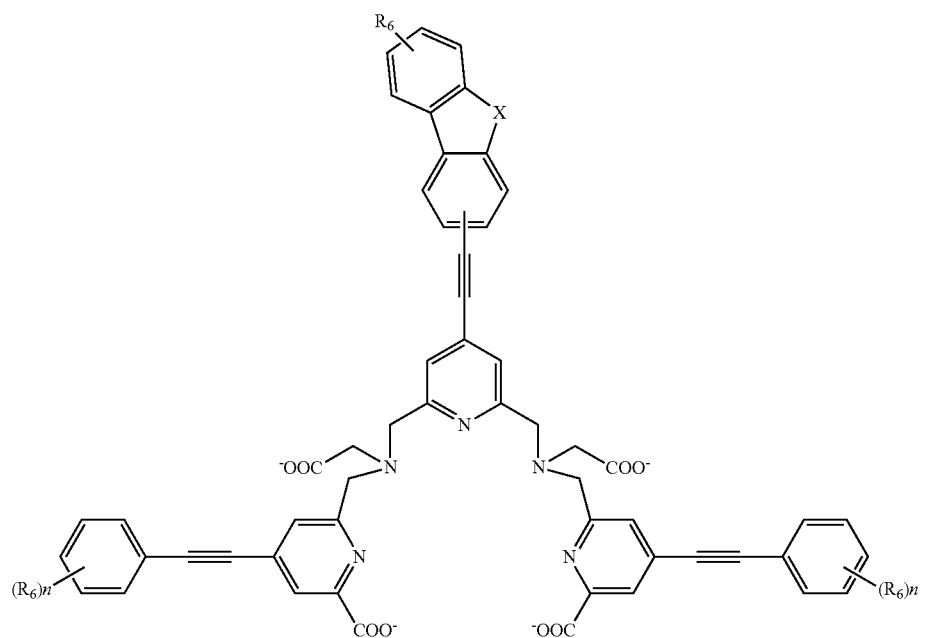
wherein n=1-5

(D-III):

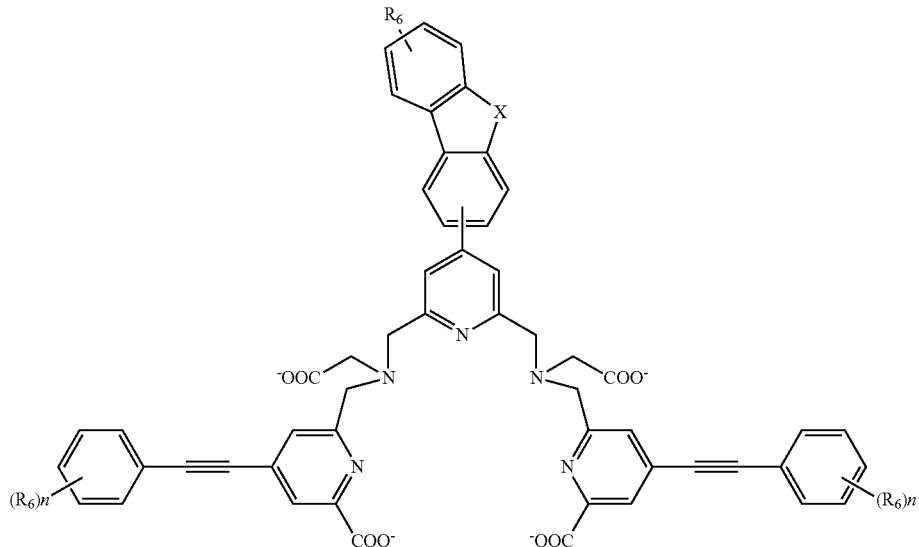

In each of the formulas (A-I), (A-III), (B-I), (B-I*), (B-III), (B-III*), (C-I), (C-III), (D-I) and (D-III) X, $R_3$, $R_4$, $R_6$ and $R_8$ represents the groups X, $R_3$, $R_4$, $R_6$ and $R_8$, respectively, as defined hereinabove for formula (I) and (IIII). Each and every specification, embodiment, variant and preference (or the like) described above for formula (I) and (III) should also be construed as corresponding embodiments, variants and preferences for the formulas (A-I), (A-III), (B-I), (B-I*), (B-III), (B-III), (C-I), (C-III), (D-I) and (D-III).

In one preferred embodiment, the chelate has the formula (A-I) or (A-III). In one variant hereof X is —$NHR_1$ or —$CR_1R_2$—, $R_1$ and $R_2$, if present, are each independently selected from hydrogen, —$(CH_2)_{1-6}COOH$, —$(CH_2)_{1-6}COO^-$, —$(CH_2)_{1-6}N^+(CH_3)_2R_5$, —$(CH_2CH_2O)_{1-4}CH_2CH_2OH$, —$CH_2CH_2O)_{1-4}CH_2CH_2OCH_3$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}NHC(=O)NHR_5$, —$(CH_2)_{1-6}NHC(=S)NHR_5$, —$(CH_2)_{1-6}C(=O)R_5$, —$CH_2)_{1-6}$—$C_6H_4$—$R_5$, —$COR_5$, —$CO(CH_2)_{1-6}NHR_5$, and —$CO(CH_2)_{1-6}NCH_3R_5$, wherein $R_5$ is selected from —$(CH_2)_{1-6}COOH$, and —$(CH_2)_{1-6}COO^-$. In particular $R_1$ and $R_2$, if present, are each independently selected from hydrogen, —$(CH_2)_{1-6}COOH$, —$(CH_2)_{1-6}COO^-$, —$(CH_2CH_2O)_{1-4}CH_2CH_2OH$, —$(CH_2CH_2O)_{1-4}CH_2CH_2OCH_3$, and —$(CH_2)_{1-6}C(=O)N(R_5)_2$, wherein $R_5$ is selected from —$(CH_2)_{1-6}COOH$, and —$(CH_2)_{1-6}COO^-$; especially from hydrogen, —$CH_2COOH$, —$CH_2COO^-$, —$(CH_2CH_2O)_{1-4}CH_2CH_2OH$, —$(CH_2CH_2O)_{1-4}CH_2CH_2OCH_3$, —$CH_2C(=O)N(CH_2COOH)_2$, and —$CH_2C(=O)N(CH_2COO^-)_2$.

In another preferred embodiment, the chelate has the formula (B-I) or (B-I) or (B-III) or (B-III*). In one variant hereof X is —NHR, or —$CR_1R_2$—, $R_1$ and $R_2$, if present, are each independently selected from hydrogen, —$(CH_2)_{1-6}COOH$, —$(CH_2)_{1-6}COO^-$, —$(CH_2)_{1-6}N^+(CH_3)_2R_5$, —$(CH_2CH_2O)_{1-4}CH_2CH_2OH$, —$(CH_2CH_2O)_{1-4}CH_2CH_2OCH_3$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}NHC(=O)NHR_5$, —$(CH_2)_{1-6}NHC(=S)NHR_5$, —$(CH_2)_{1-6}C(=O)R_5$, —$(CH_2)_{1-6}$—$C_6H_4$—$R_5$, —$COR_5$, —$CO(CH_2)_{1-6}NHR_5$, and —$CO(CH_2)_{1-6}NCH_3R_5$, wherein $R_5$ is selected from —$(CH_2)_{1-6}COOH$, and —$(CH_2)_{1-6}COO^-$. In particular $R_1$ and $R_2$, if present, are each independently selected from hydrogen, —$(CH_2)_{1-6}COOH$, —$(CH_2)_{1-6}COO^-$, —$(CH_2CH_2O)_{1-4}CH_2CH_2OH$, —$(CH_2CH_2O)_{1-4}CH_2CH_2OCH_3$, and —$(CH_2)_{1-6}C(=O)N(R_5)_2$, wherein $R_5$ is selected from —$(CH_2)_{1-6}COOH$, and —$(CH_2)_{1-6}COO^-$; especially from hydrogen, —$CH_2COOH$, —$CH_2COO^-$, —$(CH_2CH_2O)_{1-4}CH_2CH_2OH$, —$(CH_2CH_2O)_{1-4}CH_2CH_2OCH_3$, —$CH_2C(=O)N(CH_2COOH)_2$, and —$CH_2C(=O)N(CH_2COO^-)_2$.

In yet another preferred embodiment, the chelate has the formula (C-I) or (C-III). In one variant hereof X is —$NHR_1$ or —$CR_1R_2$—, $R_1$ and $R_2$, if present, are each independently selected from hydrogen, —$(CH_2)_{1-6}COOH$, —$(CH_2)_{1-6}COO^-$, —$(CH_2)_{1-6}N^+(CH_3)_2R_5$, —$(CH_2CH_2O)_{1-4}CH_2CH_2OH$, —$(CH_2CH_2O)_{1-4}CH_2CH_2OCH_3$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}C(=O)^{NHR}{}_5$, —$(CH_2)_{1-6}NHC(=S)NHR_5$, —$(CH_2)_{1-6}C(=O)R_5$, —$(CH_2)_{1-6}$—$C_6H_4$—$R_5$, —$COR_5$, —$CO(CH_2)_{1-6}NHR_5$, and —$CO(CH_2)_{1-6}NCH_3R_5$, wherein $R_5$ is selected from —$(CH_2)_{1-5}COOH$, and —$(CH_2)_{1-6}COO^-$. In particular $R_1$ and $R_2$, if present, are each independently selected from hydrogen, —$(CH_2)_{1-6}COOH$, —$(CH_2)_{1-6}COO^-$, —$(CH_2CH_2O)_{1-4}CH_2CH_2OH$, —$(CH_2CH_2O)_{1-4}CH_2CH_2OCH_3$, and —$(CH_2)_{1-6}C(=O)N(R_5)_2$, wherein $R_5$ is selected from —$(CH_2)_{1-6}COOH$, and —$(CH_2)_{1-6}COO^-$; especially from hydrogen, —$CH_2COOH$, —$CH_2COO^-$, —$(CH_2CH_2O)_{1-4}CH_2CH_2OH$, —$(CH_2CH_2O)_{1-4}CH_2CH_2OCH_3$, —$CH_2C(=O)N(CH_2COOH)_2$, and —$CH_2C(=O)N(CH_2COO^-)_2$.

In still another preferred embodiment, the chelate has the formula (D-I) or (D-III). In one variant hereof X is —$NHR_1$ or —$CR_1R_2$—, $R_1$ and $R_2$, if present, are each independently selected from hydrogen, —$(CH_2)_{1-6}COOH$, —$(CH_2)_{1-6}COO$, —$(CH_2)_{1-6}N^+(CH_3)_2R_5$, —$(CH_2CH_2O)_{1-4}CH_2CH_2OH$, —$(CH_2CH_2O)_{1-4}CH_2CH_2OCH_3$, —$(CH_2)_{1-6}C(=O)NHR_5$, —$(CH_2)_{1-6}C(=O)NCH_3R_5$, —$(CH_2)_{1-6}C(=O)NEtR_5$, —$(CH_2)_{1-6}C(=O)N(R_5)_2$, —$(CH_2)_{1-6}NHC (=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is selected from —(CH$_2$)$_{1-6}$COOH, and —(CH$_2$)$_{1-6}$COO$^-$. In particular R$_1$ and R$_2$, if present, are each independently selected from hydrogen, —(CH$_2$)$_{1-6}$COOH, —(CH$_2$)$_{1-6}$COO$^-$, —(CH$_2$CH$_2$O)$_{1-4}$CH$_2$CH$_2$OH, —(CH$_2$CH$_2$O)$_{1-4}$CH$_2$CH$_2$OCH$_3$, and —(CH$_2$)$_{1-6}$C(=O)N(R$_5$)$_2$, wherein R$_5$ is selected from —(CH$_2$)$_{1-6}$COOH, and —(CH$_2$)$_{1-6}$COO$^-$; especially from hydrogen, —CH$_2$COOH, —CH$_2$COO$^-$, —(CH$_2$CH$_2$O)$_{1-4}$CH$_2$CH$_2$OH, —(CH$_2$CH$_2$O)$_{1-4}$CH$_2$CH$_2$OCH$_3$, —CH$_2$C(=O)N(CH$_2$COOH)$_2$, and —CH$_2$C(=O)N(CH$_2$COO$^-$)$_2$.

It is further envisaged, that although Eu$^{3+}$ is preferred in the chelates of formula (A-I), (A-III), (B-I), (B-I*), (B-III), (B-III*), (C-I), (C-III), (D-I) and (D-III), it may be replaced by any other lanthanide selected from Tb$^{3+}$, Sm$^{3+}$ or Dy$^{3+}$.

Particularly interesting are the lanthanide chelates based on any one of the structures 11, 12, 14, 49, 54, 66, and 80.

Lanthanide Chelating Ligand

Hence, another aspect of the present invention relates to a lanthanide chelating ligand comprising one or more chromophoric moieties of the formula (II) or of the formula (IV)

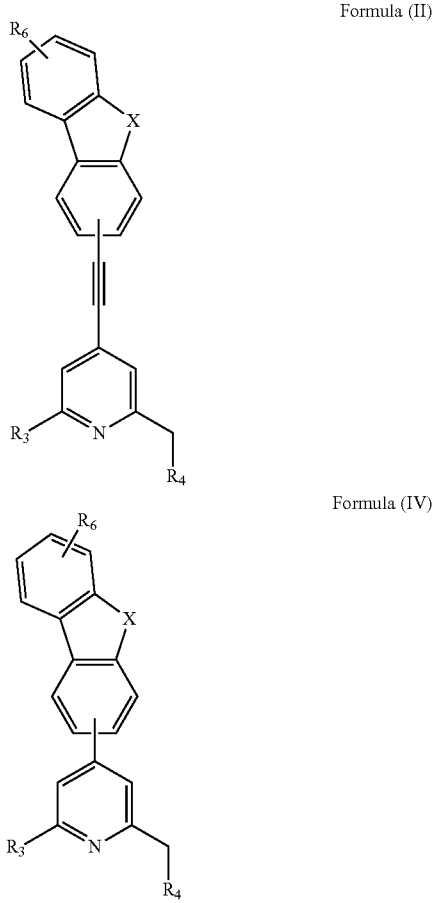

Formula (II)

Formula (IV)

wherein each of X, R$_3$, R$_4$ and R$_6$ represents the groups X, R$_3$, R$_4$ and R$_6$, respectively, as defined hereinabove for formula (I) and (III).

In some interesting embodiments, lanthanide chelating ligand has one of the formulas (A-I), (A-III), (B-I) or (B-III) above (excluding the Eu$^{3+}$).

A Detectable Molecule

Still another aspect of the present invention relates to a detectable molecule comprising a biospecific binding reactant conjugated to a luminescent lanthanide chelate as defined hereinabove. Conjugation is typically obtained by means of a reactive group of said chelate.

The biospecific binding reactant should be capable of specifically binding an analyte of interest for the purpose of quantitative or qualitative analysis of said analyte in a sample.

Examples of biospecific binding reactants are those selected from an antibody, an antigen, a receptor ligand, a specific binding protein, a DNA probe, a RNA probe, an oligopeptide, an oligonucleotide, a modified oligonucleotide (e.g. an LNA modified oligonucleotide), a modified polynucleotide (e.g. an LNA modified polynucleotide), a protein, an oligosaccharide, a polysaccharide, a phospholipid, a PNA, a steroid, a hapten, a drug, a receptor binding ligand, and lectine.

In a preferred embodiment, the biospecific binding reactant is selected from antibodies, e.g. Troponin I antibodies (anti-TnI).

A Method for Carrying out a Biospecific Binding Assay

A still further aspect of the invention relates to a method of carrying out a biospecific binding assay, wherein the method comprises the steps of:

a) forming a biocomplex between an analyte and a biospecific binding reactant labelled with a lanthanide chelate as defined herein;

b) exciting said biocomplex with radiation having an excitation wavelength, thereby forming an excited biocomplex; and c) detecting emission radiation emitted from said excited biocomplex.

In step b), the excitation wavelength is preferably 300 nm or longer, e.g. around 320-380 nm, and significant extend of excitation can be obtained from 360 to 380 nm The method follows the conventional assay steps as will be evident for the skilled person.

This being said, a further aspect of the invention relates to the use of a detectable molecule as defined above in a specific bioaffinity based binding assay utilizing time-resolved fluorometric determination of a specific luminescence. In one embodiment, the specific bioaffinity based binding assay is a heterogeneous immunoassay, a homogenous immunoassay, a DNA hybridization assay, a receptor binding assay, an immunocytochemical or an immunohistochemical assay.

A Solid Support

Still another aspect of the invention relates to a solid support material conjugated with a luminescent lanthanide chelate as defined hereinabove. The luminescent lanthanide chelate is typically immobilized to the solid support material either covalently or non-covalently.

In some interesting embodiments, the solid support material is selected from a nanoparticle, a microparticle, a slide, a plate, and a solid phase synthesis resin.

The novel lanthanide chelates ligands and the corresponding luminescent lanthanide chelates and labeled biospecific binding reactant are based on an open chain, i.e. acyclic, ligand structure which provides surprisingly efficiently excitation of the chelated lanthanide ion. At the same time, all important features of the luminescent lanthanide chelate and labeled biospecific binding reactant can be retained without any additional formation of aggregates and purification problems.

The chelates of the present invention aim to combine several important features in a single label such as:

(a) The excitation shift towards longer wavelengths (see the Examples) enables the use of UV LEDs as an excitation source which will provide a cost reduction in instrument manufacturing, and the possibility of instrument miniaturization.
(b) High absorptivity ($\varepsilon$) combined with appropriate quantum yield ($\Phi$) offers extended brightness ($\varepsilon \times \Phi$) to be used in sensitive time-resolved bioassays.
(c) The chelates are applicable to different lanthanides.
(d) It is possible to decrease the labeling degree without loss of signal.
(e) The lower degree of labeling can improve the affinity of the biomolecule and decrease unspecific binding during the assay. Thus faster kinetic is possible and lower background is seen which can also improve the assay sensitivity.
(f) Reduction of unwanted adsorption properties of the chromophore moiety with improved aqueous solubility, especially concerning chelates with several aromatic chromophore moieties. This should reduce the unspecific binding of the labeled antibody and give improved assay sensitivity.

EXAMPLES

The following non-limiting examples are aimed to further demonstrate the invention.

FC=Flash chromatography. RT=room temperature. Microwave synthesizer was Initiator system (Biotage). $^1$H NMR and $^{13}$C NMR spectra were recorded on a Bruker AVANCE 500 DRX (Bruker, Karlsruhe, Germany) by using SiMe$_4$ as internal standard and chemical shifts $\delta$ are in ppm. Mass spectra were recoded on a Voyager DE Pro (Applied Biosystems, Foster City, Calif.) mass spectrometer. HPLC runs were performed by Dionex's Ultimate 3000 system including Dionex's Ultimate 3000 Diode Array Detector. The used column was ThermoHypersil 150×4 mm 5µ Hypersil® ODS. Used eluents were 100 mM TEAA and CH$_3$CN. Runs were performed by using an eluent gradient starting from 75% H$_2$O, 20% 100 mM TEAA and 5% CH$_3$CN and within 30 min to 30% H$_2$O, 20% TEAA and 50% CH$_3$CN. For the HPLC, sample concentration was aprox. 1 mg of chelate in 1 ml water. The sampling volume was 20-25 µl. The instrumentation, measurement and calculation principles for the molar absorptivities ($\varepsilon$), excitation maxima ($\lambda_{exc}$), luminescence lifetimes ($\tau$), quantum yields ($\Phi$), and triplet stage energies (T) see e.g. Räsänen, M., et al., 2014, J. Luminescence, 146, 211-217.

Example 1

Synthesis of Compound 1

A mixture of 2-bromofluorene (0.74 g, 3.0 mmol), bis(pinacolato)diboran (1.22 g, 4.8 mmol) and KOAc (0.88 g, 9.0 mmol) in DMF (30 ml) was de-aerated with argon. After an addition of [1,1'-bis(diphenylphosphine)ferrocene]dichloropalladium(II) complex with CH$_2$Cl$_2$ (0.12 g, 0.15 mmol), the reaction mixture was stirred at 60° C. for 22 h. Water (30 ml) was added, the mixture was extracted with Et$_2$O (50 ml+20 ml), and the combined organic phases were dried with Na$_2$SO$_4$. The product was purified by FC (silica gel, 20% EtOAc in petroleum ether (b.p. 40-65° C.)). Yield: 0.88 g (100%). $^1$H-NMR (CDCl$_3$): 1.37 (12 H, s); 7.32 (1 H, td, J=7.4 and 1.1 Hz); 7.38 (1 H, t, J=7.4 Hz); 7.55 (1H, d, J=7.4 Hz); 7.80 (1 H, d. J=7.7 Hz); 7.82 (1 H, d. J=7.4 Hz); 7.84 (1H, d, J=7.7 Hz); 8.00 (1 H, s). $^{13}$C-NMR (CDCl$_3$): 24.99; 36.74, 83.78; 119.29; 120.39; 125.14; 126.76; 127.23; 131.29; 133.40; 134.76; 141.54; 142.47; 143.92; 144.59. MALDI TOF-MS mass: calculated (M+H$^+$) 293.19; found 293.51.

Example 2

Synthesis of Compound 2

2-Bromofluorene (1.23 g, 5 mmol) was added to a mixture of NaH (0.36 g, 15 mmol) and dry DMF (25 ml) under argon. After stirring for 5 min, BrCH$_2$COOtBu (2.21 ml, 15 mmol) was added, the mixture was stirred at RT for 10 min and at 65° C. for 23 h. The mixture was dissolved in CH$_2$Cl$_2$ (60 ml), washed with H$_2$O (3×30 ml) and dried with Na$_2$SO$_4$. The product was purified by FC (silica gel, first 5% then 10% EtOAc in petroleum ether (b.p. 40-65° C.)). Yield: 1.89 g (80%). $^1$H-NMR (CDCl$_3$): 1.06 (18 H, s); 2.89 (2 H, d, J=14.2 Hz); 2.98 (2 H, d, J=14.2 Hz); 7.33 (1 H, td, J=7.3 and 1.5 Hz), 7.35 (1 H, td, J=7.3 and 1.5 Hz); 7.48 (1 H, dd, J=8.1 and 1.7 Hz); 7.50-7.73 (1 H, m), 7.55 (1 H, d. J=8.1 Hz); 7.64-7.68 (1 H, m); 7.69 (1 H, d, J=1.7 Hz). $^{13}$C-NMR (CDCl$_3$): 27.58; 44.42; 50.70; 80.43; 119.81; 120.80; 121.03; 123.96; 127.59; 127.65; 127.94; 130.72; 139.46; 139.68; 148.02; 150.51. MALDI TOF-MS mass: calculated (M+H$^+$) 473.13 and 475.12; found 473.14 and 475.13.

Example 3

Synthesis of Compound 3

This compound 3 was synthesized from 2-bromofluorene and {2-[2-(2-methoxyethoxy)-ethoxy]ethoxy}-p-toluenesulfonate using a method analogous to the synthesis described in the Example 2. The product was purified by FC (silica gel, first CH$_2$Cl$_2$, then 5% MeOH in CH$_2$Cl$_2$). Yield: 100%. $^1$H-NMR (D$_6$-DMSO): 2.25-2.39 (4 H, m); 2.64-2.71 (4 H, m); 3.04-3.14 (4 H, m); 3.19 (6H, s); 3.22-3.26 (4 H, m); 3.32-3.35 (4 H, m); 3.35-3.39 (4 H, m); 7.33-7.28 (2 H, m); 7.52 (1H, dd, J=8.1 and 1.8 Hz); 7.54-7.57 (1 H, m); 7.76 (1 H, d, J=8.1 Hz); 7.81-7.84 (1 H, m); 7.82 (1 H, d, J=1.8 Hz). $^{13}$C-NMR (D$_6$-DMSO): 38.38; 51.27: 57.39; 66.24; 69.71; 69.43 69.56; 71.11; 120.13; 120.38; 121.65; 123.19; 126.44; 127.29; 127.52; 127.70; 138.83; 139.12; 148.56; 151.57. MALDI TOF-MS mass: calculated (M+H$^+$) 537.19 and 539.18; found 536.91 and 539.73.

Example 4

Synthesis of Compound 4

This compound 4 was synthesized from the compound 2 using a method analogous to the synthesis described in the Example 1. The product was purified by FC (silica gel, first 10% then 20% EtOAc in petroleum ether (b.p. 40-65° C.)). Yield: 100%. $^1$H-NMR (CDCl$_3$): 1.03 (18 H, s); 1.36 (12 H, s); 2.95 (2 H, d, J=14.0 Hz); 2.99 (2 H, d, J=14.0 Hz); 7.32 (1 H, td, J=7.3 and 1.3 Hz); 7.35 (1 H, td, J=7.3 and 1.3 Hz); 7.55-7.58 (1H, m); 7.68 (1 H, d, J=7.5 Hz); 7.69-7.72 (1H, m); 7.81 (1H, dd, J=7.5 and 0.7 Hz); 9.94 (1H, s). $^{13}$C-NMR (CDCl$_3$): 24.93; 28.11; 44.55; 50.56; 80.16; 83.51; 119.04; 120.16; 124.17; 127.64; 127.68; 130.23; 134.44; 134.74; 140.39: 143.47; 147.55; 148.85; 169.32. MALDI TOF-MS mass: calculated (M+H$^+$) 521.31; found 520.99.

Example 5

Synthesis of Compound 5

A mixture of compound 2 (0.48 g, 1.0 mmol), bis(triphenylphosphine)palladium(II) chloride (35 mg, 50 µmol), CuI (10 mg, 50 µmol) in di-isopropylethylamine (1.5 ml) and dry DMF (0.5 ml) was de-aerated with argon. After addition of trimethylsilylacetylene (0.198 ml, 1.4 mmol), the mixture was in microwave synthesizer for 25 min at 120° C. The mixture was dissolved in $Et_2O$ (30 ml), washed with $H_2O$ (3×10 ml) and dried with $Na_2SO_4$. The product was purified by FC (silica gel, 10% EtOAc in petroleum ether (b.p. 40-65° C.)). Yield: 0.47 g (96%). $^1$H-NMR ($D_6$-DMSO): 0.25 (9 H, s), 0.84 (18 H, s); 2.95 (2 H, d, J=13.9 Hz); 3.06 (2H, d, J=13.9 Hz); 7.32 (1 H, td, J=7.3 and 1.3 Hz); 7.35 (1 H, td, J=7.3 and 1.1 Hz); 7.43 (1 H, dd; J=7.8 and 1.1 Hz); 7.57-7.60 (1 H, m); 7.72 (1 H, d, J=1.1 Hz); 7.77 (1 H, d, J=7.8 Hz); 7.79-7.82 (1 H, m). $^{13}$C-NMR ($D_6$-DMSO): −0.12; 26.94; 44.09; 50.56; 79.07; 93.75; 106.26; 119.82; 120.12; 120.20; 124.05; 127.45; 127.48; 127.56; 130.91; 139.78; 141.46; 148.33; 148.56; 168.33. MALDI TOF-MS mass: calculated (M+H$^+$) 491.25; found 491.05.

Example 6

Synthesis of Compound 6

This compound 6 was synthesized from the compound 3 using a method analogous to the synthesis described in the Example 5. The product was purified by FC (silica gel, first $CH_2Cl_2$, then from 1% to 2% MeOH in $CH_2Cl_2$). Yield: 67%. $^1$H-NMR ($D_6$-DMSO): 0.25 (9 H, s), 2.26-2.40 (4 H, m), 2.56-2.67 (4 H, m); 3.03-3.13 (4 H, m); 3.19 (6 H, s); 3.21-3.26 (4 H, m); 3.32-3.35 (4 H, m); 3.35-3.39 (4 H, m); 7.34-7.39 (2 H, m); 7.44 (1 H, dd, J=7.8 and 1.2 Hz); 7.54-7.58 (1 H, m); 7.69 (1 H, s); 7.80 (1 H, d, J=7.8 Hz); 7.81-7.75 (1 H, m). $^{13}$C-NMR ($D_6$-DMSO): —0.13; 38.45; 50.97; 57.92; 66.24; 69.22; 69.42; 69.57; 71.11; 93.94; 106.03; 120.04; 120.38; 120.59; 123.19; 126.42; 127.29; 127.88; 130.91; 139.03; 140.61; 149.20; 149.22. MALDI TOF-MS mass: calculated (M+H$^+$) 555.32; found 555.55.

Example 7

Synthesis of Compound 7

A mixture of compound 5 (0.45 g, 0.92 mmol), tetrabutylammonium fluoride (0.34 g, 1.06 mmol) in $CH_2Cl_2$ (15 ml) under argon was stirred at RT for 1 h. The mixture was washed quickly with 10% citric acid (15 ml), $H_2O$ (2×15 ml) and dried with $Na_2SO_4$. The product was purified by FC (silica gel, 10% EtOAc in petroleum ether (b.p. 40-65° C.)). Yield: 0.35 g (91%). $^1$H-NMR ($D_6$-DMSO): 0.86 (18 H, s); 2.96 (2 H, d, J=13.9 Hz); 3.04 (2 H, d, J=13.9 Hz); 4.16 (1 H, s); 7.32 (1 H, td, J=7.4 and 1.3 Hz); 7.35 (1 H, td, J=7.4 and 1.3 Hz); 7.45 (1 H, dd, J=7.8 and 1.1 Hz); 7.57-7.60 (1 H, m); 7.73 (1 H, d, J=1.1 Hz); 7.77-7.81 (2 H, m). $^{13}$C-NMR ($D_6$-DMSO): 26.96; 44.09; 50.56; 79.07; 80.38; 84.39; 119.77; 119.81; 120.10; 124.07; 127.41; 127.49; 127.57; 131.07; 139.76; 141.37; 148.39; 148.44; 168.30. MALDI TOF-MS mass: calculated (M+H$^+$) 419.22; found 419.12.

Example 8

Synthesis of Compound 8

This compound 8 was synthesized from the compound 6 using a method analogous to the synthesis described in the Example 7. Yield: 99%. $^1$H-NMR ($D_6$-DMSO): 2.26-2.39 (4 H, m); 2.60-2.69 (4 H, m); 3.06-3.12 (4 H, m); 3.19 (6 H, s); 3.22-3.26 (4 H, m); 3.32-3.35 (4 H, m); 3.35-3.38 (4 H, m); 4.20 (1 H, s); 7.33-7.39 (2 H, m); 7.46 (1 H, dd, J=7.8 and 1.2 Hz); 7.55-7.59 (1 H, m); 7.70 (1 H, s); 7.80 (1 H, d, J=7.8 Hz); 7.82-7.86 (1 H, m). $^{13}$C-NMR ($D_6$-DMSO): 38.43; 50.94; 57.92; 66.27; 69.21; 69.42; 69.56; 80.63; 84.19; 120.04; 120.17; 120.37; 123.22; 126.54; 127.28; 127.85; 130.95; 139.03; 140.53; 149.19; 149.21. MALDI TOF-MS mass: calculated (M+H$^+$) 483.28; found 483.14.

Example 9

Synthesis of Compound 9

A mixture of the compound 1 (0.260 g, 0.71 mmol), tetra(tert-butyl) 2,2',2'',2'''-[(4-bromopyridine-2,6-diyl)bis(methylenenitrilo)]tetrakis(acetate) (H. Takalo, et al., 1988, Act a Chem. Scand., Ser B, 42, 614) (0.314 g, 0.41 mmol) and $CsCO_3$ (0.266, 0.80 mmol) in dry DMF (2 ml) was de-aerated with argon. After addition of tetrakis(triphenylphosphine)palladium (11 mg, 9.5 µmol), the mixture was stirred for 20 h at 85° C. The mixture was dissolved in $CH_2Cl_2$ (30 ml), washed with $H_2O$ (3×10 ml) and dried with $Na_2SO_4$. The product was purified by FC (silica gel, 40% EtOAc in petroleum ether (b.p. 40-65° C.) and 0.5% triethylamine). Yield: 0.14 g (39%). $^1$H-NMR ($D_6$-DMSO): 1.40 (36 H, s); 3.47 (8 H, s); 3.98 (4 H, s); 4.02 (2 H, s); 7.37 (1 H, td, J=7.4 and 0.7 Hz); 7.43 (1 H, t, J=7.4 Hz); 7.62 (1 H, d, J=8.0 Hz); 7.76 (1 H, dd, J=7.4 and 0.7 Hz); 7.77 (2 H, s); 7.95 (1 H, s); 7.98 (1 H, d, J=7.4 Hz); 8.05 (1 H, d, J=8.0 Hz). $^{13}$C-NMR ($D_6$-DMSO): 27.68; 36.43; 55.26; 59.22; 80.15; 117.99; 120.39; 120.55; 123.25; 125.17; 125.45; 126.84; 127.19; 136.25; 140.31; 141.97; 143.39; 143.87; 148.18; 159.03; 169.99. MALDI TOF-MS mass: calculated (M+H$^+$) 758.44; found 758.86.

Example 10

Synthesis of Compound 10

A mixture of the compound 4 (78 mg, 0.15 mmol), tetra(tert-butyl) 2,2',2'',2'''-[(4-bromopyridine-2,6-diyl)bis(methylenenitrilo)]tetrakis(acetate) (67 mg, 0.10 mmol), $CsCO_3$ (55 mg, 0.17 mmol) in dry DMF (2 ml) was de-aerated with argon. After addition of tetrakis(triphenylphosphine)palladium (11 mg, 9.5 µmol) and $H_2O$ (9 µl, 0.50 mmol), the mixture was stirred for 2.5 h at 85° C. The mixture was dissolved in $CH_2Cl_2$ (20 ml), washed with $H_2O$ (3×10 ml) and dried with $Na_2SO_4$. The product was purified by FC (silica gel, first 15% EtOAc in petroleum ether (b.p. 40-65° C.), then 40% EtOAc in petroleum ether (b.p. 40-65° C.) and 1% triethylamine). Yield: 76 mg (77%). $^1$H-NMR ($D_6$-DMSO): 0.86 (18 H, s); 1.40 (36 H, s); 3.02 (2 H, d, J=14.0 Hz); 3.07 (2 H, d, J=14.0 Hz); 3.47 (8 H, s); 3.99 (4 H, s); 7.34 (1 H, td, J=7.4 and 1.2 Hz); 7.37 (1 H, td, J=7.4 and 1.1 Hz); 7.61 (1 H, d, J=7.4 Hz); 7.71 (1 H, dd, J=7.9 Hz and 1.2 Hz); 7.74 (2 H, s); 7.85 (1 H, d, J=7.4 Hz); 7.93 (1 H, d, J=7.9 Hz); 7.95 (1 H, d, J=1.2 Hz). $^{13}$C-NMR ($D_6$-DMSO): 26.86; 27.69; 44.07; 50.52; 54.79; 55.27; 59.20; 78.95; 80.10; 118.25; 119.95; 120.15; 122.29; 123.99; 126.02; 127.17; 127.40; 136.49; 139.74; 141.43;

148.37; 148.50; 149.09; 158.81; 168.19; 169.89. MALDI TOF-MS mass: calculated (M+H$^+$) 986.58; found 987.39.

Example 11

Synthesis of Compound 11

A solution of the compound 9 (70 mg, 92 μmmol) in CF$_3$COOH (2.7 ml) was stirred for 2 h at RT. After evaporation without heating, the mixture was triturated with Et$_2$O (10 ml), centrifuged and the product was washed with Et$_2$O (2×5 ml). Yield: 58 mg (83%). $^1$H-NMR (D$_6$-DMSO): 3.67 (8 H, s); 4.07 (2 H, s); 4.32 (4H, s); 7.41 (1 H, t, J=7.3 Hz); 7.46 (1 H, t, J=7.3 Hz); 7.67 (1 H, d, J=7.3 Hz); 7.99 (1 H, d, J=7.8 Hz); 8.04 (1 H, d, J=7.3 Hz); 8.14 (1 H, d, J=7.8 Hz); 8.19 (1 H, s); 8.27 (2 H, s). $^{13}$C-NMR (D$_6$-DMSO): 36.44; 54.94; 56.10; 115.26; 120.10; 120.84; 120.89; 124.17; 125.30; 126.47; 126.96; 127.78; 133.51; 139.91; 144.77; 144.20; 155.27; 157.80; 172.45. MALDI TOF-MS mass: calculated (M+2H$^+$) 535.19; found 535.06.

Example 12

Synthesis of Compound 12

This compound 12 was synthesized from the compound 10 using a method analogous to the synthesis described in the Example 11. Yield: 98%. $^1$H-NMR (D$_6$-DMSO): 3.02 (2 H, d, J=15.4 Hz); 3.16 (2 H, d, J=15.4 Hz); 3.58 (8 H, s); 4.15 (4 H, s); 7.34 (1 H, t, J=7.4 Hz); 7.38 (1 H, t, J=7.4 Hz); 7.63 (1 H, d, J=7.4 Hz); 7.81 (1 H, d, J=7.9 Hz); 7.89 (1 H, d, J=7.4 Hz); 7.91 (2 H, s); 7.97 (1 H, d, J=7.9 Hz); 8.07 (1 H, s). $^{13}$C-NMR (D$_6$-DMSO): 42.00; 49.50; 54.81; 58.11; 118.88; 120.44; 120.57; 122.09; 122.23; 123.71; 126.44; 127.41; 127.59; 135.33; 139.19; 141.67; 149.39; 150.46; 157.73; 171.13; 172.50. MALDI TOF-MS mass: calculated (M+2H$^+$) 651.20; found 651.29.

Example 13

Synthesis of Compound 13

A mixture of the compound 7 (92 mg, 0.22 mmol), tetra(tert-butyl) 2,2',2'',2'''-[(4-bromopyridine-2,6-diyl)bis(methylenenitrilo)]tetrakis(acetate) (135 mg, 0.20 mmol) in dry triethylamine (1 ml) and THF (2 ml) was de-aerated with argon. After addition of bis(triphenylphosphine)palladium (II) chloride (14 mg, 20 μmol), CuI (8 mg, 40 μmol), the mixture was stirred for 20 h at 55° C. After evaporation to dryness, the residue was dissolved in CH$_2$Cl$_2$ (20 ml), washed with H$_2$O (3×10 ml) and dried with Na$_2$SO$_4$. The product was purified by FC (silica gel, from 20% to 30% EtOAc in petroleum ether (b.p. 40-65° C.). Yield: 90 mg (45%). $^1$H-NMR (D$_6$-DMSO): 0.86 (18 H, s); 1.42 (36 H, s); 2.97 (2 H, d, J=13.9 Hz); 3.09 (2 H, d, J=13.9 Hz); 3.44 (8 H, s); 3.92 (4 H, s); 7.35 (1 H, td, J=7.2 and 1.3 Hz); 7.38 (1 H, td, J=7.2 and 1.2 Hz); 7.55-7.58 (1 H, m); 7.57 (2 H, s); 7.59-7.64 (2 H, m); 7.83-7.86 (2 H, m); 7.87 (1 H, d, J=7.9 Hz). $^{13}$C-NMR (D$_6$-DMSO): 26.96; 27.81; 44.10; 50.61; 55.54; 59.18; 79.09; 80.34; 87.29; 93.90; 119.25; 120.09; 120.26; 122.06; 124.06; 127.57; 127.59; 127.67; 130.99; 131.14; 139.68; 142.10; 148.59; 148.65; 159.27; 168.27; 170.05. MALDI TOF-MS mass: calculated (M+H$^+$) 1010.58; found 1011.07.

Example 14

Synthesis of Compound 14

This compound 14 was synthesized from the compound 13 using a method analogous to the synthesis described in the Example 11. Yield: 87%. $^1$H-NMR (D$_6$-DMSO): 3.04 (2 H, d, J=15.5 Hz); 3.09 (2 H, d, J=15.5 Hz); 3.51 (8 H, s); 3.97 (4 H, s); 7.34 (1 H, td, J=7.3 and 1.2 Hz); 7.37 (1 H, td, J=7.3 and 1.1 Hz); 7.58 (2 H, s); 7.61 (1 H, dd, J=7.6 and 1.2 Hz); 7.61-7.64 (1 H, m); 7.86 (1 H, d, J=7.3 Hz); 7.89 (1 H, d, J=1.2 Hz); 7.89 (1 H, d, J=7.6 Hz). $^{13}$C-NMR (D$_6$-DMSO): 41.90; 49.54; 54.55; 58.98; 87.36; 94.17; 119.32; 120.41; 120.63; 122.31; 123.70; 127.09; 127.91; 131.29; 131.37; 139.12; 141.56; 149.63; 149.75; 159.24; 171.27; 172.42. MALDI TOF-MS mass: calculated (M+H$^+$) 675.20; found 675.16.

EXAMPLE 15

Synthesis of Compound 15

A mixture of 3-bromo-9H-carbazole (0.25 g, 1.0 mmol), acetic anhydride (0.95 ml, 10 mmol) in triethylamine (5 ml) and CH$_2$Cl$_2$ (20 ml) was stirred for 22 h at RT. After addition of water (20 ml), the mixture was stirred for 15 min. The organic phase was separated and washed with 5% NaHCO$_3$ (20 ml), water (2 x 20 ml) was dried with Na$_2$SO$_4$. Yield: 0.29 g (100%).

$^1$H-NMR (D$_6$-DMSO): 2.89 (3 H, s); 7.35 (1 H, t, J=7.3 Hz); 7.57 (1 H, td, J=7.3 and 1.2 Hz); 7.66 (1 H, dd, J=8.8 and 2.1 Hz); 8.21 (1 H, d, J=8.8 Hz); 8.23-8.28 (2 H, m); 8.47 (1 H, d, J=2.1 Hz). $^{13}$C-NMR (D$_6$-DMSO): 27.35; 115.91; 116.07; 118.14; 120.68; 122.72; 123.64; 124.35; 127.62, 128.10; 129.68; 136.94; 138.22; 170.42. MALDI TOF-MS mass: calculated (M+H$^+$) 287.99 and 289.99; found 288.03 and 288.83.

Example 16

Synthesis of Compound 16

Bromoacetyl chloride (100 μl, 1.2 mmol) was added into a mixture of di(tert-butyl) iminobis(acetate) (0.245 g, 1.0 mmol), dry K$_2$CO$_3$ (0.691 g, 5.0 mmol) and dry MeCN (5 ml) at ice-bath, the mixture was stirred for 30 min at 0° C. and for 2 h at RT. After addition of CH$_2$Cl$_2$ (40 ml), the mixture was washed with water (2×20 ml) and dried with Na$_2$SO$_4$. Yield: 0.34 g (93%). $^1$H-NMR (D$_6$-DMSO): 1.40 (9 H, s); 1.43 (9 H, s); 3.94 (2 H, s); 4.14 (2 H, s); 4.21 (2 H, s). $^{13}$C-NMR (D$_6$-DMSO): 27.33; 27.74; 49.39; 51.14; 80.89; 81.57; 166.92; 167.60; 167.90. MALDI TOF-MS mass: calculated (M+H$^+$) 366.08 and 367.08; found 367.78 and 368.80.

Example 17

Synthesis of Compound 17

A mixture of 3-bromo-9H-carbazole (0.22 g, 0.9 mmol), compound 16 (0.66 g, 1.8 mmol), dry K$_2$CO$_3$ (0.25 g, 1.8 mmol) and dry MeCN (10 ml) was refluxed for 48 h. After addition of CH$_2$Cl$_2$ (40 ml), the mixture was washed with water (2×20 ml) and dried with Na$_2$SO$_4$. The product was purified by FC (silica gel, from 10% to 30% EtOAc in petroleum ether (b.p. 40-65° C.). Yield: 0.41 g (85%). $^1$H-NMR (D$_6$-DMSO): 1.37 (9 H, s); 1.51 (9 H, s); 3.97 (2

H, s); 4.44 (2 H, s); 5.32 (2 H, s); 7.23 (1 H, td, J=7.8 and 0.7 Hz); 7.37 (1 H, d, J=8.7 Hz); 7.40 (1 H, d, J=7.8 Hz); 7.47 (1 H, td, J=7.8 and 1.0 Hz); 7.56 (1 H, dd, J=8.7 and 2.0 Hz); 8.22 (1 H, d, J=7.8 Hz); 8.40 (1 H, d, J=2.0 Hz). $^{13}$C-NMR (D$_6$-DMSO): 27.73; 27.80; 27.80; 43.87; 49.52; 50.17; 80.86; 81.94; 109.35; 111.13; 111.15; 119.47; 120.81; 121.33; 122.84; 124.28; 126.46; 127.97; 139.55; 141.11; 167.76; 168.58. MALDI TOF-MS mass: calculated (M+H$^+$) 531.14 and 533.14; found 530.94 and 532.90

Example 18

Synthesis of Compound 18

This compound 18 was synthesized from the compound 15 using a method analogous to the synthesis described in the Example 1. The product was purified by FC (silica gel, from 10% to 30% EtOAc in petroleum ether (b.p. 40-65° C.)). Yield: 98%. $^1$H-NMR (D$_6$-DMSO): 1.35 (12 H, s); 2.90 (3 H, s); 7.43 (1 H, t, J=7.4 Hz); 7.53 (1 H, td, J=7.4 and 0.9 Hz); 7.82 (1 H, d, J=8.4 Hz); 8.25 (1 H, d, J=8.4 Hz); 8.27-8.31 (2 H, m); 8.47 (1 H, s). $^{13}$C-NMR (D$_6$-DMSO): 24.64; 27.46; 83.67; 115.62; 116.04; 120.26; 123.67; 125.12; 125.31; 126.34; 127.42; 133.49; 138.06; 140.14; 170.58. MALDI TOF-MS mass: calculated (M+H$^+$) 336.17; found 337.04

Example 19

Synthesis of Compound 19

This compound 19 was synthesized from 3-bromodibenzofuran (Li, W., et al., 2009, J. Med. Chem., 52, 1799) using a method analogous to the synthesis described in the Example 1. The product was purified by FC (silica gel, 5% EtOAc in petroleum ether (b.p. 40-65° C.)). Yield: 48%. $^1$H-NMR (D$_6$-DMSO): 1.35 (12H, s); 7.42 (1 H, td, J=7.7 and 0.6 Hz); 7.54 (1 H, td, J=7.7 and 1.2 Hz); 7.70 (1 H, d, J=8.2 Hz); 7.71 (1 H, d, J=8.2 Hz); 7.83 (1 H, dd, J=7.7 and 1.2 Hz); 8.27 (1 H, dd, J=7.7 and 0.6 Hz); 8.49 (1 H, s). $^{13}$C-NMR (D$_6$-DMSO): 24.76; 83.81; 111.33; 111.64; 121.51; 123.28; 123.39; 123.49; 127.77; 127.83; 133.80; 155.51; 157.63. MALDI TOF-MS mass: calculated (M+H$^+$) 295.14; found 295.05.

Example 20

Synthesis of Compound 20

This compound 20 was synthesized from 3-bromodibenzothiophene (Tedjamulia, M. L., et al., 1983, J. Heterocyclic Chem., 20, 1485) using a method analogous to the synthesis described in the Example 1. The product was purified by FC (silica gel, CH$_2$Cl$_2$). Yield: 45%. $^1$H-NMR (CDCl$_3$): 1.40 (12 H, s); 7.42-7.48 (2 H, m); 7.82-7.90 (3 H, m); 8.22-8.27 (1 H, m); 8.62 (1 H, s). $^{13}$C-NMR (CDCl$_3$): 24.93; 83.96; 121.84; 122.12; 122.72; 124.46; 126.68; 128.27; 132.55; 135.10; 135.59; 139.17; 142.76. MALDI TOF-MS mass: calculated (M+H$^+$) 311.12; found 311.18.

Example 21

Synthesis of Compound 21

This compound 21 was synthesized from 2-bromo-9-fluorenone using a method analogous to the synthesis described in the Example 1. The product was purified by FC (silica gel, 10% EtOAc in petroleum ether (b.p. 40-65° C.)). Yield: 88%. $^1$H-NMR (D$_6$-DMSO): 1.32 (12H, s); 7.43 (1 H, td; J=7.4 and 0.8 Hz); 7.65 (1 H, d, J=7.4 Hz); 7.64 (1 H, td, J=7.4 and 1.0 Hz); 7.81 (1 H, s); 7.83 (1 H, d, J=7.4 Hz); 7.85 (1 H, dd, J=7.4 and 0.8 Hz); 7.90 (1 H, dd, J=7.4 and 1.0 Hz). $^{13}$C-NMR (D$_6$-DMSO): 24.69; 84.09; 120.82; 121.72; 123.99; 129.01; 129.76; 130.10; 132.68; 133.53; 135.43; 141.54; 143.55; 146.59; 192.88. MALDI TOF-MS mass: calculated (M+H$^+$) 307.14; found 307.93.

Example 22

Synthesis of Compound 22

This compound 22 was synthesized from the compound 17 using a method analogous to the synthesis described in the Example 1. The product was purified by FC (silica gel, 30% EtOAc in petroleum ether (b.p. 40-65° C.)). Yield: 91%. $^1$H-NMR (D$_6$-DMSO): 1.34 (12 H, s); 1.38 (9 H, s); 1.52 (9 H, s); 3.89 (2 H, s); 4.46 (2 H, s); 5.32 (2 H, s); 7.23 (1 H, td, J=7.5 and 0.8 Hz); 7.39 (1 H, d, J=8.0 Hz); 7.40 (1 H, d, J=8.0 Hz); 7.44 (1 H, td, J=7.5 and 0.9 Hz); 7.73 (1 H, dd, J=7.5 and 0.9 Hz); 8.24 (1 H, d=7.5 Hz); 8.48 (1 H, s). $^{13}$C-NMR (D$_6$-DMSO): 24.78; 27.73; 27.80; 43.80; 49.54; 50.20; 80.85; 81.93; 83.38; 108.64; 109.18; 119.57; 120.41; 122.11; 122.35; 125.82; 127.16; 128.11; 131.73; 140.85; 142.91; 167.78; 167.79; 168.60. MALDI TOF-MS mass: calculated (M+H$^+$) 579.32; found 579.23.

Example 23

Synthesis of Compound 23

A mixture of the compound 18 (0.17 g, 0.50 mmol), tetra(tert-butyl) 2,2',2'',2'''-[(4-bromopyridine-2,6-diyl)bis(methylenenitrilo)]tetrakis(acetate) (0.22 g, 0.33 mmol), CsCO$_3$ (0.18 g, 0.56 mmol) in dry DMF (1.4 ml) and 1,2-ethanediol (1.4 ml) was de-aerated with argon. After addition of tetrakis(triphenylphosphine)palladium (8 mg, 6.6 μmol), the mixture was stirred for 1 h at 85° C. The mixture was dissolved in CH$_2$Cl$_2$ (30 ml), washed with H$_2$O (3×10 ml) and dried with Na$_2$SO$_4$. The product was purified by FC (silica gel, first from 40% to 50% EtOAc in petroleum ether (b.p. 40-65° C.), then 50% EtOAc in petroleum ether (b.p. 40-65° C.) including 10% triethylamine). Yield: 80 mg (32%). $^1$H-NMR (D$_6$-DMSO): 1.40 (36 H, s); 3.49 (8 H, s); 3.99 (4 H, s); 7.21 (1 H, td, J=7.7 and 0.8 Hz); 7.43 (1 H, td, J=7.7 and 1.0 Hz); 7.53 (1 H, d, J=7.7 Hz); 7.61 (1 H, d, J=8.5 Hz); 7.77 (1 H, dd, J=8.5 and 1.7 Hz); 7.82 (2 H, s); 8.18 (1 H, d, J=7.7 Hz); 8.52 (1 H, s). $^{13}$C-NMR (D$_6$-DMSO): 27.68; 55.28; 59.26; 80.13; 111.21; 111.41; 118.00; 118.34; 118.86; 120.09; 122.29; 122.94; 124.27; 125.95; 128.18; 140.12; 140.18; 149.03; 158.72; 170.02. MALDI TOF-MS mass: calculated (M+H$^+$) 759.43; found 760.28.

Example 24

Synthesis of Compound 24

This compound 24 was synthesized from the compound 19 using a method analogous to the synthesis described in the Example 10. The product was purified by FC (silica gel, from 20% to 40% EtOAc in petroleum ether (b.p. 40-65° C.)). Yield: 72%. $^1$H-NMR (D$_6$-DMSO): 1.39 (36 H, s); 3.50 (8 H, s); 4.01 (4 H, s); 7.46 (1 H, td, J=7.8 and 0.6 Hz); 7.58 (1 H, td, J=7.8 and 1.3 Hz); 7.76 (1 H, d, J=7.8 Hz); 8.81 (2 H, s); 7.84-7.87 (2 H, m); 8.21 (1 H, dd, J=7.8 and 0.6 Hz);

8.51 (1 H, s). $^{13}$C-NMR (D$_6$-DMSO): 27.79; 55.46; 59.42; 80.26; 111.92; 112.31; 118.65; 119.48; 121.26; 123.34; 123.42; 124.43; 126.49; 128.11; 133.45; 148.22; 155.90; 156.04; 159.15; 170.11. MALDI TOF-MS mass: calculated (M+H$^+$) 760.41; found 760.98.

Example 25

Synthesis of Compound 25

This compound 25 was synthesized from the compound 20 using a method analogous to the synthesis described in the Example 10. The product was purified by FC (silica gel, 20% EtOAc in petroleum ether (b.p. 40-65° C.)). Yield: 68%. $^1$H-NMR (CDCl$_3$): 1.46 (36 H, s); 3.56 (8 H, s); 4.14 (4 H, s); 7.48 (1 H, td, J=3.6 and 0.6 Hz); 7.49 (1 H, td, J=3.6 and 0.4 Hz); 7.84 (1 H, dd, J=8.3 and 1.2 Hz); 7.86-7.89 (1 H, m), 7.92 (1 H, d, J=8.3 Hz); 7.96 (2 H, s); 8.32-8.37 (1 H, m); 8.60 (1 H, d, J=1.2 Hz). $^{13}$C-NMR (CDCl$_3$): 28.20; 55.98; 60.19; 81.00; 118.75; 120.27; 122.02; 122.85; 123.08; 124.46; 125.78; 126.97; 135.07; 135.52; 136.23; 139.84; 140.03; 149.18; 159.57; 170.66. MALDI TOF-MS mass: calculated (M+H$^+$) 776.39; found 776.94.

Example 26

Synthesis of Compound 26

This compound 26 was synthesized from the compound 23 using a method analogous to the synthesis described in the Example 11. Yield: 73%. $^1$H-NMR (D$_6$-DMSO): 3.61 (8 H, s); 4.20 (4 H, s); 7.25 (1 H, td, J=7.7 and 0.7 Hz); 7.46 (1 H, td, J=7.7 and 1.1 Hz); 7.56 (1 H, d, J=7.7 Hz); 7.65 (1 H, d, J=8.2 Hz); 7.93 (1 H, dd, J=7.7 and 1.1 Hz); 8.11 (2 H, s); 8.23 (1 H, d, J=8.2 Hz); 8.72 (1 H, s); 11.61 (1 H, s). $^{13}$C-NMR (D$_6$-DMSO): 54.88; 57.43; 111.34; 111.67; 118.68; 119.16; 120.37; 122.31; 123.15; 124.07; 125.67; 126.22; 140.26; 140.83; 152.36; 156.67; 172.62. MALDI TOF-MS mass: calculated (M+2H$^+$) 536.18; found 536.21.

Example 27

Synthesis of Compound 27

This compound 27 was synthesized from the compound 24 using a method analogous to the synthesis described in the Example 11. Yield: 70%. $^1$H-NMR (D$_6$-DMSO): 3.64 (8 H, S); 4.23 (4 H, s); 7.49 (1H, t, J=7.7 Hz); 7.60 (1 H, td, J=7.7 and 1.2 Hz); 7.77 (1 H, d, J=7.7 Hz); 7.91 (1 H, d, J=8.6 Hz); 8.01 (1 H, dd, J=8.6 and 1.5 Hz); 8.11 (2H, s); 8.25 (1 H, d, J=7.7 Hz); 8.68 (1 H, d, J=1.5 Hz). $^{13}$C-NMR (D$_6$-DMSO): 54.82; 57.56; 111.81; 112.43; 119.48; 120.06; 121.29; 123.05; 123.40; 124.50; 126.74; 128.16; 131.62; 150.86; 155.95; 156.34; 157.07; 172.37. MALDI TOF-MS mass: calculated (M+2H$^+$) 537.16; found 536.84.

Example 28

Synthesis of Compound 28

This compound 28 was synthesized from the compound 25 using a method analogous to the synthesis described in the Example 11. Yield: 67%. $^1$H-NMR (D$_6$-DMSO): 3.63 (8 H, s); 4.24 (4 H, s); 7.59 (1 H, t, J=3.5 Hz); 7.61 (1 H, t, J=3,5 Hz); 8.00 (1 h, dd, J=8.4 and 1.5 Hz); 8.08-8.12 (1 H, m); 8.19 (2 H, s); 8.24 (1 H, d, J=8.4 Hz); 8.50-8.55 (1 H, m); 8.87 (1 H, d, J=1.5 Hz). $^{13}$C-NMR (D$_6$-DMSO): 55.50; 58.26; 119.99; 121.11; 122.84; 123.78; 124.50; 125.52; 126.14; 128.17; 133.55; 135.23; 136.43; 139.65; 141.09; 157.82; 158.51, 173.10. MALDI TOF-MS mass: calculated (M+2H$^+$) 553.16; found 552.80.

Example 29

Synthesis of Compound 29

This compound 29 was synthesized from the compound 22 using a method analogous to the synthesis described in the Example 23. Reaction time was 6 h. The product was purified by FC (silica gel, from 20% to 50% EtOAc in petroleum ether (b.p. 40-65° C.)). Yield: 55%. $^1$H-NMR (D$_6$-DMSO): 1.39 (36 H, s); 3.48 (8 H, s); 3.98 (4 H, s); 7.44 (1 H, td, J=7.4 and 0.7 Hz); 7.66 (1 H, td, J=7.4 and 1.0 Hz); 7.67 (1 H, d, J=7.4 Hz); 7.78 (2 H, s); 7.89 (1 H, dd, J=7.4 and 1.0 Hz); 7.93 (1 H, s); 7.97-7.99 (2 H, m). $^{13}$C-NMR (D$_6$-DMSO): 27.67; 55.38; 59.22; 80.19; 117.88; 121.56; 121.73; 121.87; 124.04; 129.76; 133.38; 133.49; 134.17; 135.50; 138.89; 143.28; 144.27; 146.69; 159.28; 170.00; 192.45: MALDI TOF-MS mass: calculated (M+H$^+$) 772.41; found 773.03.

Example 30

Synthesis of Compound 30

This compound 30 was synthesized from the compound 29 using a method analogous to the synthesis described in the Example 11. Yield: 77%. $^1$H-NMR (D$_6$-DMSO): 3.61 (8 H, s); 4.16 (4 h, s); 7.45 (1 H, td, J=7.6 and 0.7 Hz); 7.65-7.70 (2 H, m); 7.91 (1 H, d, J=7.6 Hz), 8.00 (1 H, d, J=7.8 Hz); 8.02 (2 H, s); 8.04 (1 H, d, J=1.4 Hz); 8.08 (1 H, dd, J=7.8 and 1.4 Hz). $^{13}$C-NMR (D$_6$-DMSO): 54.78; 58.00; 119.02; 121.70; 121.96; 122.16; 124.08; 129.93; 133.55; 133.84; 134.25; 135.53; 137.79; 139.87; 143.17; 144.92; 157.76; 172.35; 192.40. MALDI TOF-MS mass: calculated (M+2H$^+$) 549.16; found 549.37.

Example 36

Synthesis of Compound 36

A mixture of 7-iodo-2-nitrofluorene (1.7 g, 5 mmol; Marhevka, V.C., et al., 1985, J. Med. Chem., 28, 18.), SnCl$_2$×2H$_2$O (5.6 g, 25 mmol) in dry EtOH (100 ml) was refluxed for 18 h. The cold mixture was poured to H$_2$O (70 ml), neutralized with solid NaHCO$_3$, extracted with CH$_2$Cl$_2$ (200 ml and 2×100 ml) and dried with Na$_2$SO$_4$. Yield: 1.5 g (97%). %. $^1$H-NMR (CDCl$_3$): 3.76 (2 +2 H, s); 6.89 (1 H, dd, J=8.1 and 2.1 Hz); 6.84 (1 H, s); 7.36 (1 H, d, J=8.0 Hz); 7.52 (1 H, d, J=8.1 Hz); 7.61 (1 H, d, J=8.0 Hz); 7.78 (1 H, s); $^{13}$C-NMR (CDCl$_3$): 36.52; 89.52; 111.52; 114.10; 120.24; 120.87; 131.94; 133.79; 135.58; 141.82; 144.60; 144.73; 146.33. MALDI TOF-MS mass: calculated (M+H$^+$) 307.99; found 307.89.

Example 37

Synthesis of Compound 37

This compound 37 was synthesized from the compound 36 using a method analogous to the synthesis described in the Example 13. Reaction time 3 h. The product was purified by FC (silica gel, from 50% EtOAc in petroleum ether (b.p. 40-65° C.)). Yield: 99%. $^1$H-NMR (CDCl$_3$): 0.26 (9 H, s), 3.76 (2+2 H, s); 6.69 (1 H, dd, J=8.0 and 2.0 Hz); 6.84 (1 H, s); 7.43 (1 H, d, J=8.0 Hz); 7.53 (2+2 H, d, J=8.0 Hz); 7.56 (1 H, s). $^{13}$C-NMR (CDCl$_3$): 0.10; 36.56; 93.25; 106.30; 111.61; 114.11; 118.27; 119.28; 121.10; 128.26; 130.88; 132.30; 142.03; 142.61; 145.69, 146.25. MALDI TOF-MS mass: calculated (M+H$^+$) 278.13; found 278.12.

Example 38

Synthesis of Compound 38

This compound 38 was synthesized from the compound 37 using a method analogous to the synthesis described in the Example 7. Yield: 95%. $^1$H-NMR (CDCl$_3$): 3.07 (1 H, s); 3.78 (2+2 H, s); 6.70 (1 H, dd, J=8.1 and 2.1 Hz); 6.85 (1 H, s); 7.45 (1 H, d, J=7.8 Hz); 7.54 (1 H, d, J=8.1 Hz); 7.55 (1 H, d, J=7.8 Hz); 7.57 (1 H, s). $^{13}$C-NMR (CDCl$_3$): 36.58; 76.37; 84.74; 111.60; 114.12; 118.19; 118.34; 121.15; 128.39; 131.03; 132.16; 142.13; 142.92; 145.66; 146.34. MALDI TOF-MS mass: calculated (M+H$^+$) 206.09; found 205.82.

Example 39

Synthesis of Compound 39

This compound 39 was synthesized from the compound 38 using a method analogous to the synthesis described in the Example 13. The product was purified by FC (silica gel, from 30% to 50% EtOAc in petroleum ether (b.p. 40-65° C.)). Yield: 51%. $^1$H-NMR (D$_6$-DMSO): 1.42 (36 H, s); 3.44 (8 H, s); 3.78 (2 H, s); 3.91 (4 H, s); 6.61 (1 H, dd, J=8.2 and 1.6 Hz); 6.78 (1 H, s); 7.48 (1 H, d, J=7.8 Hz); 7.53 (2 H, s); 7.57 (1 H, d, J=8.2 Hz); 7.62 (1 H, s); 7.85 (1 H, d, J=7.8 Hz). $^{13}$C-NMR (D$_6$-DMSO): 28.26; 36.49; 55.94; 55.94; 80.79; 87.22; 94.95; 110.50; 113.52; 116.77; 118.64; 121.85; 122.46; 128.26; 128.98; 131.03; 131.88; 142.49; 144.31; 146.00; 149.81; 159.58; 170.51. MALDI TOF-MS mass: calculated (M+H$^+$) 797.44; found 797.43.

Example 40

Synthesis of Compound 40

This compound 40 was synthesized from the compound 39 using a method analogous to the synthesis described in the Example 11. Yield: 91%. $^1$H-NMR (D$_6$-DMSO): 3.60 (8 H, s); 3.88 (2 H, s); 4.10 (4 H, s); 6.86 (1 H, d, J=7.9 Hz); 7.03 (1 H, s); 7.59 (1H, d, J=7.9 Hz); 7.68 (2 H, s); 7.73 (1 H, d, J=7.9 Hz); 7.74 (1 H, s); 7.79 (1 H, d, J=7.9 Hz). $^{13}$C-NMR (D$_6$-DMSO): 36.02; 54.45; 57.91; 86.63; 96.30; 112.90; 115.61; 116.79; 118.00; 121.66; 123.13; 128.13; 128.15; 130.85; 131.70; 133.14; 142.44; 143.36; 145.46; 145.53; 157.39; 171.96. MALDI TOF-MS mass: calculated (M+2H$^+$) 574.21; found 574.09.

Example 41

Synthesis of Compound 41

The tetraacid 40 (44 mg, 48 μmol) was dissolved in H$_2$O (0.78 ml) and the pH was adjusted to 6.5 with solid NaHCO$_3$. EuCl$_{3\times 6}$H$_2$O (20 mg, 55 μmol) in H$_2$O (0.39 ml) was added within 15 min and the pH maintained at 5-7 with solid NaHCO$_3$. After stirring for 1.5 h, the pH was raised to 8.5 with 1M NaOH, the precipitate centrifuged off, the supernatant triturated with acetone, the precipitate centrifuged and washed with acetone. The product was used in the next step without further purification.

Example 42

Synthesis of Compound 42

An aq. solution (1.3 ml) of amino chelate 41 (48 μmol) was added within 10 min to a mixture of SCCl$_2$ (26 μl, 0.34 mmol), NaHCO$_3$ (40 mg, 0.48 mmol) and CHCl$_3$ (1.3 ml). After stirring for 30 min, the H$_2$O phase was washed with CHCl$_3$ (3×1.3 ml), triturated with acetone, the precipitate centrifuged and washed with acetone. MALDI TOF-MS mass: calculated (M+H$^+$) 786.03; found 787.50. R$_f$(HPLC): 30.9 min. UV (HPLC): 346 and 360 nm.

Example 43

Synthesis of Compound 43

A mixture of compound 7 (0.23 g, 0.55 mmol), tetra(tert-butyl) 2,2',2",2'''-{[(4-aminophenyl) ethylimino] bis(m ethylene)bis(4-bromopyridine-6,2-diyl)bis(methylene-nitrilo)}tetrakis(acetate) (Takalo, H., et al., 1996, Helv. Chim.Acta., 79, 789) (0.23 g, 0.23 mmol) in dry triethylamine (2 ml) and dry THF (4 ml) was de-aerated with argon. After addition of bis(triphenylphosphine)palladium(II) chloride (10 mg, 14 μmol), CuI (5.3 mg, 28 μmol), the mixture was stirred for 22 h at 55° C. After evaporation to dryness, the residue was dissolved in CH$_2$Cl$_2$ (30 ml), washed with H$_2$O (3×10 ml) and dried with Na$_2$SO$_4$. The product was purified by FC (silica gel, 5% MeOH in CH$_2$Cl$_2$). Yield: 0.25 g (65%). $^1$H-NMR (D$_6$-DMSO): 0.85 (36 H, s); 1.40 (36 H, s); 2.64-2.71 (4 H, m); 2.87 (4 H, d, J=13.9 Hz); 3.08 (4 H, d, J=13.9 Hz); 3.45 (8 H, s); 3.87 (4 H, s); 3.95 (4 h, s); 4.77 (2 H, s); 6.56 (2 H, d, J=8.2 Hz); 6.81 (2 H, d, J=8.2 Hz); 7.32-7.39 (4 H, m); 7.49 (2 H, s); 7.56-7.65 (6 H, m); 7.78-7.83 (4 H, m); 7.88 (2 H, s). $^{13}$C-NMR (D$_6$-DMSO): 26.84; 27.68; 32.17; 43.95; 50.47; 55.42; 56.13; 59.10; 59.20; 78.98; 80.19; 87.22; 93.83; 113.90; 119.22; 120.02; 120.10; 122.06; 122.19; 123.98; 126.94; 127.47; 127.54; 128.80; 130.93; 131.02; 131.91; 139.53; 141.88; 146.37; 148.46; 148.53; 159.10; 159.19; 168.17; 169.91. MALDI TOF-MS mass: calculated (M+H') 1666.91; found 1665.47.

Example 44

Synthesis of Compound 44

This compound 44 was synthesized from the compound 8 using a method analogous to the synthesis described in the Example 43. The product was purified by FC (silica gel, from CH$_2$Cl$_2$ to 10% MeOH in CH$_2$Cl$_2$). Yield: 44%. $^1$H-NMR (D$_6$-DMSO): 1.40 (36 H, s); 2.26-2.41 (8 H, m); 2.61-2.74 (4+8 H, m); 3.00-3.10 (8 H, m); 3.16 (12 H, s); 3.19-3.23 (8 H, m); 3.29-3.32 (8 H, m); 3.32-3.36 (8 H, m); 3.44 (8 H, s); 3.85 (4 H, s); 3.95 (4 H, s); 4.74 (2 H, s); 6.47 (2 H, d, J=8.1 Hz); 6.81 (2 H, d, J=8.1 Hz); 7.32-7.42 (4 H, m); 7.50 (2 H, s); 7.53-7.61 (6 H, m); 7.72-7.79 (4 H. m); 7.83 (2 H, s). $^{13}$C-NMR (D$_6$-DMSO): 27.65; 32.12; 38.44; 51.05; 55.33; 56.33; 57.88; 59.06; 59.33; 66.26; 69.18; 69.41; 69.54; 71.09; 80.18; 87.49; 93.74; 113.89; 119.76; 120.19; 120.42; 121.99; 122.30; 123.30; 126.58; 126.90; 127.33; 128.06; 128.79; 129.53; 130.93; 131.06; 138.90; 141.08; 149.36; 149.42; 159.02; 159.30; 169.87. MALDI TOF-MS mass: calculated (M+H$^+$) 1795.02; found 1794.46.

Example 45

Synthesis of Compound 45

A solution of the compound 43 (130 mg, 78 μmol) in $CF_3COOH$ (2.3 ml) was stirred for 2 h at RT. After evaporation without heating, the mixture was triturated with $Et_2O$ (10 ml), centrifuged and the product was washed with $Et_2O$ (5×5 ml). Yield: 105 mg (86%). $^1H$-NMR ($D_6$-DMSO): 2.94-3.14 (2+8 H, m); 3.28-3.37 (2 H, m); 3.56 (8 H, s); 4.07 (4 H, s); 4.59 (4 H, s); 6.80 (2 H, d, J=7.6 Hz); 7.05 (2 H, d, J=7.6 Hz); 7.34 (2 H, t, J=7.4 Hz); 7.38 (2 H, t, J=7.0 Hz); 7.60 (2 H, d, J=7.9 Hz); 7.63 (2 H, d, J=7.0 Hz); 7.65 (2 H, s); 7.79 (2 H, s); 7.85 (2 H, d, J=7.4 Hz); 7.87 (2 H, d, J=7.9 Hz); 7.89 (2 H, s). $^{13}C$-NMR ($D_6$-DMSO): 29.26; 41.73; 49.42; 54.41; 54.96; 56.61; 58.99; 86.59; 95.20;117.30; 118.92; 120.33; 120.54; 123.61; 123.93; 124.51; 126.97; 127.47; 127.89; 129.44; 131.30; 131.86; 138.92; 141.69; 149.49; 149.69; 151.15; 157.70; 157.96; 160.11; 171.12; 172.24. MALDI TOF-MS mass: calculated ($M+H^+$) 1217.42; found 1217.63.

Example 46

Synthesis of Compound 46

This compound 46 was synthesized from the compound 44 using a method analogous to the synthesis described in the Example 45. Yield: 100%. $^1H$-NMR ($D_6$-DMSO): 2.30-2.42 (8H, m); 2.62-2.72 (8 H, m); 3.03-3.13 (8 +2 H, m); 3.14-3.19 (2 H, m); 3.17 (12 H, s); 3.20-3.26 (8 H, m); 3.29-3.36 (8 H, m); 3.36-3.39 (8 H, m); 3.56 (8 H, s); 4.09 (4 H, s); 4.59 (4 H, s); 6.94 (2 H, d, J=6.7 Hz); 7.14 (2 H, d, J=6.7 Hz); 7.36-7.42 (4 H, m); 7.56-7.62 (4 H, m); 7.64 (2 H, s); 7.79 (2 H, s), 7.83-7.89 (6 H, m). $^{13}C$-NMR ($D_6$-DMSO): 29.38; 38.44; 51.09; 54.39; 55.12; 56.64; 57.89; 58.95; 66.26; 69.20; 69.41; 69.55; 71.09; 86.80; 95.20; 118.78; 119.30; 120.30; 120.56; 123.34; 123.94; 124.51; 126.66; 127.38; 128.18; 129.58; 131.18; 131.98; 138.87; 141.48; 149.36; 149.53; 151.15; 157.88; 158.14; 159.97; 172.16. MALDI TOF-MS mass: calculated ($M+H^+$) 1569.77; found 1569.33.

Example 47

Synthesis of Compound 47

The compound 45 (94 mg, 60 μmol) was dissolved in $H_2O$ (0.96 ml) and the pH adjusted to 6.5 with solid $NaHCO_3$. $EuCl_3 \times 6H_2O$ (25 mg, 69 μmol) in $H_2O$ (0.48 ml) was added within 15 min and the pH maintained at 5-7 with solid $NaHCO_3$. After stirring for 2.5 h at RT, the pH was raised to 8.5 with 1 M NaOH, the precipitate was centrifuged off and the supernatant was extracted with phenol (ca 0.75 g). The phenol phase was treated with $H_2O$ (0.5 ml) and $Et_2O$ (10 ml) and the aqueous phase was washed with $Et_2O$ (2×10 ml). After addition of NaCl (17.5 mg, 0.3 mmol), the mixture was triturated with acetone, the precipitate was centrifuged and washed with acetone. The product was used for the next step without further purification. MALDI TOF-MS mass: calculated ($M+H^+$) 1477.22; found 1477.78. $R_f$(HPLC): 22.0 min. UV (HPLC): 345 nm.

Example 48

Synthesis of Compound 48

This compound 48 was synthesized from the compound 46 using a method analogous to the synthesis described in the Example 47. After phenol extraction the aqueous phase was evaporated to dryness, as the product was soluble in acetone. The product was used for the next step without further purification. MALDI TOF-MS mass: calculated ($M+H^+$) 1741.65; found 1741.50.

Example 49

Synthesis of Compound 49

This compound 49 was synthesized from the compound 47 using a method analogous to the synthesis described in the Example 42. After 0.5 h reaction time, the mixture was washed with $Et_2O$ (2×5 ml) and the aqueous solution was evaporated to dryness. MALDI TOF-MS mass (negative mode): calculated 1518.17; found 1518.78. $R_f$(HPLC): 34.6 min. UV (HPLC): 350 nm.

Example 50

Synthesis of Compound 50

This compound 50 was synthesized from the compound 48 using a method analogous to the synthesis described in the Example 42. MALDI TOF-MS mass: calculated ($M+H^+$) 1783.68; found 1783.59. $R_f$(HPLC): 24.9 min. UV (HPLC): 340 and 349 nm.

Example 51

Synthesis of Compound 51

A mixture of the compound 4 (0.33 g, 0.63 mmol), tetra(tert-butyl) 2,2',2'',2'''-{[2-(4-aminophenyl)ethylimino]bis(methylene)bis(4-bromopyridine-6,2-diyl)bis(methylene-nitrilo)}tetrakis(acetate) (Takalo, H., et al., 1996, Helv. Chim. Acta., 79, 789) (0.21 g, 0.21 mmol), $CsCO_3$ (0.23 g, 0.71 mmol) in dry DMF (2 ml) and 1,2-ethanediol (1 ml) was de-aerated with argon. After addition of tetrakis(triphenylphosphine)palladium (10 mg, 8.4 μmol), the mixture was stirred for 3.5 h at 85° C. The mixture was dissolved in $CH_2Cl_2$ (40 ml), washed with $H_2O$ (3×15 ml) and dried with $Na_2SO_4$. The product was purified by FC (silica gel, first from 2 to 3% MeOH in $CH_2Cl_2$ (impurities), then from 5 to 10% MeOH in $CH_2Cl_2$ (product). Yield: 0.13 g (38%). $^1H$-NMR ($D_6$-DMSO): 0.84 (36 H, s); 1.37 (36 H, s); 2.70-2.76 (4 H, m); 2.98 (4 H, d, J=13.9 Hz); 3.05 (4 H, d, J=13.9 Hz); 3.39 (8 H, s); 3.91 (4 H, s); 4.02 (4 h, s); 6.43 (2 H, d, J=8.2 Hz); 6.81 (2 H, d, J=8.2 Hz); 7.34 (2 H, t, J=7.4 Hz); 7.36 (2 H, t, J=7.4 Hz); 7.61 (2 H, d, J=7.4 Hz); 7.66 (2 H, d, J=7.1 Hz); 7.75 (4 H, s); 7.78 (2 H, d, J=7.1 Hz) 7.88 (2 H, J=7.4 Hz); 7.96 (2 H, s). $^{13}C$-NMR ($D_6$-DMSO):.24.84; 26.84; 27.66; 43.92; 50.51; 54.60; 55.26; 59.25; 59.41; 78.95; 80.08; 113.85; 118.07; 118.28; 119.87; 120.22; 122.37; 124.01; 126.10; 127.19; 127.40; 128.24; 128.82; 135.96; 136.43; 139.60; 141.30; 146.32; 148.42; 148.99; 158.82; 159.52; 168.25; 169.86. MALDI TOF-MS mass: calculated ($M+H^+$) 1618.92; found 1618.88.

Example 52

Synthesis of Compound 52

This compound 52 was synthesized from the compound 51 using a method analogous to the synthesis described in the Example 45 having 4 h reaction time. Yield: 93%. $^1H$-NMR ($D_6$-DMSO): 3.01 (4 H, d, J=15.4 Hz); 3.17 (4 H, d, J=15.4 Hz); 3.30-3.37 (4 H, m); 3.59 (8 H, s); 4.16 (4 H, s); 4.65 (4 H, s); 6.60 (2 H, d, J=7.9 Hz); 6.95 (2 H, d, J=7.9 Hz); 7.34 (2 H, td, J=7.4 and 0.7 Hz); 7.38 (2 H, td, J=7.4 and 1.0 Hz); 7.63 (2 h, d, J=7.4 Hz); 7.77 (2 H, dd, J=7.9 and 0.9 Hz); 7.86 (2 H, d, J=7.4 Hz); 7.87 (2 H, s); 7.95 (2 H, d, J=7.9 Hz); 8.01 (2 H, s); 8.06 (2 H, s). $^{13}$C-NMR (D$_6$-DMSO): 29.31; 41.97; 49.50; 54.59; 54.98; 56.92; 59.24; 115.29; 118.28; 119.91; 120.38; 120.52; 120.60; 121.85; 123.73; 126.27; 127.41; 127.55; 129.23; 135.36; 139.20; 141.46; 149.30; 150.50; 151.43; 157.57; 157.83; 159.79; 171.13; 172.42. MALDI TOF-MS mass: calculated (M+H$^+$) 1169.42; found 1169.49.

Example 53

Synthesis of Compound 53

This compound 53 was synthesized from the compound 52 using a method analogous to the synthesis described in the Example 47. MALDI TOF-MS mass (negative mode): calculated 1428.21; found 1428.03.

Example 54

Synthesis of Compound 54

This compound 54 was synthesized from the compound 53 using a method analogous to the synthesis described in the Example 42. MALDI TOF-MS mass (negative mode): calculated 1470.17; found 1471.36. R$_f$(HPLC): 24.7 min. UV (HPLC): 326 nm.

Example 55

Synthesis of Compound 55

A mixture of the compound 22 (0.19 g, 0.33 mmol), tetra(tert-butyl) 2,2',2",2'''-{[2(4-aminophenyl)ethylimino]bis(methylene)bis(4-bromopyridine-6,2-diyl)bis(methylene-nitrilo)}tetrakis(acetate) (Takalo, H., et al., 1996, Helv. Chim. Acta., 79, 789) (0.11 g, 0.11 mmol), CsCO$_3$ (0.12 g, 0.37 mmol) in dry DMF (1 ml) was de-aerated with argon. After addition of tetrakis(triphenylphosphine)palladium (10 mg, 8.4 µmol) and H$_2$O (10 µl, 0.55 mmol), the mixture was stirred for 3.5 h at 85° C. The mixture was dissolved in CH$_2$Cl$_2$ (20 ml), washed with H$_2$O (2×10 ml) and dried with Na$_2$SO$_4$. The product was purified by FC (silica gel, first 40% EtOAc in petroleum ether (b.p. 40-65° C.), then 40% EtOAc in petroleum ether (b.p. 40-65° C.) and 10% triethylamine). Yield: 0.12 g (63%). $^1$H-NMR (D$_6$-DMS0):1.36 (36 +18 H, s); 1.53 (18 H, s); 2.76-2.83 (4 H, m); 3.47 (8 H, s); 3.97 (4 H, s); 3.99 (4 H, s); 4.00 (4 H, s); 4.44 (4 H, s); 4.69 (2 H, broad s); 5.26 (4 H, s); 6.43 (2 H, d, J=8.3 Hz); 6.87 (2 H, d, J=8.3 Hz); 7.15 (2 H, t, J=7.8 Hz); 7.39 (2 H, d, J=7.8 Hz); 7.43 (2 H, t, J=7.8 Hz); 7.46 (2 H, d, J=8.7 Hz); 7.75 (2 H, dd, J=8.7 and 1.1 Hz); 7.82 (4 H, s); 8.07 (2 H, d, J=8.7 Hz); 8.49 (2 H, d, J=1.1 Hz). $^{13}$C-NMR (D$_6$-DMSO): 27.71; 27.79; 35.80; 43.88; 49.53; 50.21; 54.92; 55.49; 59.57; 59.70; 80.19; 80.84; 81.94; 109.34; 109.71; 113.95; 118.02; 118.26; 118.34; 119.37; 120.27; 122.32; 122.94; 124.44; 126.00; 126.02; 127.38; 128.83; 129.02; 141.22; 148.72; 158.81; 159.35; 162.31; 167.79; 168.58; 170.12. MALDI TOF-MS mass: calculated (M+H$^+$) 1734.95; found 1735.18.

Example 56

Synthesis of Compound 56

This compound 56 was synthesized from the compound 55 using a method analogous to the synthesis described in the Example 52. Yield: 94%. $^1$H-NMR (D$_6$-DMSO): 3.05-3.13 (2 H, m); 3.31-3.43 (2 H, m); 3.61(8 H, s); 4.03 (4 H, s); 4.18 (4 H, s); 4.49 (4 H, s); 4.68 (4 H, s); 5.34 (4 H, s); 6.73 (2 H, d, J=8.0 Hz); 7.06 (2 H, d, J=8.0 Hz); 7.25 (2 H, t, J=7.6 Hz); 7.44 (2 H, d, J=7.6 Hz); 7.47 (2 H, t, J=7.6 Hz); 7.51 (2 H, d, J=8.6 Hz); 7.88 (2 H, dd, J=8.6 and 1.1 Hz); 7.98 (2 H, s); 8.13 (2 H, s); 8.18 (2 H, d, J=7.6 Hz); 8.60 (2 H, d, J=1.1 Hz).
$^{13}$C-NMR (D$_6$-DMSO): 34.75; 45.89; 48.69; 49.49; 54.77; 55.30; 57.11; 59.26; 109.62; 109.98; 118.19; 118.83; 119.51; 119.57; 119.83; 120.35; 120.52; 122.26; 123.03; 124.52; 126.25; 127.37; 129.51; 141.38; 141.72; 150.26; 157.86; 158.12; 159.41; 167.91; 170.28; 170.97; 172.58. MALDI TOF-MS mass: calculated (M+2H$^+$) 1286.45; found 1286.46.

Example 57

Synthesis of Compound 57

This compound 57 was synthesized from the compound 56 using a method analogous to the synthesis described in the Example 47. MALDI TOF-MS mass (negative mode): calculated 1544.25; found 1543.99. R$_f$(HPLC): 18.4 min. UV (HPLC): 285 (sh), 300 and 329 nm.

Example 58

Synthesis of Compound 58

This compound 58 was synthesized from the compound 57 using a method analogous to the synthesis described in the Example 42. MALDI TOF-MS mass (negative mode): calculated 1586.20; found 1585.17. R$_f$(HPLC): 21.1 min. UV (HPLC): 285, 298 and 340 nm.

Example 59

Luminescence Measurements of Eu(III) Chelates With the Compounds 11, 12, 14, 27 and 28

The luminescence parameters for Eu(III) complexes with ligands 11, 12, 14, 27, 28, and 35 were measured in 10 mM NH$_3$-HCl buffer, pH 8.3. The molar absorptivities (ε), excitation maxima ($\lambda_{exc}$), luminescence lifetimes (τ), quantum yields (Φ), calculated luminescence yields (ε×Φ) and triplet stage (T) are presented in Table 1. Reference ligand, 2,2',2",2'''-[(4-phenylethynylpyridine-2,6-diyl)bis(methylenenitrilo)]tetrakis-(acetic acid) (Latva, M, et al., 1997, J. Luminescence, 75, 149) was used as a reference to demonstrate improvements of the ligands of present invention related to prior art seven dentate ligands.

TABLE 1

| Ligand | ε/cm$^{-1}$M$^{-1}$ | $\lambda_{exc}$/nm | τ/µs | Φ | ε × Φ/cm$^{-1}$M$^{-1}$ | T/cm$^{-1}$ |
| --- | --- | --- | --- | --- | --- | --- |
| 11 | 104 000 | 323 | 380 | 0.046 | 4 800 | 20 000 |
| 12 | 35 000 | 328 | 390 | 0.10 | 3 500 | 20 100 |
| 14 | 38 200 | 342 | 355 | 0.11 | 4 200 | 19 200 |
| 27 | 36 700 | 288 | 387 | 0.12 | 4 400 | 22 000 |

TABLE 1-continued

| Ligand | ε/cm$^{-1}$M$^{-1}$ | $\lambda_{exc}$/nm | τ/μs | Φ | ε × Φ/cm$^{-1}$M$^{-1}$ | T/cm$^{-1}$ |
|---|---|---|---|---|---|---|
| 28 | 26 000 | 315 | 382 | 0.10 | 2 600 | 21 300 |
| Ref ligand | 26 950 | 293 | 385 | 0.067 | 1 800 | 21 600 |

With respect to ligand 28, the reason behind the reduced absorptivity of that chelate compared to the reference ligand is most likely due to low CT state or triplet state through which the energy from the antenna chromophore transfers to the Eu(III) ion. However, even in view of the low CT and/or triplet state, it still has a higher quantum yield compared to the reference ligand and thus gives higher emission i.e. it is brighter.

Example 60

Coupling of Chelate 49 and 54 and to a Protein

Labeling was performed in 10 mM botate buffer, pH 8.6-9.0 using 30-fold molar excess of chelates. Reactions were normally carried out overnight at +4° C. or at room temperature. Labeled antibodies were purified on Superfex 200 HR 10/30 or Superdex 200 HiLoad 26/60 gel filtration columns using Tris-saline-azide 86.1 g/L Tris, 9.0 g/L NaCl, and 0.5 g/L NaN$_3$), pH 7.75 as an elution buffer. The fractions containing the antibody were pooled and the europium concentrations measured against europium calibrator. The purified antibody comjugate and the labeling ratio (i.e. chelates per protein) were quantified by calculating the protein yield or by measureing the absorbance at 280 nm and subtracting the absorption caused by the added chelate.

An earlier published nine dentate label {2,2',2'',2'''-{[2-(4-isothiocyanato-phenyl)ethylimino]bis(methylene)bis{4-{[4-(α-galactopyranoxy)phenyl]ethynyl}-pyridine-bis(methylenenitrilo)}tetrakis(acetato)}europium(III) (von Loden, P., et al., 2003, Anal. Chem. 75, 3193) was used as a reference label.

Example 61

Performed Model Immunoassays With the Chelate-Labelled Antibodies

Two labels 49 and 54 were tested in a model cTnI assay. The cTnI immunoassays were performed by using biotinylated capture cTnI antibodies together with the labelled cTnI detection antibodies described above and according to the main principles described in published method (von Loden, P., et al., 2003, Anal. Chem. 75, 3193). The combined assay/wash buffer contained 5 mmol HEPES, 2.1 g/L NaCl, 0.1 mmol EDTA, 0.055 g/L Tween 20 and 1 g/L Gernall II, pH 7.75. The capture biotinylated antibodies were pre-incubated in assay wells. The standards followed by the detection label antibody diluted in 20 μl and 10 μl assay buffer, respectively, were applied to the wells. After one hour incubation at 36 C, the wells were washed, dried and measured.

The table 2 shows that the tested chelate labels 49 and 54 gave significantly improved signal levels compared to the reference Eu-label.

TABLE 2

| | First test | | Second test | |
|---|---|---|---|---|
| Label | Reference chelate | Chelate 49 | Reference chelate | Chelate 54 |
| Counts for 0 ng/ml (cTnI standard) | 358 | 1095 | 446 | 421 |
| Counts for 5 ng/ml cTnI standard | 46291 | 110698 | 70986 | 59602 |
| Eu/IgG | 8.2 | 8.9 | 9.3 | 6.3 |
| Signal/Eu | 5602 | 12254 | 7585 | 9394 |
| Signal improvement/Eu | — | 2.2 | — | 1.2 |
| Abs max/nm | 320 | 348 | 320 | 327 |

It is worth of mentioning, that the label 49 after coupled in protein shown broad excitation around 350 nm, which offers excitation by low-price LED based instrumentation.

Example 62

Synthesis of Compound 59

This compound 59 was synthesized from 2-bromofluorene and BrCH$_2$COOEt using the method analogous to the synthesis described in the Example 2. The product was purified by FC (silica gel, from 4% to 10% EtOAc in petroleum ether (b.p. 40-65° C.)). Yield: 50%. $^1$H-NMR (CDCl$_3$): 1.01 (6 H, t, J=7.2 Hz); 3.01 (2 H, d, J=15.3 Hz); 3.06 (2 H, d, J=15.3 Hz); 3.93 (4H, q, J=7.2 Hz); 7.32 (1 H, td, J=7.4 and 1.2 Hz); 7.37 (1 H, td, J=7.4 and 1.2 Hz); 7.49 (1 H, dd, J=8.1 and 1.8 Hz); 7.66-7.69 (1 H, m); 7.57 (1 H, d, J=8.1 Hz); 7.50-7.53 (1 H, m); 7.70 (1 H, d, J=1.8 Hz). MALDI TOF-MS mass: calculated (M+H$^+$) 417.07 and 419.07; found 417.72 and 419.79.

Example 63

Synthesis of Compound 60

This compound 60 was synthesized from the compound 59 using the method analogous to the synthesis described in the Example 5. Reaction time 20 min. The product was purified by FC (silica gel, 10% EtOAc in petroleum ether (b.p. 40-65° C.)). Yield: 88%. $^1$H-NMR (CDCl$_3$): 0.27 (9 H, s); 1.00 (6 H, t, J=7.1 Hz); 3.02 (2 H, d, J=15.2 Hz); 3.06 (2 H, d, J=15.2 Hz); 3.92 (4 H, q, J=7.1 Hz); 7.31 (1 H, td, J=7.4 and 1.1 Hz); 7.36 (1 H, td, J=7.4 and 1.1 Hz); 7.48 (1 H, dd, J=7.8 and 1.3 Hz); 7.53 (1 H, d, J=7.4 Hz); 7.63 (1 H, d, J=7.8 Hz); 7.63 (1 H, J=1.3 Hz); 7.68 (1 H, d, J=7.4 Hz). $^{13}$C-NMR (CDCl$_3$): 0.01; 13.84; 42.07; 49.73; 60.22; 94.29; 105.69; 119.73; 120.27; 121.76; 123.82; 127.39; 127.80; 128.00; 131.90; 139.43; 140.48; 148.56; 148.88; 170.36. MALDI TOF-MS mass: calculated (M+H$^+$) 435.20; found 435.10.

Example 64

Synthesis of Compound 61

This compound 61 was synthesized from the compound 60 using the method analogous to the synthesis described in the Example 7. The product was purified by FC (silica gel, 10% EtOAc in petroleum ether (b.p. 40-65° C.)). Yield: 100%. $^1$H-NMR (CDCl$_3$): 1.00 (6 H, t, J=7.2 Hz); 3.03 (2 H, d, J=15.6 Hz); 3.06 (2 H, d, J=15.6 Hz); 3.11 (1 H, s); 3.91 (2 H, q, J=7.2 Hz); 3.92 (2 H, q, J=7.2 Hz); 7.32 (1 H, td, J=7.5 Hz and 1.2 Hz); 7.37 (1 H, td, J=7.5 and 1.2 Hz); 7.51 (1 H, d, J=7.8 Hz); 7.53 (1 H, d, J=7.4 Hz); 7.65 (1 H, d, J=7.8 Hz); 7.68 (1 H, d, J=1.2 Hz); 7.70 (1 H, d, J=7.4 Hz). $^{13}$C-NMR (CDCl$_3$): 13.85; 42.04; 49.77; 60.22; 77.23; 84.21; 119.81; 120.33; 120.68; 123.81; 127.66; 127.92; 128.05; 132.06; 139.29; 140.81; 148.62; 148.89; 170.31. MALDI TOF-MS mass: calculated (M+H$^+$) 363.16; found 393.98.

Example 65

Synthesis of Compound 63

A mixture of the compound 61 (91 mg, 252 µmol), compound 62 (WO 201326790) (116 mg, 105 µmol) in dry triethylamine (1 ml) and THF (2 ml) was de-aerated with argon. After addition of bis(triphenyl-phosphine)palladium (II) chloride (10 mg, 14 µmol), CuI (6 mg, 28 µmol), the mixture was stirred for 18 h at 55° C. After evaporation to dryness, the product was purified by FC (silica gel, 70% EtOAc in petroleum ether (b.p. 40-65° C.) containing 1% TEA. Yield: 125 mg (71%). MALDI TOF-MS mass: calculated (M+Na$^+$) 1690.62 and 1692.62, found 1690.96 and 1692.70.

Example 66

Synthesis of Compound 64

A mixture of the compound 63 (113 mg, 67 µmol) and 0.5M KOH in EtOH (9 ml) was stirred for 0.5 h at RT and H$_2$O was added (2 ml). After stirring for 3 h at RT, EtOH was evaporated, the mixture was stirred for 5 h at RT, and the pH was adjusted to ca. 6.5 with 6M HCl. EuCl$_3$×6H$_2$O (25 mg, 67 µmol) in H$_2$O (0.2 ml) was added within 10 min and the pH was maintained at 5-7 with solid NaHCO$_3$. After stirring for 20 h at RT, the pH was raised to 8.5 with 1M NaOH, the mixture was stirred over-night and the precipitate was centrifuged off and the supernatant was extracted with phenol (once with 0.75 g and 3×0.5 g). The combined phenol phases were treated with H$_2$O (1 ml) and Et$_2$O (20 ml), the aqueous phase was washed with Et$_2$O (2×20 ml), and triturated with acetone. The precipitate was centrifuged and washed with acetone. The product was used for the next step without further purification. MALDI TOF-MS mass: calculated (M+H$^+$) 1602.09, found 1602.25.

Example 67

Synthesis of Compound 65

This compound 65 was synthesized from the compound 64 using the method analogous to the synthesis described in the Example 42. MALDI TOF-MS mass: calculated (M+H$^+$) 1644.15, found 1643.01.

Example 68

Synthesis of Compound 66

Taurine (12.5 mg, 100 µmol) in 50 mM Na$_2$CO$_3$ buffer (pH 9.8; 0.55 ml) was added to a solution of compound 65 (16.4 mg, 10 µmol) in 50 mM Na$_2$CO$_3$ buffer (pH 9.8; 0.55 ml). After stirring over-night at RT, the reaction mixture was evaporated to dryness and the product was purified by using reversed phase HPLC (RP-18 column). The solvents were A: Triethyl ammonium acetate buffer (20 mM, pH 7) and B: 50% acetonitrile in triethyl ammonium acetate buffer (20mM, pH 7). The gradient was started from 5% of solvent B and the amount of solvent B was linearly raised to 100% in 25 minutes. R$_t$(HPLC): 20.9 min. UV (HPLC): 280 and 352 nm.

Example 69

Synthesis of Compound 67

A mixture of 7-iodo-2-nitrofluorene (0.51 g, 1.5 mmol), dry K$_2$CO$_3$ (0.83 g, 6.0 mmol) and BrCH$_2$COOEt (0.48 ml, 4.4 mmol) in dry DMF was stirred for 1 h at 100° C. The mixture was filtered, washed with DMF and the filtrate was evaporated to dryness. The product was purified by FC (silica gel, from 5% to 15% EtOAc to in pertroleum ether (b.p. 50-65° C.)). Yield: 0.51 g (67%). $^1$H-NMR (CDCl$_3$): 1.03 (6 H, t, J=7.1 Hz); 3.06 (2 H, d, J=15.6 Hz); 3.12 (2 H, d, J=15.6 Hz); 3.94 (4 H, q, J=7.1 Hz); 7.74 (1 H, d, J=8.0 Hz); 7.78 (1 H, dd, J=8.0 and 1.2 Hz); 7.80 (1 H, d, J=8.4 Hz); 7.94 (1 H, d, J=1.2 Hz); 8.30 (1 H, dd, J=8.4 and 1.9 Hz); 8.42 (1 H, d, J=1.9 Hz). $^{13}$C-NMR (CDCl$_3$): 13.82; 41.67; 49.99; 60.56; 95.24; 119.35; 120.16; 122.76; 124.20; 133.30; 137.52; 137.55; 145.66; 147.45; 149.22; 151.87; 169.43. MALDI TOF-MS mass: calculated (M+H$^+$) 510.04; found 510.29.

Example 70

Synthesis of Compound 68

A mixture of compound 67 (0.50 g, 0.98 mmol) and SnCl$_2$×HCl (1.03 g, 4.64 mmol) in dry EtOH (20 ml) was refluxed for 2.5 h. The cold mixture was poured to H$_2$O (20 ml), neutralized with solid NaHCO$_3$, extracted with CH$_2$Cl$_2$ (2×40 ml) and dried with Na$_2$SO$_4$. The product was purified by FC (silica gel, from 30% to 40% EtOAc to in pertroleum ether (b.p. 50-65° C.)). Yield: 0.39 g (83%). $^1$H-NMR (CDCl$_3$): 1.06 (6 H, t, J=7.1 Hz); 2.95 (2H, d, J=15.4 Hz); 3.01 (2 H, d, J=15.4 Hz); 3.7-3.9 (2 H, bs); 3.96 (2 H, qd, J=14.2 and 7.1 Hz); 3.97 (2 H, qd, J=14.2 and 7.1 Hz); 6.66 (1 H, dd, J=8.1 and 2.0 Hz); 6.87 (1 H, d, J=2.0 Hz); 7.29 (1 H, d, J=8.0 Hz); 7.44 (1 H, d, J=8.1 Hz); 7.61 (1 H, dd, J=8.0 and 1.4 Hz); 7.77 (1 H, d, J=1.4 Hz). $^{13}$C-NMR (CDCl$_3$): 13.89; 41.76; 49.44; 60.17; 89.82; 110.35; 114.78; 120.25; 120.96; 129.81; 132.75; 136.60; 140.16; 146.74; 149.99; 150.21; 170.46. MALDI TOF-MS mass: calculated (M+H$^+$) 480.07; found 479.92.

Example 71

Synthesis of Compound 69

This compound 69 was synthesized from the compound 68 using a method analogous to the synthesis described in the Example 13. Reaction time 3 h. The product was purified by FC (silica gel, 40% EtOAc in petroleum ether (b.p. 40-65° C.)). Yield: 100%. $^1$H-NMR (CDCl$_3$): 0.26 (9 H, s); 1.04 (6 H, t, J=7.1 Hz); 2.99 (4 H, s); 3.94 (2 H, qd, J=14.2 and 7.1 Hz); 3.96 (2 H, qd, J=14.2 and 7.1 Hz); 6.67 (1 H, dd, J=8.1 and 2.0 Hz); 6.89 (1 H, d, J=2.0 Hz); 7.42 (1 H, dd, J=7.8 and 1.1 Hz); 7.45 (1 H, d, J=8.1 Hz); 7.46 (1 H, d, J=7.8 Hz); 7.59 (1 H, d, J=1.1 Hz). $^{13}$C-NMR (CDCl$_3$): 0.06; 13.90; 41.93; 49.35; 60.21; 93.47; 106.10; 110.59; 114.84; 118.35; 119.76; 121.27; 127.14; 130.30; 131.89; 141.00;

146.72; 147.74; 151.08; 170.64. MALDI TOF-MS mass: calculated (M+H$^+$) 450.21; found 449.93.

Example 72

Synthesis of Compound 70

This compound 70 was synthesized from the compound 69 using a method analogous to the synthesis described in the Example 7. Yield: 100%. $^1$H-NMR (CDCl$_3$): 1.04 (6 H, t, J=7.2 Hz); 2.98 (2 H, d, J=15.4 Hz); 3.02 (2 H, d, J=15.4 Hz); 3.07 (1 H, s); 3.95 (2×2H, qd, J=14.3 and 7.2 Hz); 6.67 (1 H, dd, J=8.2 and 2.0 Hz); 6.88 (1 H, d, J=2.0 Hz); 7.44 (1 H, dd, J=7.9 and 1.1 Hz); 7.47 (1 H, d, J=8.2 Hz); 7.48 (1 H, d, J=7.9 Hz); 7.58 (1 H, d, J=1.1 Hz). $^{13}$C-NMR (CDCl$_3$): 13.91; 41.91; 49.39; 60.22; 76.53; 84.56; 110.52; 114.86; 118.43; 118.66; 121.33; 127.38: 130.13; 132.05; 141.33; 146.85; 147.80; 151.08; 170.59. MALDI TOF-MS mass: calculated (M+H$^+$) 378.17; found 377.95.

Example 73

Synthesis of Compound 71

A dry THF solution (15 ml) of compound 70 (1.04 g, 2.76 mmol) was added within 10 min into a solution of dry THF (10 ml) and trifluoroacetic anhydride (1.53 ml, 11.0 mmol) on ice-water. After stirring for 10 min on ice, and 30 min at RT the solution was poured to ice-water (100 ml), neutralized with solid NaHCO$_3$, extracted with CH$_2$Cl$_2$ (2×40 ml) and dried with Na$_2$SO$_4$. Yield: 1.31 g (100%). $^1$H-NMR (CDCl$_3$): 1.01 (6 H, t, J=7.2 Hz); 3.03 (2 H, d, J=15.4 Hz); 3.08 (2 H, d, J=15.4 Hz); 3.13 (1 H, s); 3.92 (2 H, qd, J=14.3 and 7.2 Hz); 3.93 (2 H, qd, J=14.3 and 7.2 Hz); 7.51 (1 H, dd, J=7.9 and 1.3 Hz), 7.57 (1 H, dd, J=8.3 and 1.9 Hz); 7.62 (1 H, d, J=7.9 Hz); 7.65 (1 H, d, J=1.3 Hz); 7.67 (1 H, d, J=8.3 Hz); 7.86 (1 H, d, J=1.9 Hz), 8.12 (1 H, s). $^{13}$C-NMR (CDCl$_3$): 13.82; 42.06; 49.94; 60.45; 77.62; 83.97; 112.23; 114.53; 116.14; 116.82; 119.13; 119.87; 120.28; 120.92; 120.99; 127.53; 132.28; 135.00; 137.49; 139.88; 148.49; 150.23; 154.16; 154.47; 154.75; 170.12. MALDI TOF-MS mass: calculated (M+H$^+$) 474.16; found 474.95.

Example 74

Synthesis of Compound 72

A mixture of compound 71 (1.10 g, 2.40 mmol), 6-bromo-2,6-dihydroxymethylpyridine (Takalo, H., et al., 1988, Acta Chem. Scand. Ser B, 42, 614) (0.44 g, 2.00 mmol) in dry triethylamine (5 ml) and dry THF (10 ml) was de-aerated with argon. After addition of bis(triphenylphosphine)palladium(II) chloride (28 mg, 0.04 mmol), CuI (15 mg, 0.08 mmol), the mixture was stirred for 23 h at 55° C. After evaporation to dryness and an addition of CH$_2$Cl$_2$ (40 ml), the cold mixture was filtered and the product washed with cold CH$_2$Cl$_2$. Yield: 0.97 g (80%). $^1$H-NMR (D$_6$-DMSO): 0.79 (6H, t, J=7.1 Hz); 3.12 (2 H, d, J=15.0 Hz); 3.19 (2 H, d, J=15.0 Hz); 3.78 (4 H, q, J=7.1 Hz); 4.55 (4 H, s); 5.51 (2 H, s); 7.36-7.56 (2 H, bs); 7.62 (1 H, dd, J=7.9 and 1.3 Hz); 7.68 (1 H, dd, J=8.3 and 1.8 Hz); 7.86 (1 H, d, J=7.9 Hz); 7.89 (1 H, d, J=8.3 Hz); 7.90-7.94 (2 H, m), 11.39 (1 H, s). $^{13}$C-NMR (D$_6$-DMSO): 13.98; 42.51; 50.49; 59.91; 88.13; 94.28; 112.83; 115.13; 117.04; 117.42; 119.71; 119.84; 120.64; 121.30; 121.41; 127.63; 131.95; 136.40; 137.41; 141.36; 149. 47; 149.85; 154.36; 154.58; 155.02; 169.59. MALDI TOF-MS mass: calculated (M+H$^+$) 611.20; found 612.47.

Example 75

Synthesis of Compound 73

PBr$_3$ (0.22 ml, 2.36 mmol) was added in a suspension of the compound 71 (0.96 g, 1.57 mmol) in dry and EtOH free CHCl$_3$ (65 ml). After stirring for 3 d at 60° C., the mixture was neutralized with 5% NaHCO$_3$ (50 ml). The aqueous phase was extracted with CHCl$_3$ (50 ml) and the combined organic phases were dried with Na$_2$SO$_4$. The product was purified by FC (silica gel, from 0.5% to 3% MeOH in CH$_2$Cl$_2$). Yield: 0.72 g (62%). $^1$H-NMR (CDCl$_3$): 1.02 (6H, t, J=7.2 Hz); 3.07 (2 H, d, J=15.5 Hz); 3.11 (2 H, d, J=15.5 Hz); 3.94 (2 H, qd, J=14.4 and 7.2 Hz); 3.95 (2 H, qd, J=14.4 and 7.2 Hz); 4.54 (2 H, s); 7.48 (2 H, s); 7.58 (1 H, dd, J=7.9 and 1.2 Hz); 7.60 (1 H, dd, J=8.2 and 1.9 Hz); 7.70 (1 H, d, J=7.9 Hz); 7.72 (1 H, d, J=8.2 Hz); 7.74 (1 H, d, J=1.2 Hz); 7.89 (1 H, d, J=1.9 Hz); 8.10 (1 H, s). $^{13}$C-NMR (CDCl$_3$): 13.87; 33.04; 42.04; 50.00; 60.49; 86.70; 95.36; 112.48; 114.53; 116.82; 119.12; 120.10; 120.35; 120.53; 121.18; 124.52; 127.44; 132.20; 133.67; 135.18; 137.37; 140.60; 148.83; 150.42; 154.18; 154.42; 154.78; 156.97; 170.04. MALDI TOF-MS mass: calculated (M+2H$^+$) 738.04, 736.03 and 740.03; found 737.95, 735.85 and 740.01.

Example 76

Synthesis of Compound 75

A mixture of compound 73 (0.71 g, 0.96 mmol), dry K$_2$CO$_3$ and compound 74 (WO 201326790) (0.67 g, 1.92 mmol) in dry MeCN (30 ml) was stirred for 4 h at 65° C. After filtration of solid material and washing with MeCN, the filtrate was evaporated to dryness. The product was purified by FC (silica gel, from 5% to 10% EtOH in CH$_2$Cl$_2$). Yield 0.69 g (57%). $^1$H-NMR (CDCl$_3$): 1.01 (6 H, t, J=7.1 Hz); 1.29 (6 H, t, J=6.8 Hz); 1.41 (6 H, t, J=7.0 Hz); 1.65-1.85 (1 H, bs); 3.06 (2 H, d, J=15.4 Hz); 3.13 (2 H, d, J=15.4 Hz); 3.52 (4 H, s); 3.93 (2 H, qd, J=14.3 and 7.1 Hz); 3.94 (2 H, qd, J=14.3 and 7.1 Hz); 3.99 (4 H, s); 4.13 (4 H, s); 4.19 (4 H, d, J=6.8 Hz); 4.45 (4 H, d, J=7.0 Hz); 7.46 (2 H, s); 7.60 (1 H, d, J=7.9 Hz); 7.64 (1 H, dd, J=8.3 and 1.5 Hz); 7.70 (1 H, d, J=7.9 Hz); 7.73 (1 H, d, J=8.3 Hz); 7.76 (1 H, d, J=1.5 Hz); 7.90 (1 H, s); 8.12 (2 H, 2×s); 8.17 (2 H, s). $^{13}$C-NMR (CDCl$_3$): 13.79; 14.17; 14.18; 42.04; 49.91; 55.31; 59.63; 59.76; 60.31; 60.37; 60.59; 62.15; 87.60; 94.16; 112.17; 114.47; 116.77; 116.77; 119.06; 119.94; 120.27; 120.73; 121.01; 123.33; 126.86; 127.23; 129.19; 132.30; 134.01; 137.45; 140.21; 148.48; 148.74; 150.23; 154.40; 154.69; 154.99; 158.40; 161.85; 164.06; 169.90; 170.95. MALDI TOF-MS mass: calculated (M+H$^+$) 1265.25, 1263.21 and 1267.25; found 1265.86, 1263.01 and 1267.81.

Example 77

Synthesis of Compound 77

This compound 77 was synthesized from the compound 75 and 76 (WO 201326790) using the method analogous to the synthesis described in the Example 73. Reaction time 23 h. The product was purified by FC (silica gel, from 5% to 25% EtOH in CH$_2$Cl$_2$.). Yield: 75%. $^1$H-NMR (D$_6$-DMSO):

0.79 (6 H, t, J=7.1 Hz); 1.18 (6 H, t, J=7.1 Hz); 1.20 (12 H, t, J=7.1 Hz); 1.21 (6 H, t, J=7.1 Hz); 1.32 (6 H, t, J=7.1 Hz); 3.08 (2 H, d, J=15.0 Hz); 3.17 (2 H, d, J=15.0 Hz); 3.32 (4 H, s); 3.70 (4 H, q, J=7.1 Hz); 3.07 (4H, s); 4.03 (4 H, s); 4.06 (4 H, q, J=7.1 Hz); 4.16 (4 H, q, J=7.1 Hz); 4.17 (8 H, q, J=7.1 Hz); 4.33 (4 H, q, J=7.1 Hz); 4.79 (4 H, s); 4.87 (8 H, s), 6.25 (4 H, s); 7.46 (2 H, s); 7.47 (1 H, d, J=7.8 Hz); 7.75 (1 H, d, J=7.8 Hz); 7.69 (1 H, dd, J=8.3 and 1.6 Hz); 7.77 (2 H, 2×2s); 7.82 (1 H, d, J=8.3 Hz); 7.84 (1 H, s); 7.86 (2 H, 2×2s); 7.92 (1 H, d, J=1.6 Hz). MALDI TOF-MS mass: calculated (M+H$^+$): 1920.69; found 1920.31.

Example 78

Synthesis of Compound 78

This compound 78 was synthesized from the compound 77 using the method analogous to the synthesis described in the Example 66. The product was used for the next step without further purification. R$_f$(HPLC): 14.4 min. UV (HPLC): 260 and 364 nm. MALDI TOF-MS mass: calculated (M+H$^+$) 1834.03, found 1833.95.

Example 79

Synthesis of Compound 79

This compound 79 was synthesized from the compound 78 using the method analogous to the synthesis described in the Example 42. The product was used for the next step without further purification. R$_f$(HPLC): 19.9 min. UV (HPLC): 255 and 361 nm. MALDI TOF-MS mass: calculated (M+H$^+$) 1876.09, found 1877.06.

Example 80

Synthesis of Compound 80

This compound 80 was synthesized from the compound 79 using the method analogous to the synthesis described in the Example 68. R$_f$(HPLC): 13.9 min. UV (HPLC): 255 and 357 nm.

Example 81

Photo-Physical Properties of Novel Chelates Conjugated to Taurine (Chelates 66 and 80)

The prepared isothiocyante activated chelates (65 and 79) were conjugated to taurine as described above in Example 68. The products were purified with semi-preparative reversed phase HPLC (RP-18 column). After the product fractions were evaporated the residues were dissolved in 50 mM TRIS buffer.

The measured photo-physical properties excitation wavelengths ($\lambda_{exc}$), luminescence decay times ($\tau$), molar absorptivities ($\varepsilon$), estimated luminescence yields ($\varepsilon\Phi$) of the novel chelates (66 and 80) in 50 mM TRIS buffer (pH 7.75) are in the Table 3. The nine dentate label {2,2',2'',2'''-{[2-(4-isothiocyanato-phenyl)ethylimino]bis(methylene)bis{4-{[4-(α-galactopyranoxy)phenyl]-ethynyl}bis(methylenenitrilo)} tetrakis(acetato)}-europium(III) (von Loden, P., et al., 2003, Anal. Chem. 75, 3193) was used as a reference label.

TABLE 3

| Chelate | $\varepsilon$/ cm$^{-1}$M$^{-1}$ | $\lambda_{exc}$/ nm | $\tau$/ μs | $\varepsilon \times \Phi$/ cm$^{-1}$M$^{-1}$ |
|---|---|---|---|---|
| 66 | 100 000 | 346 | 540 | 8 700 |
| 80 | 105 000 | 354 | 290 | 5 600 |
| Ref chelate | 55 000 | 325 | 1000 | 4 800 |

Example 58

Labelling of Antibody With Chelates 66

The TnI labeled antibodies were prepared as described in Example 61.

The measured photo-physical properties gave the excitation wavelengths ($\lambda_{exc}$) at 354 nm, a luminescence decay times ($\tau$) of 460 μs molar absorptivities (c) of 142 000 cm$^{-1}$M$^{-1}$ and luminescence yields ($\varepsilon\Phi$) of 10 500 cm$^{-1}$M$^{-}$ for the labelled cTnIs with the chelate 66 in 50 mM TRIS buffer (pH 7.75)

Dry measurements gave the luminescence yield of 16 500 cm$^{-1}$M$^{-1}$, which represents estimated luminescence yields based on the signal measurements after dry immunoassay done as described in the Example 61.

Scheme 1

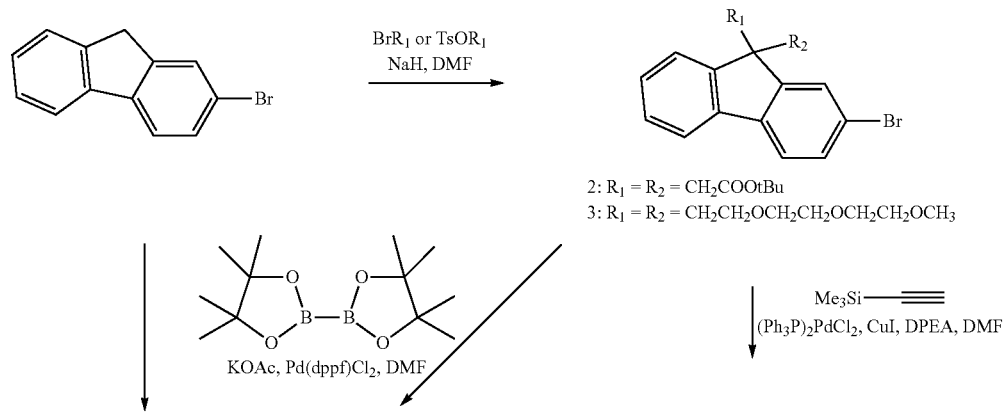

2: R$_1$ = R$_2$ = CH$_2$COOtBu
3: R$_1$ = R$_2$ = CH$_2$CH$_2$OCH$_2$CH$_2$OCH$_2$CH$_2$OCH$_3$

-continued
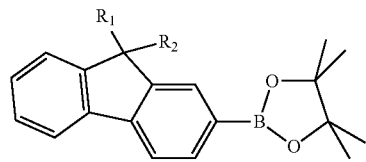
1: R₁ = R₂ = H
4: R₁ = R₂ = CH₂COOtBu
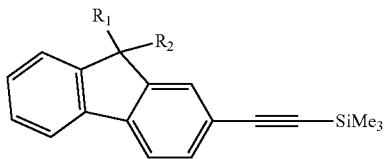
5: R₁ = R₂ = CH₂COOtBu
6: R₁ = R₂ = CH₂CH₂OCH₂CH₂OCH₂CH₂OCH₃
↓ TBAF, DCM
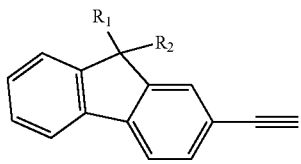
7: R₁ = R₂ = CH₂COOtBu
8: R₁ = R₂ = CH₂CH₂OCH₂CH₂OCH₂CH₂OCH₃
Scheme 2
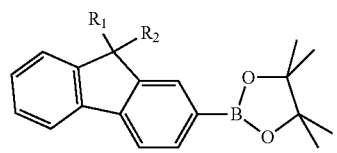
1: R₁ = R₂ = H
4: R₁ = R₂ = CH₂COOtBu
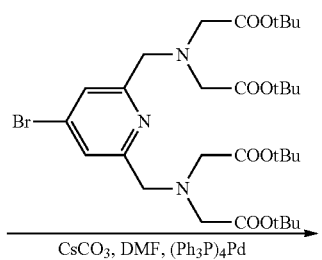
$\xrightarrow{\text{CsCO}_3,\ \text{DMF},\ (\text{Ph}_3\text{P})_4\text{Pd}}$
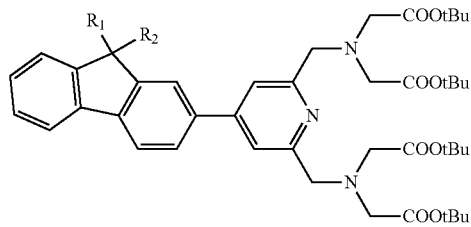
9: R₁ = R₂ = H
10: R₁ = R₂ = CH₂COOtBu
↓ TFA
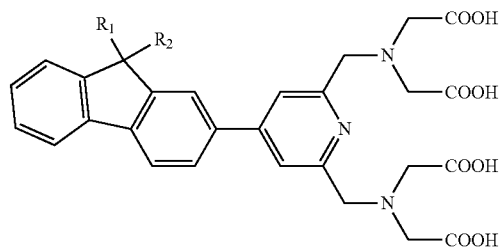
11: R₁ = R₂ = H
12: R₁ = R₂ = CH₂COOH Scheme 3
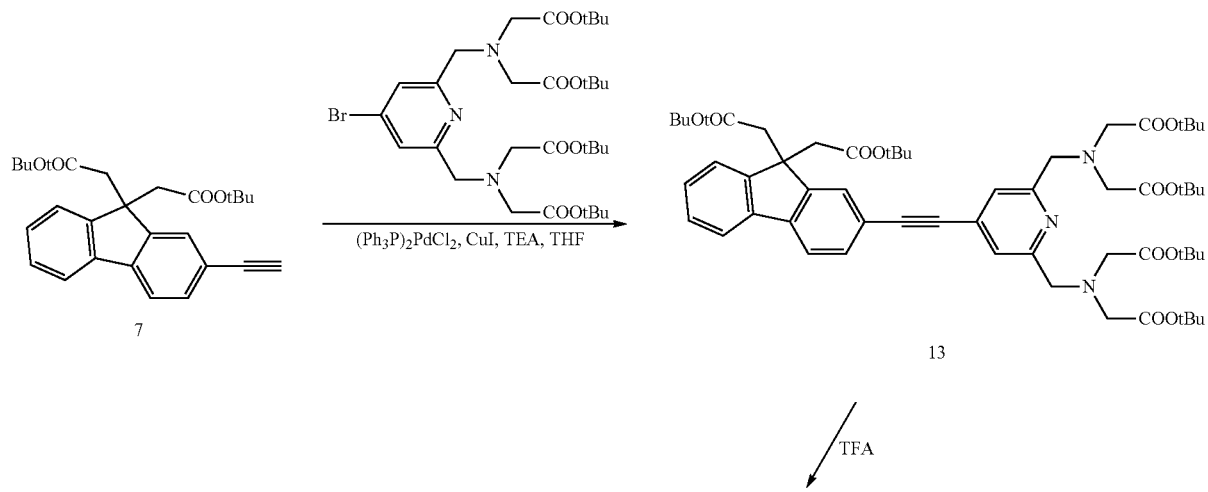
Scheme 4
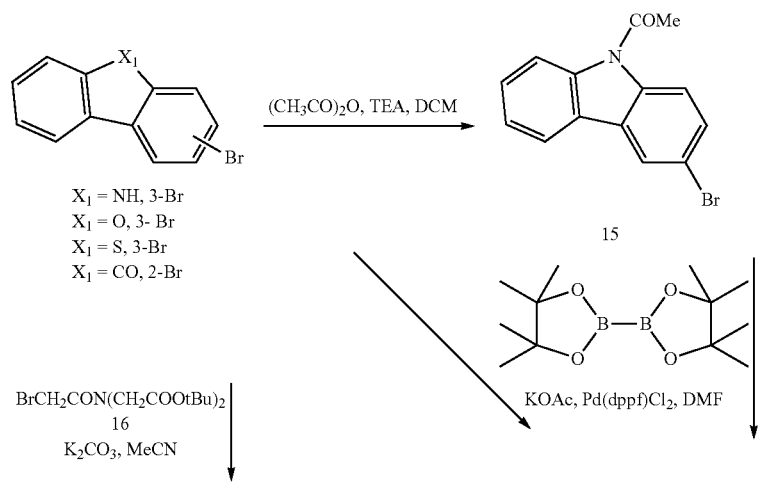

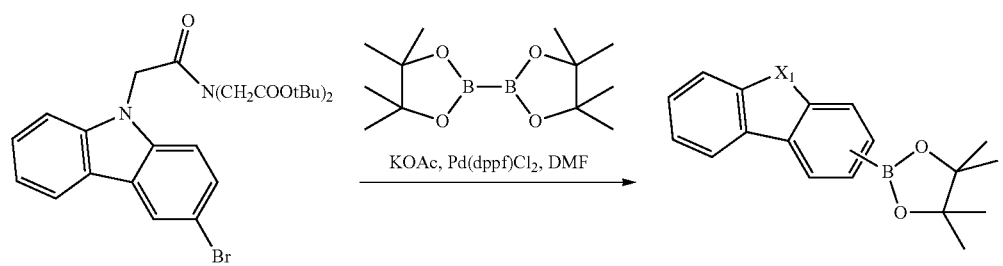
Scheme 5
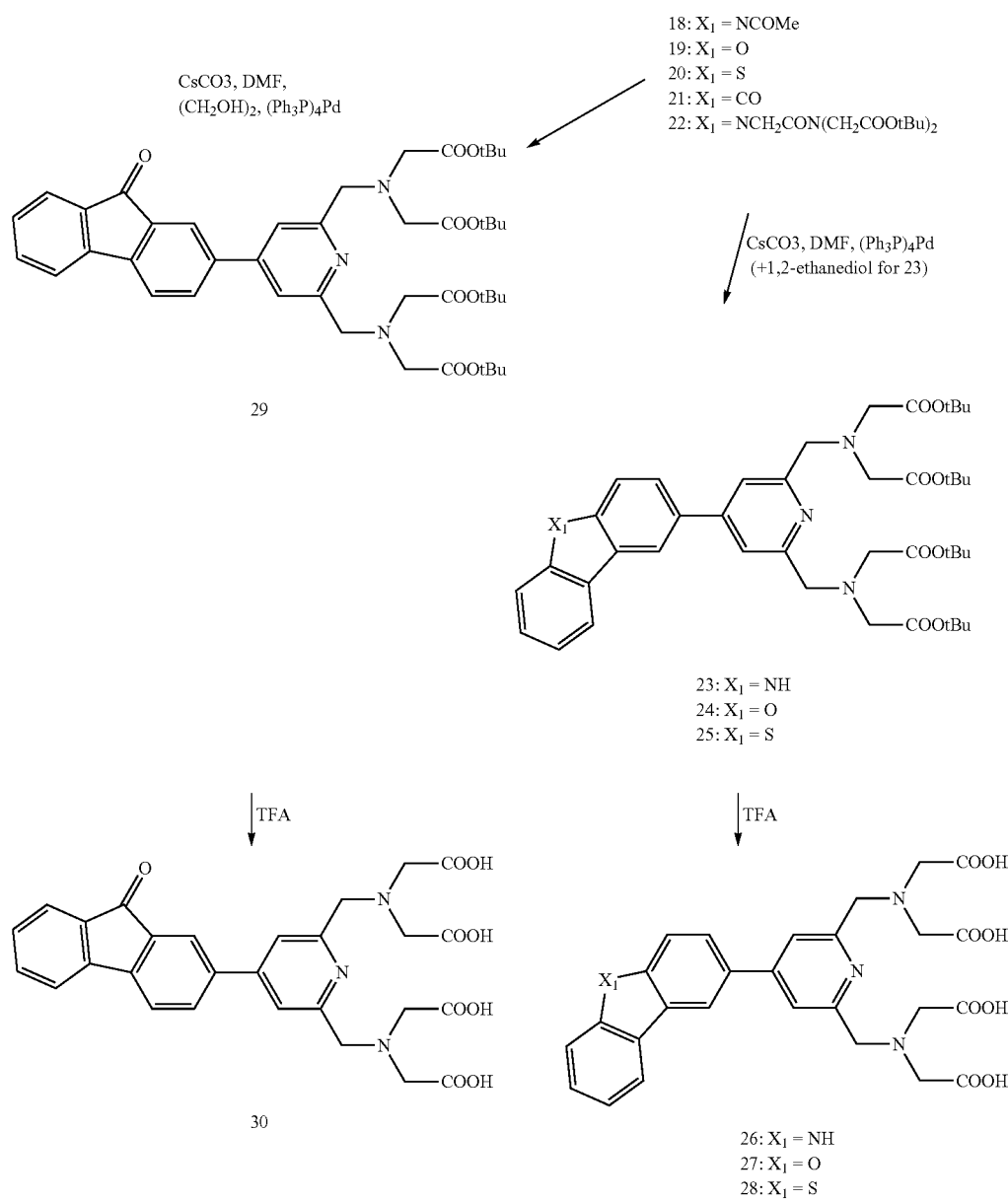

Scheme 7
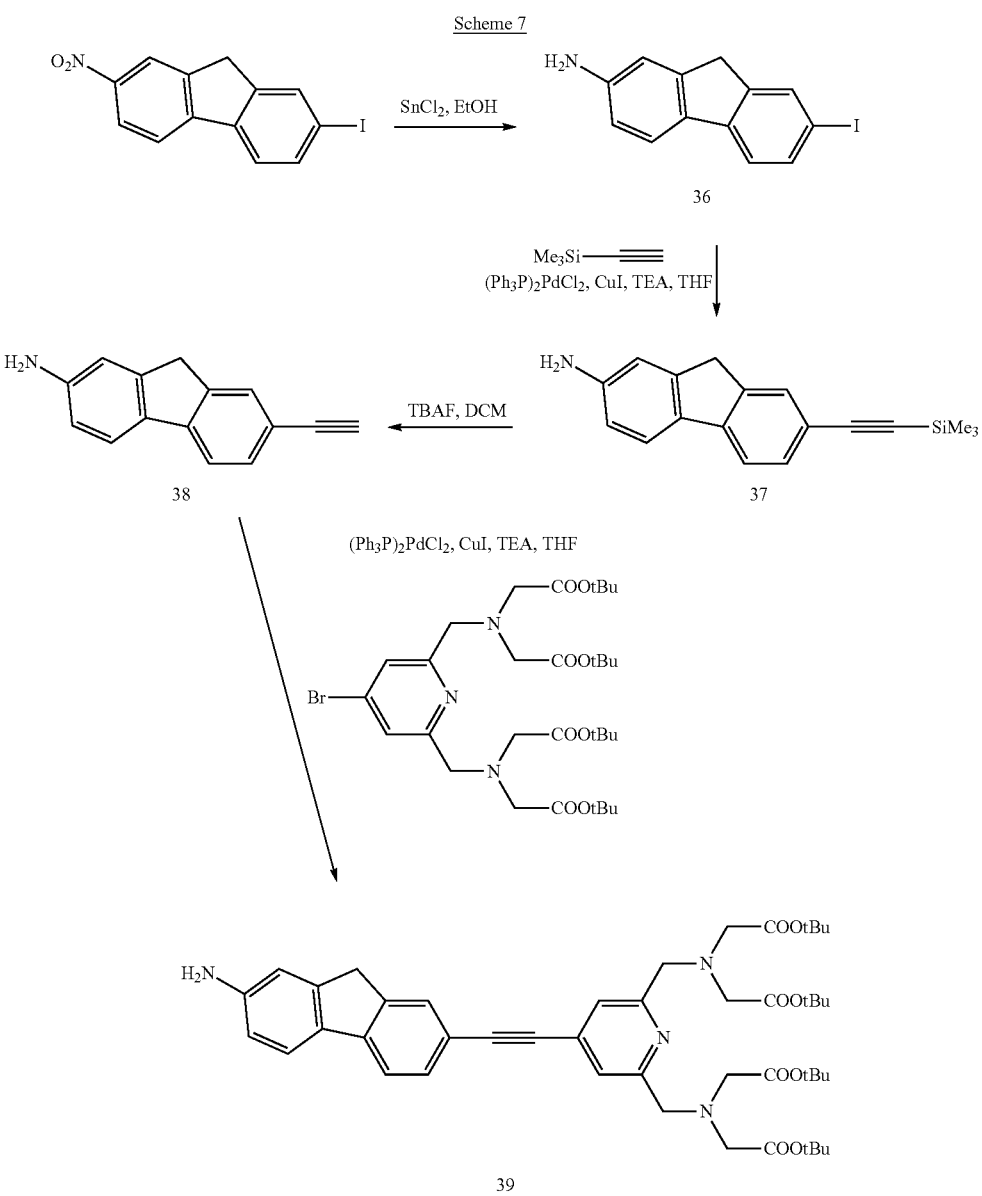
Scheme 8
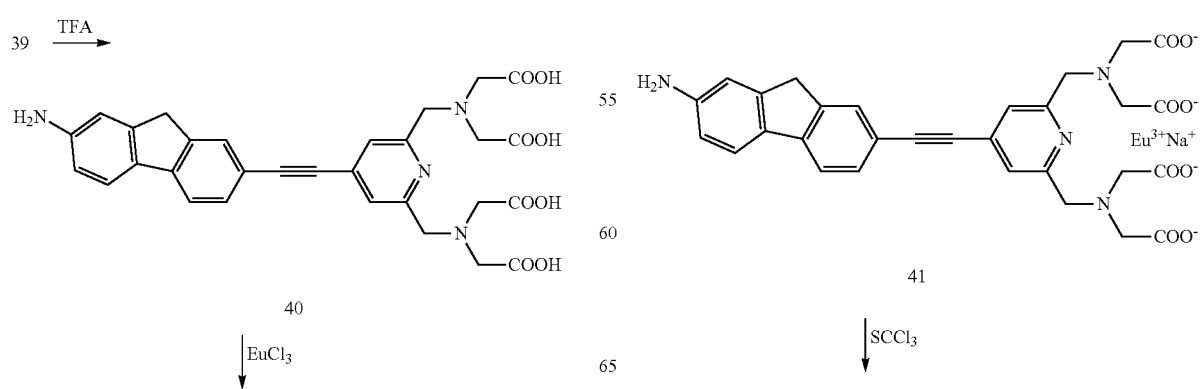

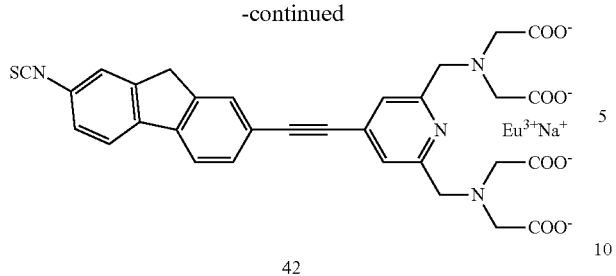
42
Scheme 9
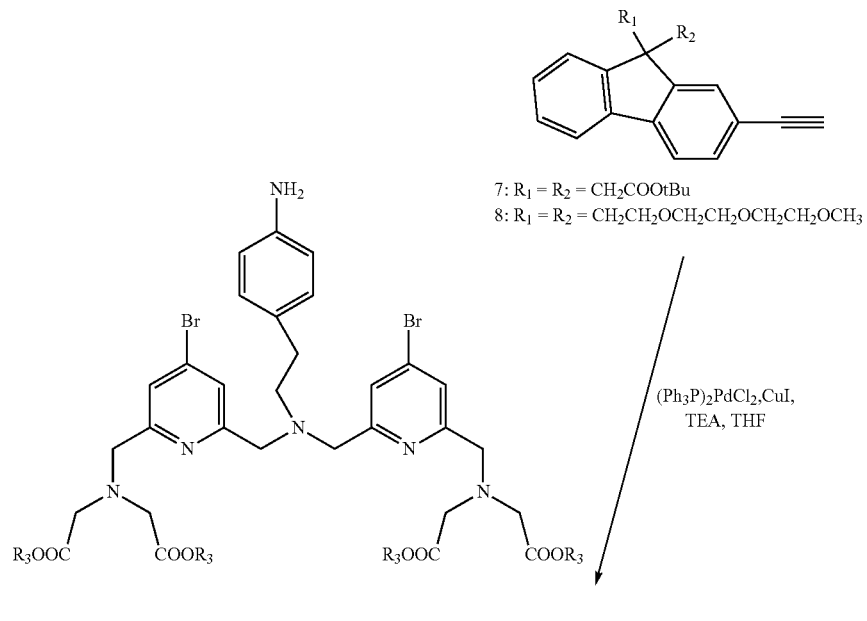
7: R₁ = R₂ = CH₂COOtBu
8: R₁ = R₂ = CH₂CH₂OCH₂CH₂OCH₂CH₂OCH₃
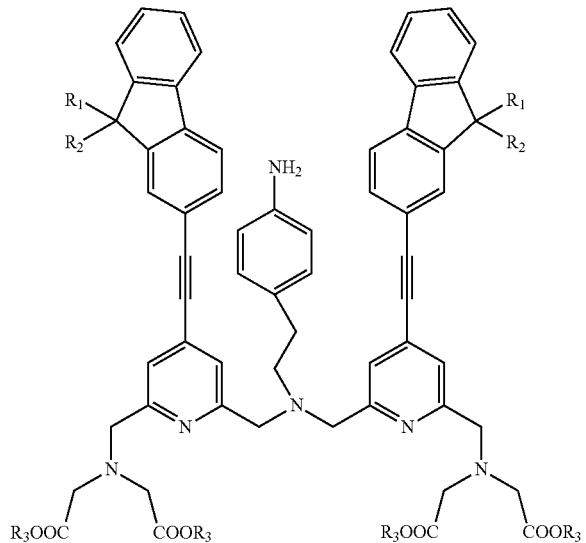
43: R₁ = R₂ = CH₂COOtBu, R₃ = tBu
44: R₁ = R₂ = CH₂CH₂OCH₂CH₂OCH₂CH₂OCH₃, R₃ = tBu US 10,365,286 B2
Scheme 10
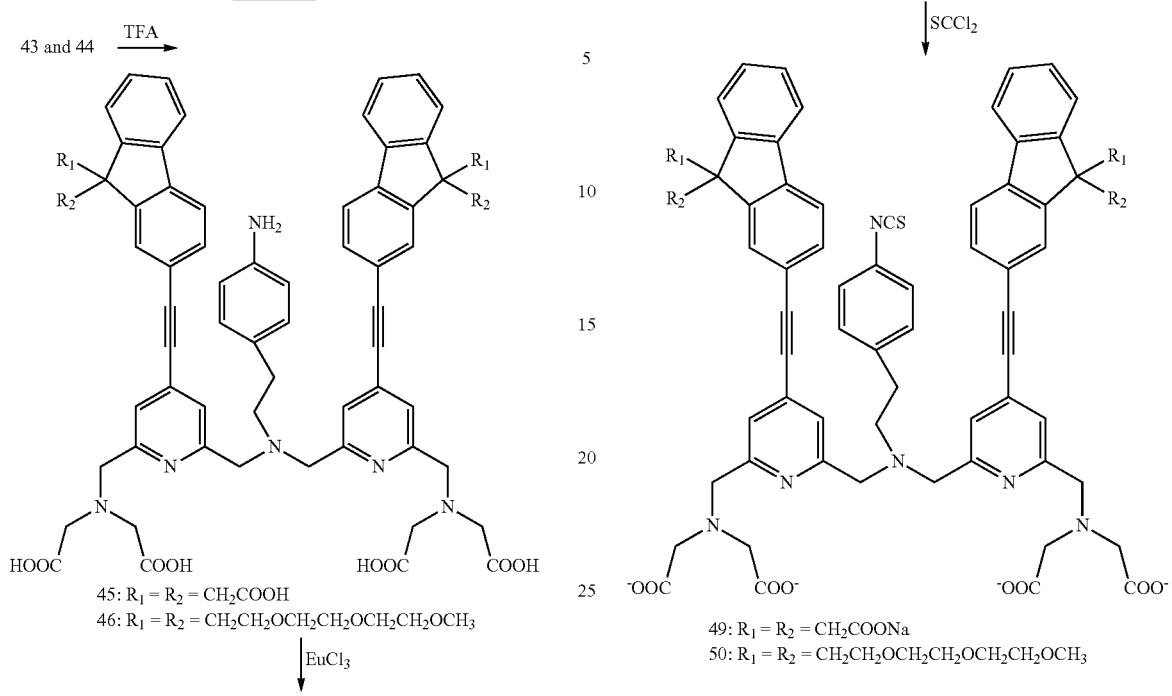
45: $R_1 = R_2 = CH_2COOH$
46: $R_1 = R_2 = CH_2CH_2OCH_2CH_2OCH_2CH_2OCH_3$
49: $R_1 = R_2 = CH_2COONa$
50: $R_1 = R_2 = CH_2CH_2OCH_2CH_2OCH_2CH_2OCH_3$
Scheme 11
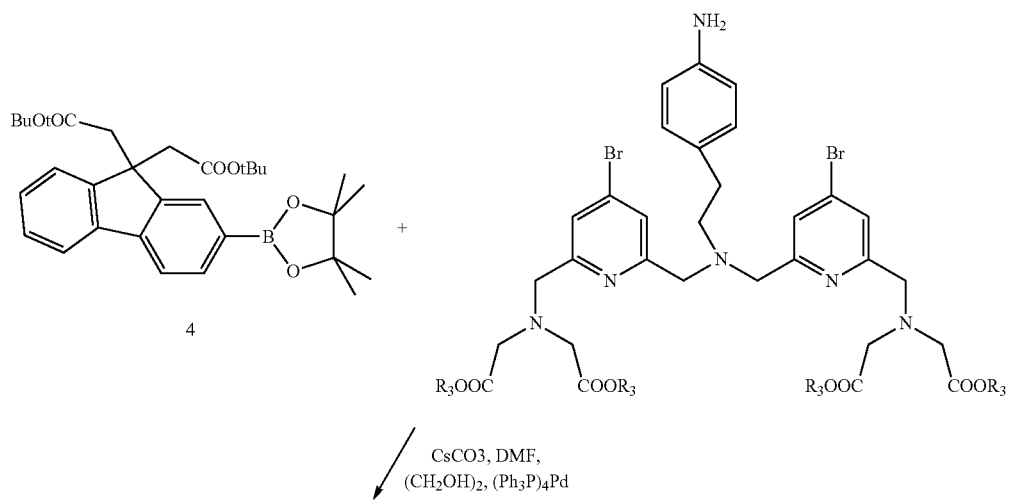

57 58
-continued
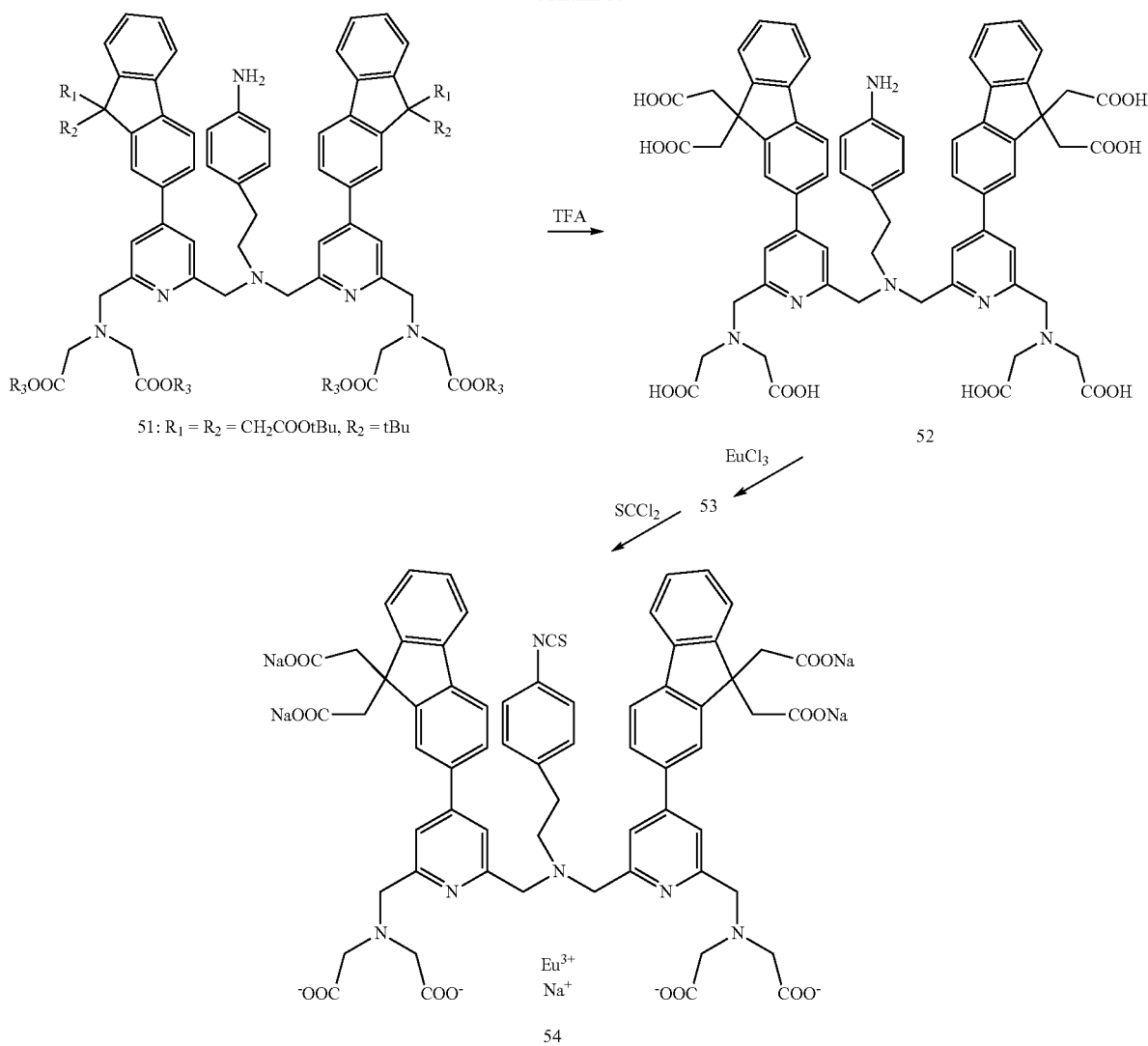
Scheme 12
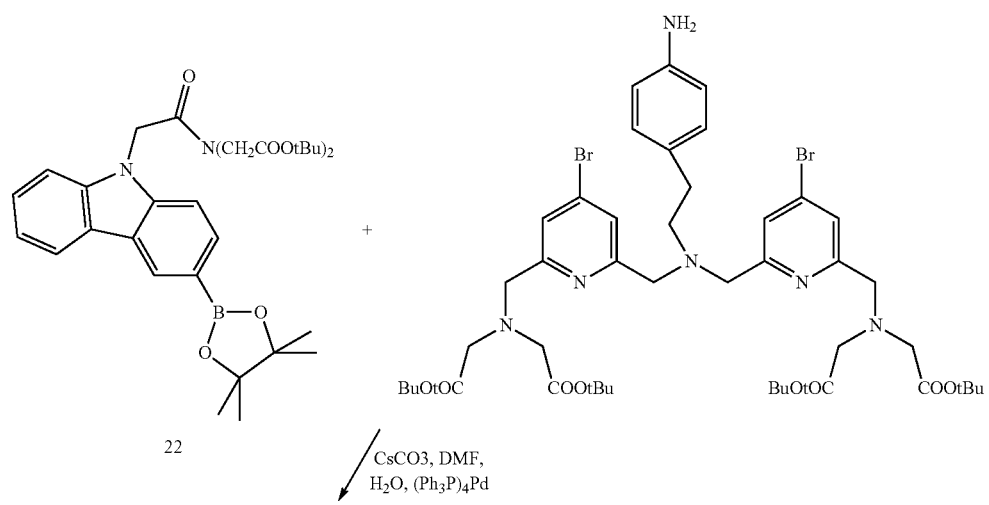

-continued
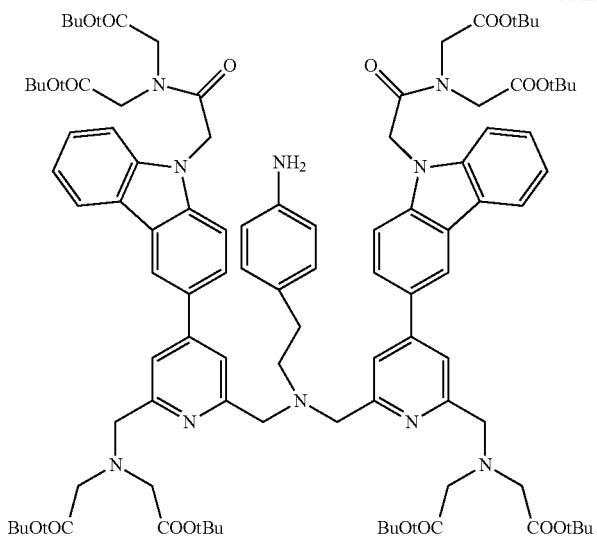
55
TFA →
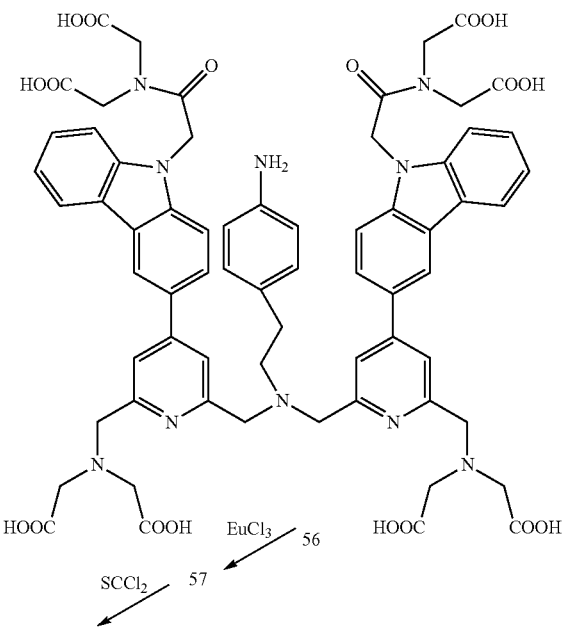
56
EuCl₃
SCCl₂ → 57
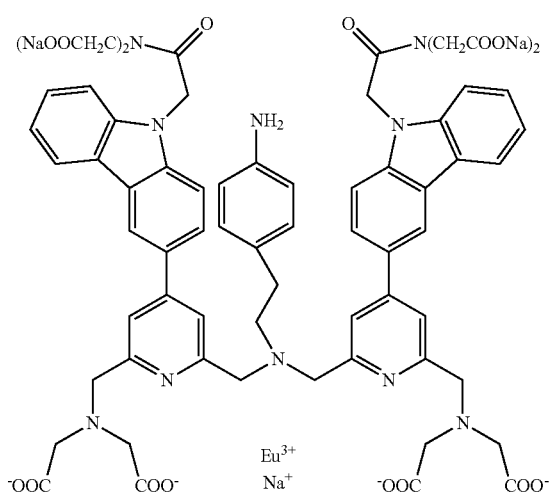
58

Scheme 13
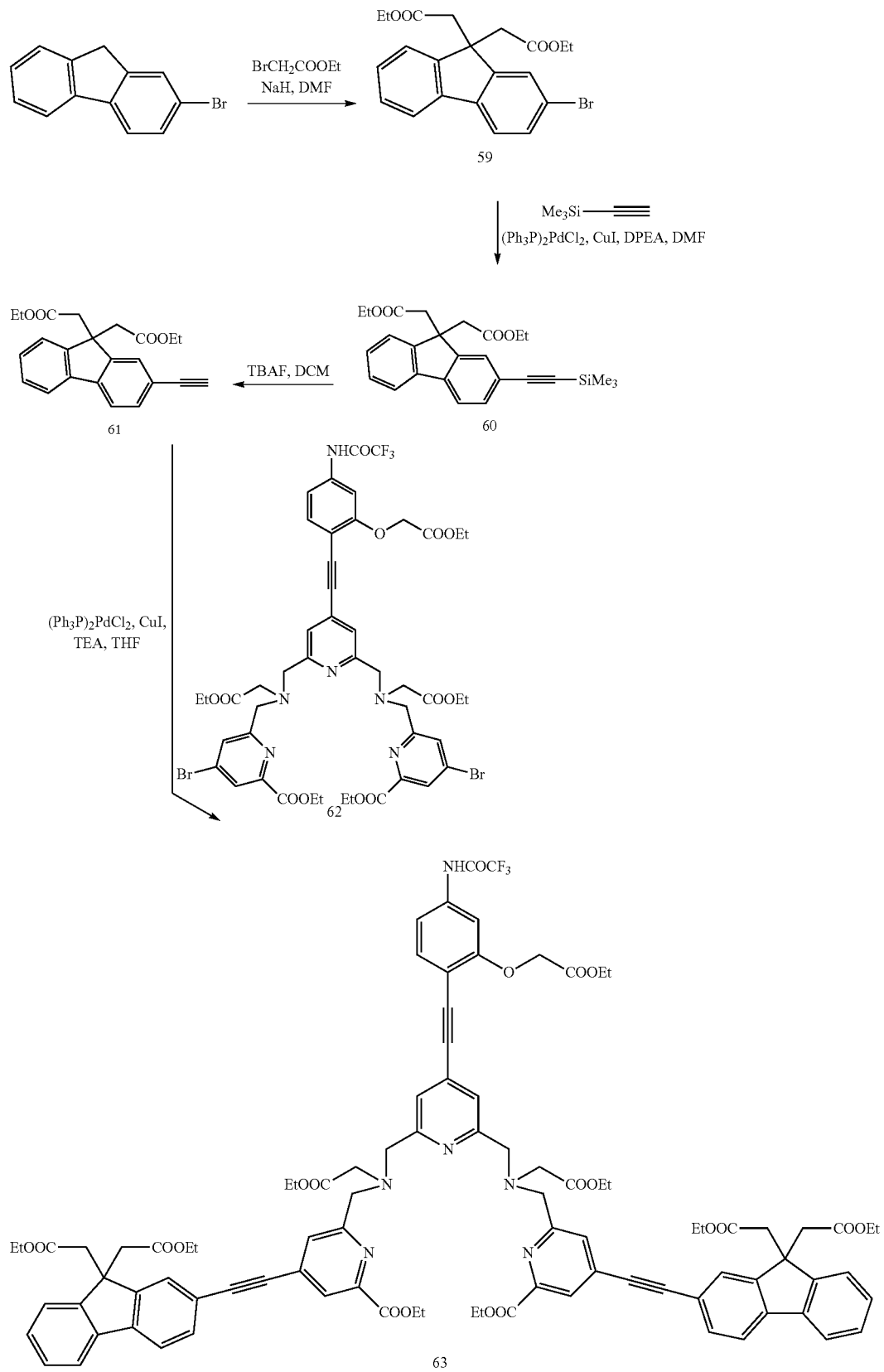

Scheme 14
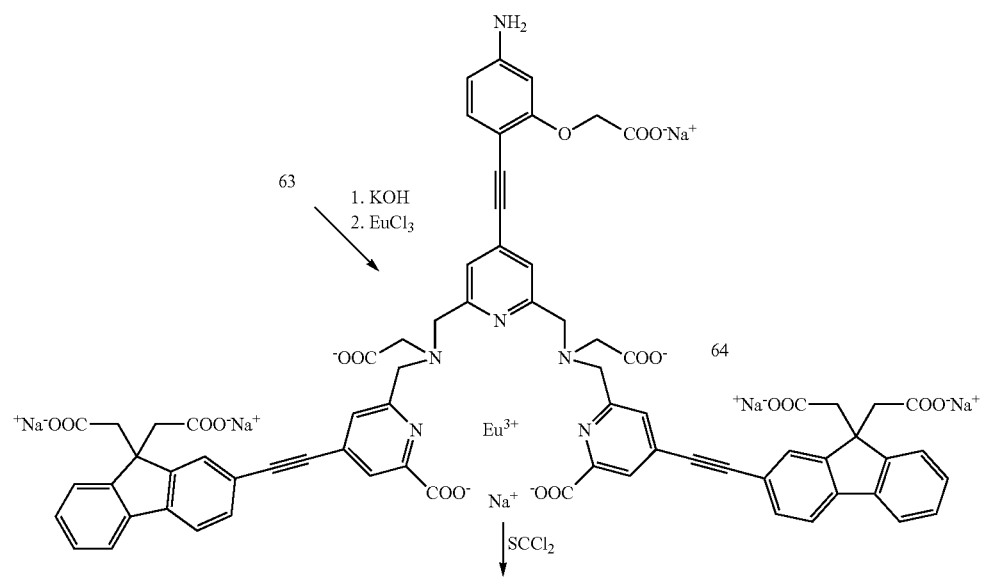
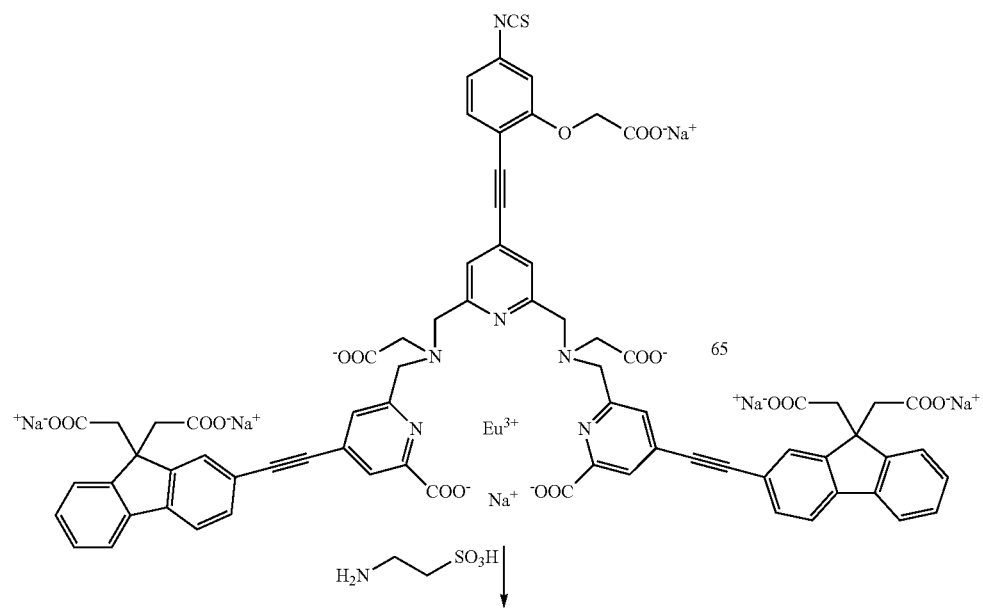

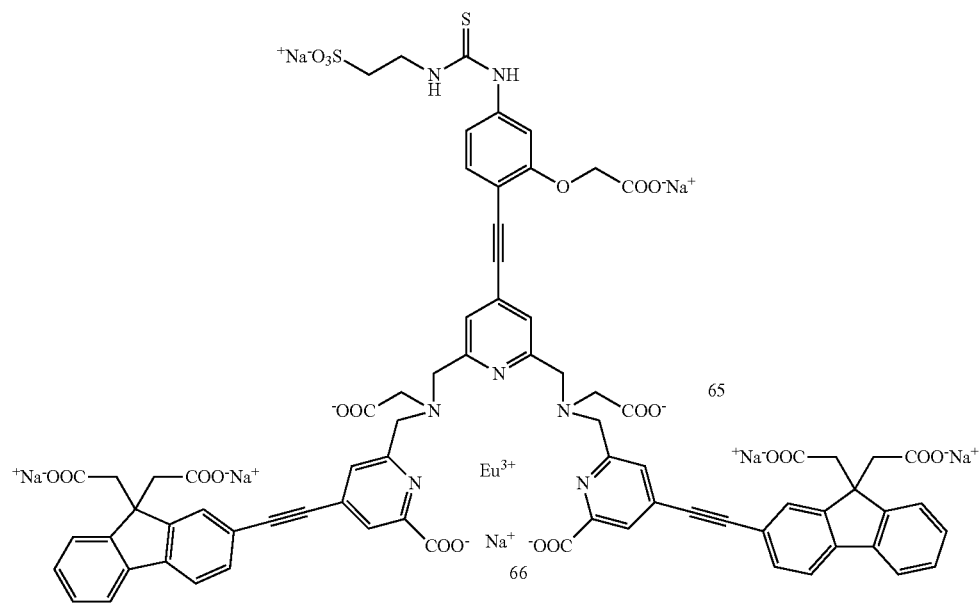
65
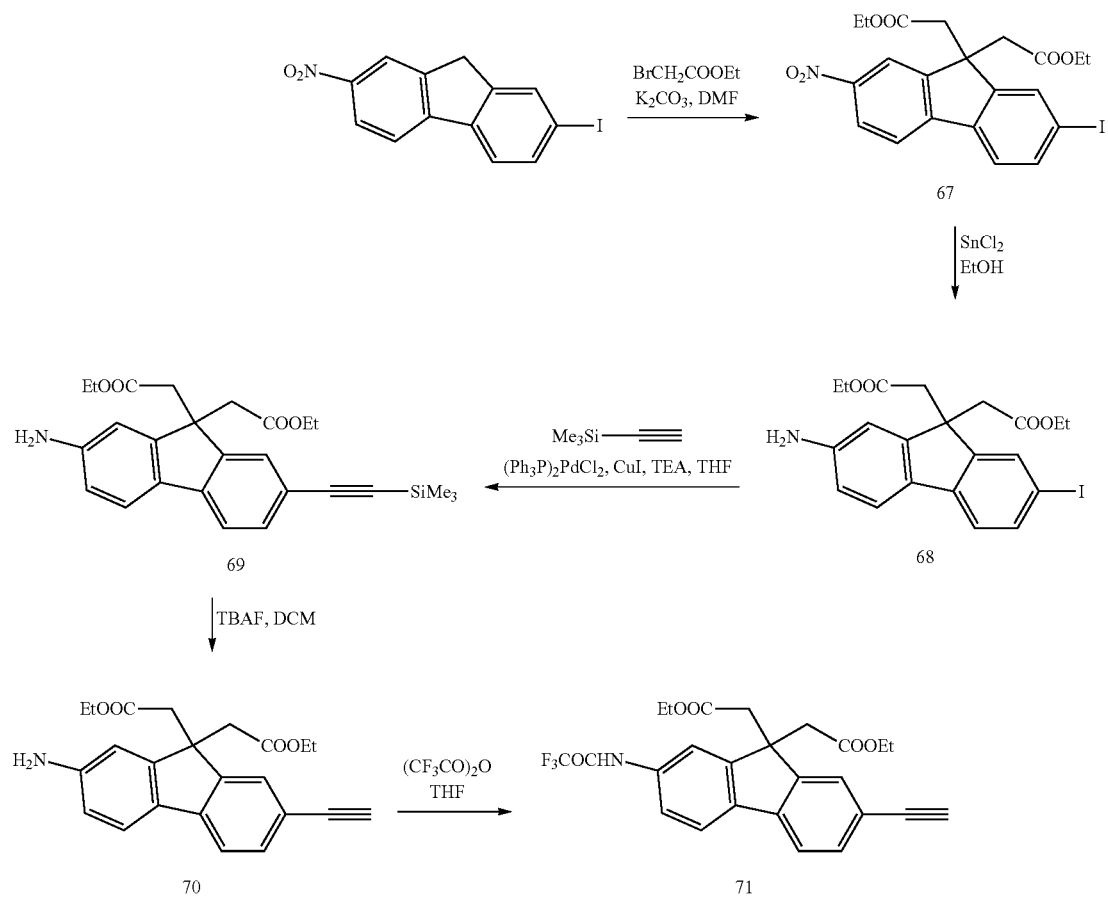
Scheme 15

Scheme 16
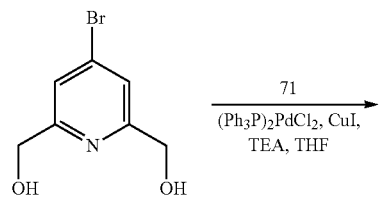
-continued
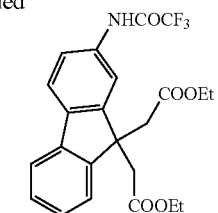
Scheme 17
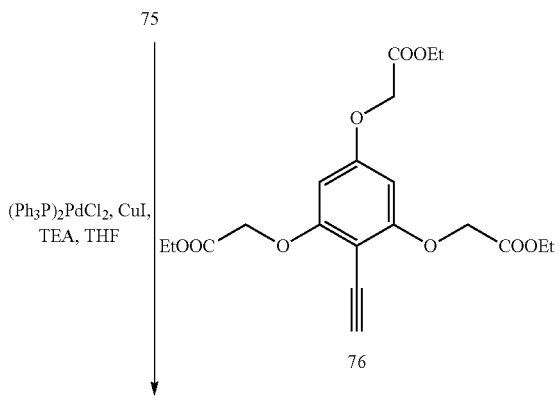

-continued
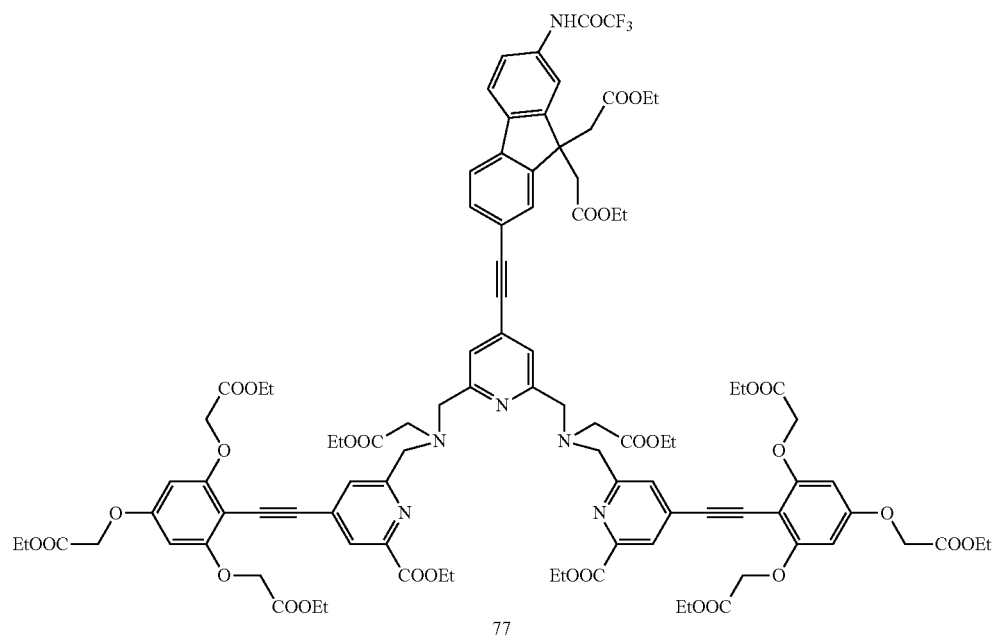
77
Scheme 18
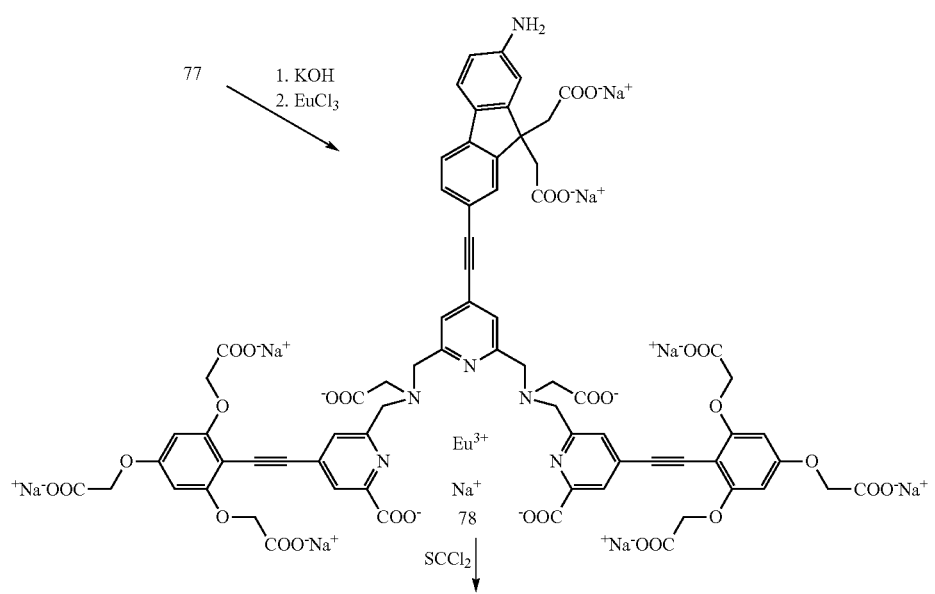

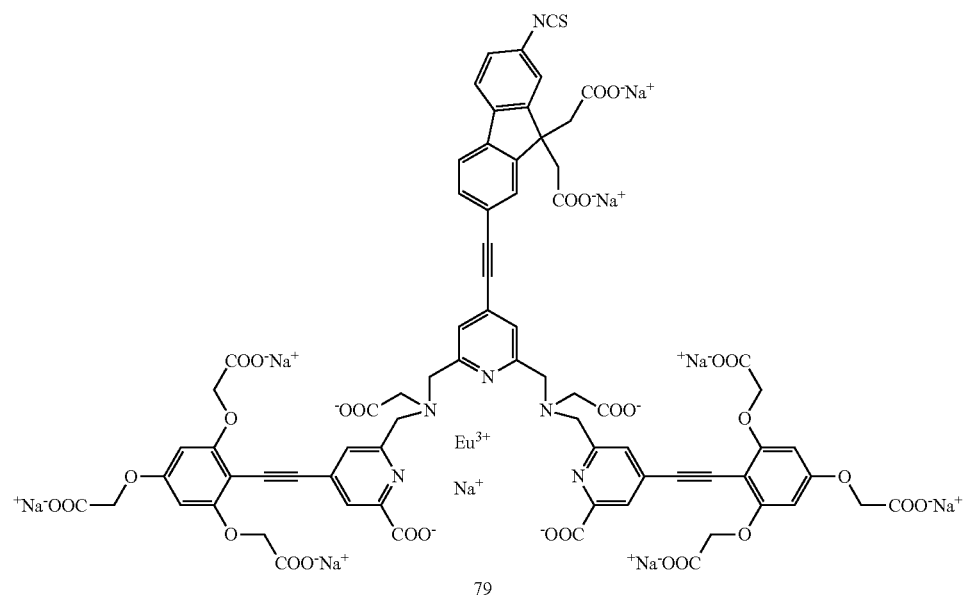
79
Scheme 19
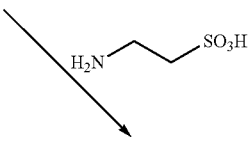
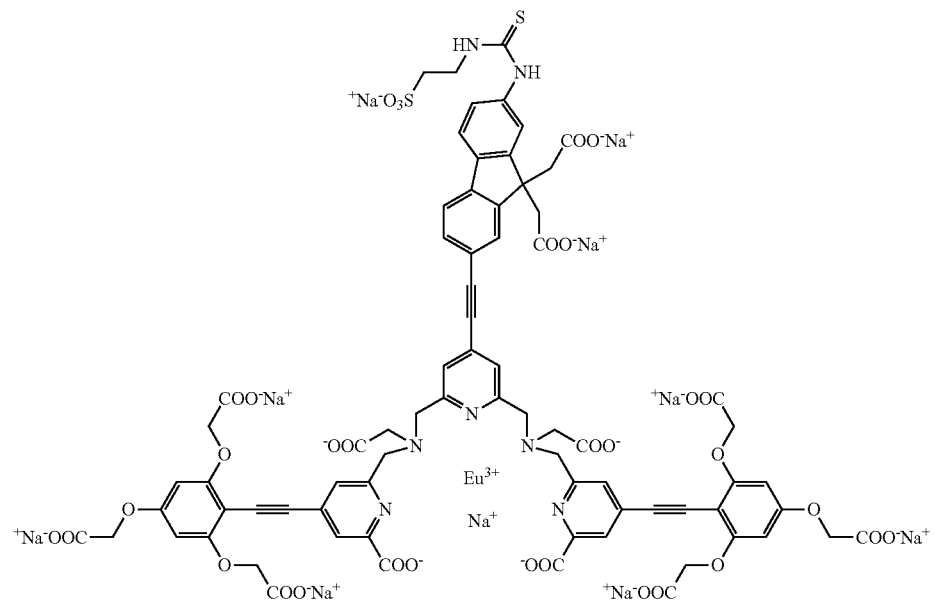
80

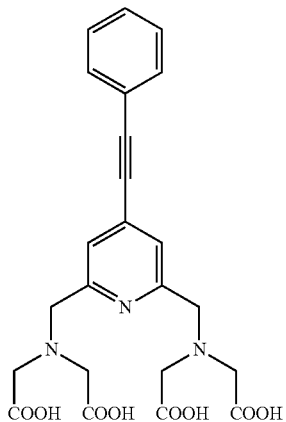 [SMILES: O=C(O)CN(CC(=O)O)Cc1cc(C#Cc2ccccc2)cc(CN(CC(=O)O)CC(=O)O)n1]

The reference ligand used in the Example 59

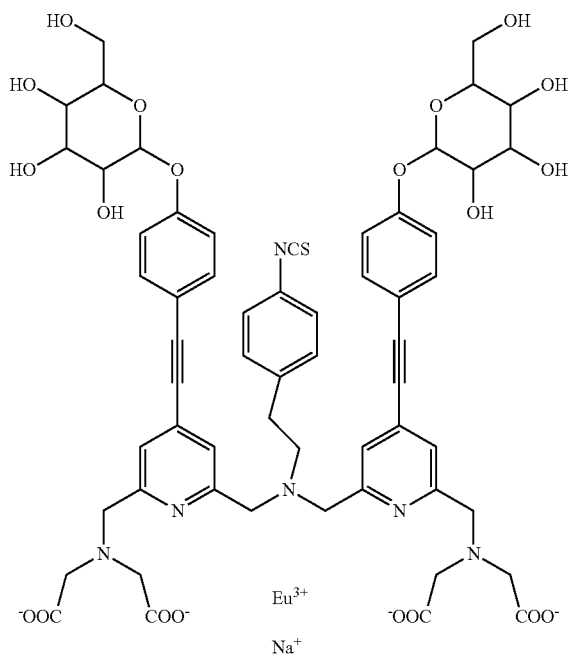

The reference nine dentate label used in the Example 60 and 80.

The invention claimed is:

1. A luminescent lanthanide chelate comprising one or more chromophoric moieties of the formula (I):

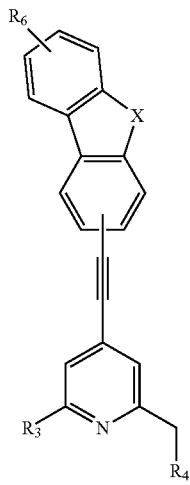

Formula (I)

wherein:
X is selected from the group consisting of —S—, —O—, —NR$_1$—, —CR$_1$R$_2$—, >C=O, and >C=N—O—R$_1$;
R$_1$ and R$_2$ each independently are selected from the group consisting of hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$N$^+$(CH$_3$)$_2$R$_5$, —(CH$_{1-6}$OH, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, and —CO(CH$_2$)$_{1-6}$NCH$_3$R$_5$, wherein R$_5$ is selected from the group consisting of hydrogen, C$_{1-12}$-alkyl, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$N$^+$(CH$_3$)$_2$(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, a hydrophilic group, a reactive group Z, an oligopeptide, a polypeptide and a nucleotide;
R$_3$ and —CH$_2$—R$_4$ each independently are selected from the group consisting of —CH$_2$—N(CH$_2$COOH)$_2$, —CH$_2$—N(CH$_2$COO$^-$)$_2$, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$OH, —(CH$_2$)$_{1-6}$OR$_5$, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$SH, —(CH$_2$)$_{1-6}$SR$_5$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —(CH$_2$)$_{1-3}$O(CH$_2$)$_{1-3}$-Chr, and —(CH$_2$)$_{1-3}$S(CH$_2$)$_{1-3}$-Chr; or R$_3$ and R$_4$ each independently are selected from the group consisting of —COOH, —COO$^-$, —PO$_3$H$_2$, —PO$_3^{2-}$, —P(CH$_3$)O$_2$H, —P(CH$_3$)O$_2^-$, —P(Ph)O$_2$H, —P(Ph)O$_2^-$, —COR$_5$, —CO(CH$_2$)$_{1-6}$NHR$_5$, and —CO(CH$_2$)$_{1-6}$NCH$_3$R$_5$, wherein R$_5$ is selected from the group consisting of —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, and —(CH$_2$)$_{1-6}$PO$_3^{2-}$, a hydrophilic group, a reactive group Z, an oligopeptide, a polypeptide and a nucleotide;

or R$_3$ and —CH$_2$—R$_4$ are independently —(CH$_2$)$_{1-3}$N(R$_8$)—(CH$_2$)$_{1-3}$—Chr, wherein R$_8$ is selected from —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_5$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$NHC(=O)NHR$_5$, —(CH$_2$)$_{1-6}$NHC(=S)NHR$_5$, —(CH$_2$)$_{1-6}$C(=O)R$_5$, —(CH$_2$)$_{1-6}$—C$_6$H$_4$—R$_5$, —COR$_5$, —CO(CH$_2$)$_{1-6}$NHR$_5$, —CO(CH$_2$)$_{1-6}$NCH$_3$R$_5$, —(CH$_2$)$_{1-10}$OH, —(CH$_2$)$_{1-10}$OR$_5$, —(CH$_2$)$_{1-10}$NH$_2$, —(CH$_2$)$_{1-10}$NHR$_5$, —(CH$_2$)$_{1-10}$NCH$_3$R$_5$, —(CH$_2$)$_{1-10}$SH, and —(CH$_2$)$_{1-10}$SR$_5$ wherein R$_5$ is selected from —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, and a reactive group Z, and wherein Chr represents another chromophoric moiety;

R$_6$ is selected from the group consisting of hydrogen —Cl, —Br, —F, —I, —CH$_3$, —(CH$_2$)$_{1-6}$OH, —(CH$_2$)$_{1-6}$OCH$_3$—CF$_3$, —CN, —NO$_2$, —OH, —O(CH$_2$)$_{1-6}$OH, —O(CH$_2$)$_{1-6}$OCH$_2$, —O(CH$_2$)$_{1-6}$COOH, —O(CH$_2$)$_{1-6}$COO$^-$, —SCH$_3$, —S(CH$_2$)$_{1-6}$OH, —S(CH$_2$)$_{1-6}$OCH$_2$, —S(CH$_2$)$_{1-6}$COOH, —S(CH$_2$)$_{1-6}$COO$^-$, —CONH$_2$, —CONHCH$_3$, —CON(CH$_3$)$_2$, —CONH(CH$_2$)$_{1-6}$OH, —CONHCH(CH$_2$OH)$_2$, —CONHC(CH$_2$OH)$_3$, —NHCOCH$_3$, —NHCO(CH$_2$)$_{1-6}$OH, —NHCO(CH$_2$)$_{1-6}$COOH, —NHCO(CH$_2$)$_{1-6}$COO$^-$, a reactive group Z, and a hydrophilic group; wherein the hydrophilic group is selected from the group consisting of monosaccharides, disaccharides, —(CH$_2$)$_{1-6}$CH$_2$OH, —CH(CH$_2$OH)$_2$, —C(CH$_2$OH)$_3$—(CH$_2$)$_{1-3}$—O—(CH$_2$CH$_2$O)$_{0-5}$—H, —(CH$_2$)$_{1-3}$—O—(CH$_2$CH$_2$O)$_{0-5}$—C$_{1-4}$-alkyl, —O—(CH$_2$CH$_2$O)$_{1-6}$—H, and —O—(CH$_2$CH$_2$O)$_{1-6}$—C$_{1-4}$—alkyl, wherein the reactive group Z is selected from the group consisting of azido(—N$_3$), alkynyl (—C≡CH), alkylene (—CH=CH$_2$), amino (—NH$_2$), aminooxy (—O—NH$_2$), carboxyl(—COOH), aldehyde (—CHO), hydrazide (—CONHNH$_2$), mercapto (—SH), maleimido, activated derivatives of maleimido, isocyanato (—NCO), isothiocyanato (—NCS), diazonium (—N$^+$N), bromoacetamido, iodoacetamido, pyridyl-2-dithio, and 6- substituted 4-chloro-1,3,5-triazin-2-ylamino, wherein a spacer is or is not included in a reactive group Z or a hydrophilic group and, when included, comprises one to five moieties, each moiety being independently selected from the group consisting of a phenylene, an alkylene containing 1-10 carbon atoms, an ethylenediyl (—C=C—), an ether (—O—), a thioether (—S—), a disulfide (—S—S—), an amide (—C(=O)—NH—, —NH—C(=O)—, —C(=O)—NCH$_3$— and —NCH$_3$—C(=O)—), a thiourea (—NH—C(=S)—NH—), and a triazole; and Ln$^{3+}$ is a lanthanide ion.

2. The luminescent lanthanide chelate according to claim 1, wherein X is —CR$_1$R$_2$—.

3. The luminescent lanthanide chelate according to claim 1, wherein R$_1$ and R$_2$ each independently are selected from the group consisting of hydrogen, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —CH$_2$CONHCH$_2$COOH, —CH$_2$CONHCH$_2$COO$^-$, —CH$_2$CON(CH$_2$COOH)$_2$, —CH$_2$CON(CH$_2$COO$^-$)$_2$, —COCH$_2$NHCH$_2$COOH, —COCH$_2$NHCH$_2$COO$^-$, —COCH$_2$N(CH$_2$COOH)$_2$, and —COCH$_2$N(CH$_2$COO$^-$)$_2$.

4. The luminescent lanthanide chelate according to claim 1, wherein the luminescent lanthanide chelate is selected from the following formulae

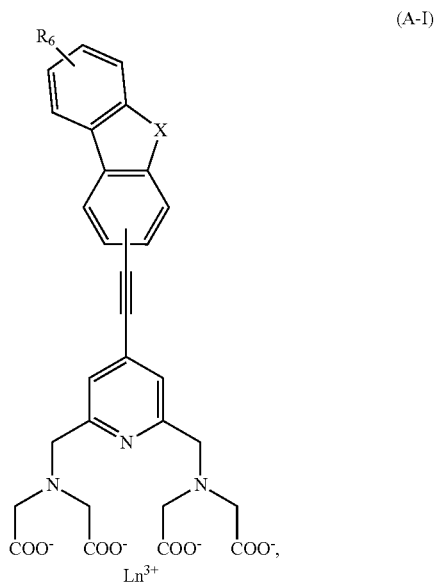

(A-I)

(B-I)
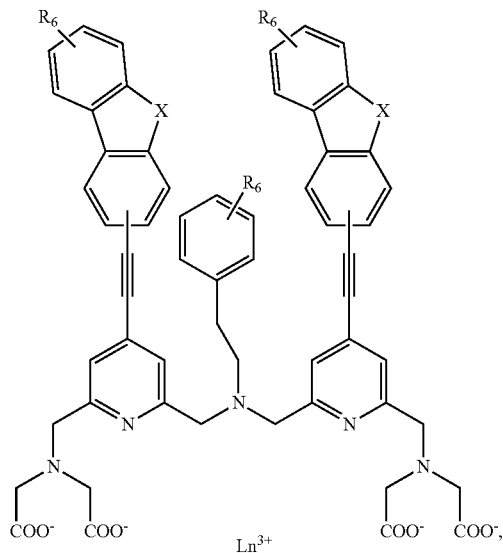
Ln³⁺
(B-I*)
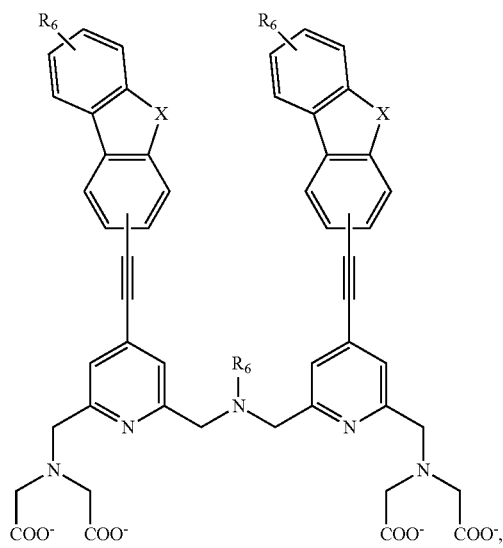

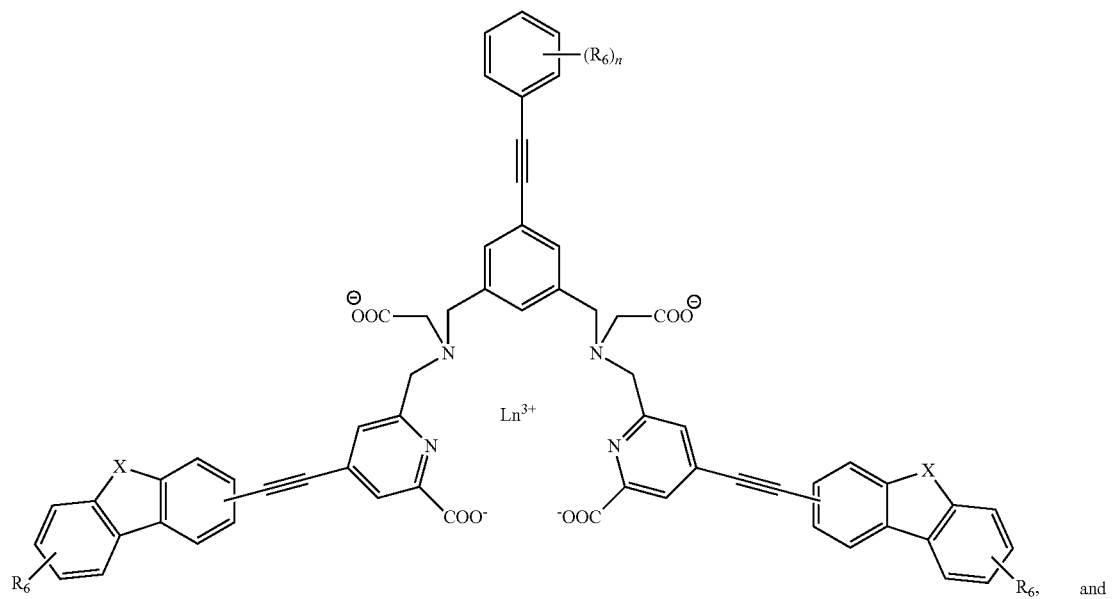
(C-I)
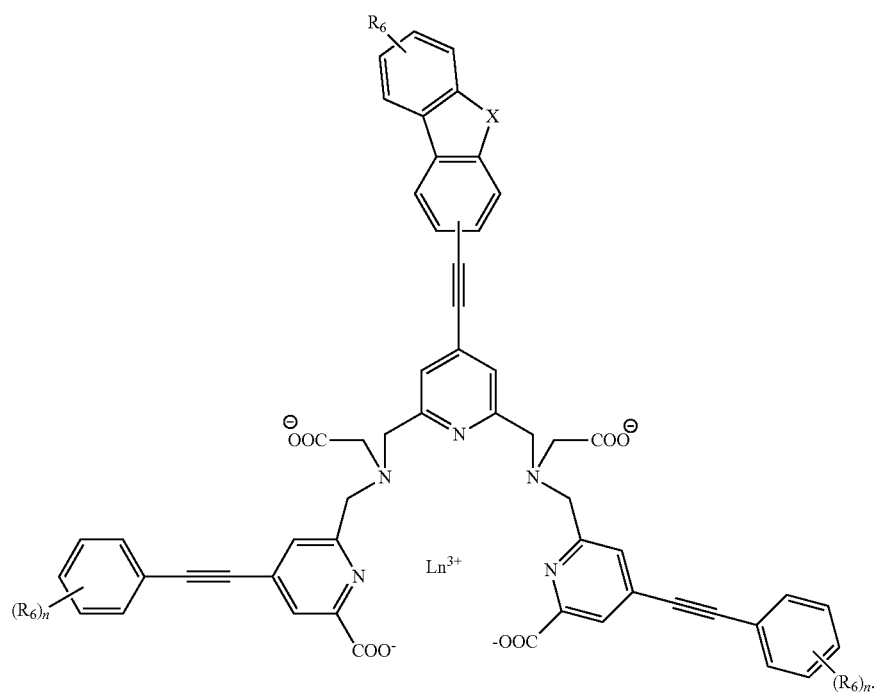
(D-I)
and

5. A lanthanide chelating ligand comprising one or more chromophoric moieties of the formula (II)

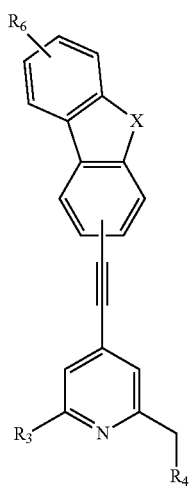

Formula (II)

wherein X is selected from the group consisting of —S—, —O—, —NR$_1$—, —CR$_1$R$_2$—, >C=O, and >C=N—O—R$_1$;

R$_1$ and R$_2$ each independently are selected from the group consisting of hydrogen, —(CH$_{1-6}$COOH, —(CH$_2$)$_{1-6}$COO$^-$, —(CH$_{1-6}$SO$_3$H, —(CH$_2$)$_{1-6}$SO$_3^-$, —(CH$_2$)$_{1-6}$O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_{1-6}$NCH$_3$R$_5$, —(CH$_2$)$_{1-6}$NEtR$_5$, —(CH$_{1-6}$N(R$_5$)$_2$, —(CH$_2$)$_{1-6}$N+(CH$_3$)$_2$R$_5$, —(CH$_{1-6}$OH, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_{1-6}$C(=O)NEtR$_5$, —(CH$_2$)$_{1-6}$C(=O)N(R$_5$)$_2$, —(CH$_{1-6}$NHC(=O)NHR$_5$, —(CH$_2$)$_{1-6}$NHC(=S)NHR$_5$, —(CH$_2$)$_{1-6}$C(=O) R$_5$, —(CH$_2$)$_{1-6}$—C$_6$H$_4$—R$_5$, —COR$_5$, —CO(CH$_{1-6}$NHR$_5$, and —CO(CH$_{1-6}$NCH$_3$R$_5$, wherein R$_5$ is selected from the group consisting of hydrogen, C$_{1-12}$-alkyl, —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$N+(CH$_3$)$_2$(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, a hydrophilic group, a reactive group Z, an oligopeptide, a polypeptide and a nucleotide;

R$_3$ and —CH$_2$—R$_4$ each independently are selected from the group consisting of —CH$_2$—N(CH$_2$COOH)$_2$, —CH$_2$—N(CH$_2$COO$^-$)$_2$, —(CH$_2$)$_{1-6}$COOH, —(CH$_2$)$_{1-6}$ COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$OH, —(CH$_2$)$_{1-6}$OR$_5$, —(CH$_2$CH$_2$O)$_{1-4}$CH$_2$CH$_2$OH, —(CH$_2$CH$_2$O)$_{1-4}$CH$_2$CH$_2$OCH$_3$, —(CH$_2$)$_{1-6}$SH, —(CH$_2$)$_{1-6}$SR$_5$, —(CH$_2$)$_{1-6}$NHC(=O) R$_5$, —(CH$_2$)$_{1-6}$NCH$_3$C(=O) R$_5$, —(CH$_2$)$_{1-6}$C(=O)NHR$_5$, —(CH$_2$)$_{1-6}$C(=O)NCH$_3$R$_5$, —(CH$_2$)$_{1-6}$C(=O)NEtR$_5$, —(CH$_2$)$_{1-6}$C(=O)N(R$_5$)$_2$, —(CH$_2$)$_{1-6}$NHC(=O)NHR$_5$, —(CH$_2$)$_{1-6}$ NHC(=S)NHR$_5$, —(CH$_2$)$_{1-6}$C(=O) R$_5$, —(CH$_2$)$_{1-6}$—C$_6$H$_4$—R$_5$, —(CH$_2$)$_{1-3}$O(CH$_2$)$_{1-3}$-Chr, and —(CH$_2$)$_{1-3}$S(CH$_2$)$_{1-3}$-Chr; or R$_3$ and R$_4$ each independently are selected from the group consisting of —COOH, —COO$^-$, —PO$_3$H$_2$, —PO$_3^{2-}$, —P(CH$_3$)O$_2$H, —(CH$_3$)O$_2^-$, —P(Ph)O$_2$H, —(Ph)O$_2^-$, —COR$_5$, —CO(CH$_2$)$_{1-6}$NHR$_5$, and —CO(CH$_2$)$_{1-6}$NCH$_3$R$_5$, wherein R$_5$ is selected from the group consisting of —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$ PO$_3^{2-}$, a hydrophilic group, a reactive group Z, an oligopeptide, a polypeptide and a nucleotide;

or R$_3$ and —CH$_2$—R$_4$ are independently —(CH$_2$)$_{1-3}$N(R$_8$)—(CH$_2$)$_{1-3}$—Chr, wherein R$_8$ is selected from —(CH$_2$)$_{1-6}$COOH, —(CH$_2$)$_{1-6}$COO$^-$, —(CH$_2$)$_{1-6}$SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$ PO$_3^{2-}$, —(CH$_2$)$_{1-6}$NHR$_5$, —(CH$_2$)$_{1-6}$NCH$_3$R$_5$, —(CH$_2$)$_{1-6}$NEtR$_5$, —(CH$_2$)$_{1-6}$N(R$_5$)$_2$, —(CH$_2$)$_{1-6}$NHC(=O)R$_5$, —(CH$_2$)$_{1-6}$NCH$_3$C(=O)R$_5$, —(CH$_2$)$_{1-6}$C(=O)NHR$_5$, —(CH$_2$)$_{1-6}$C(=O)NCH$_3$R$_5$, —(CH$_2$)$_{1-6}$ NHC(=O)NHR$_5$, —(CH$_2$)$_{1-6}$NHC(=S)NHR$_5$,—(CH$_2$)$_{1-6}$C(=O) R$_5$, —(CH$_2$)$_{1-6}$—C$_6$H$_4$—R$_5$, —COR$_5$, —CO(CH$_2$)$_{1-6}$NHR$_5$, —CO(CH$_2$)$_{1-6}$NCH$_3$R$_5$, —(CH$_2$)$_{1-10}$OH, —CH$_2$)$_{1-10}$OR$_5$, —(CH$_2$)$_{1-10}$NH$_2$, —(CH$_2$)$_{1-10}$NHR$_5$, —(CH$_2$)$_{1-10}$NCH$_3$R$_5$, —(CH$_2$)$_{1-10}$SH, and —(CH$_2$)$_{1-10}$SR$_5$ wherein R$_5$ is selected from —(CH$_2$)$_{1-6}$COOH, —(CH$_2$)$_{1-6}$COO$^-$, —(CH$_2$)$_{1-6}$ SO$_3$H, —(CH$_2$)$_{1-6}$SO$_3^-$, —(CH$_2$)$_{1-6}$—O—PO$_3$H$_2$, —(CH$_2$)$_{1-6}$—O—PO$_3^{2-}$, —(CH$_2$)$_{1-6}$PO$_3$H$_2$, —(CH$_2$)$_{1-6}$ PO$_3^{2-}$, and a reactive group Z, and wherein Chr represents another chromophoric moiety R$_6$ is selected from the group consisting of hydrogen —Cl, —Br, —F, —I, —CH$_3$, —(CH$_2$)$_{1-6}$OH, —(CH$_2$)$_{1-6}$OCH$_3$, —CF$_3$, —CN, —NO$_2$, —OH, —O(CH$_2$)$_{1-6}$OH, —O(CH$_2$)$_{1-6}$OCH$_2$, —O(CH$_2$)$_{1-6}$COOH, —O(CH$_2$)$_{1-6}$COO$^-$, —SCH$_3$, —S(CH$_2$)$_{1-6}$OH, —S(CH$_2$)$_{1-6}$OCH$_2$, —S(CH$_2$)$_{1-6}$COOH, —S(CH$_2$)$_{1-6}$COO$^-$, —CONH$_2$, —CONHCH$_3$, —CON(CH$_3$)$_2$, —CONH(CH$_2$)$_{1-6}$OH, —CONHCH(CH$_2$OH)$_2$, —CONHC(CH$_2$OH)$_3$, —NHCOCH$_3$, —NHCO(CH$_2$)$_{1-6}$OH, —NHCO(CH$_2$)$_{1-6}$COOH, —NHCO(CH$_2$)$_{1-6}$COO$^-$, a reactive group Z, and a hydrophilic group; wherein the hydrophilic group is selected from the group consisting of monosaccharides, disaccharides, —CH$_2$)$_{1-6}$CH$_2$OH, —CH(CH$_2$OH)$_2$, —C(CH$_2$OH)$_3$ —(CH$_2$)$_{1-3}$—O—(CH$_2$CH$_2$O)$_{0-5}$—H, —(CH$_2$)$_{1-3}$—O—(CH$_2$CH$_2$O)$_{0-5}$—C$_{1-4}$-alkyl, —O—(CH$_2$CH$_2$O)$_{1-6}$—H, and —O—(CH$_2$CH$_2$O)$_{1-6}$—C$_{1-4}$-alkyl, wherein the reactive group Z is selected from the group consisting of azido (—N$_3$), alkynyl (—C≡CH), alkylene (—CH=CH$_2$), amino (—NH$_2$), aminooxy (—O—NH$_2$), carboxyl (—COOH), aldehyde (—CHO), hydrazide (—CONHNH$_2$), mercapto (—SH), maleimido, activated derivatives of maleimido, isocyanato (—NCO), isothiocyanato (—NCS), diazonium (—N$^+$N), bromoacetamido, iodoacetamido, pyridyl-2-dithio, and 6-substituted 4-chloro-1,3,5-triazin-2-ylamino, wherein a spacer is or is not included in a reactive group Z or a hydrophilic group and, when included, comprises one to five moieties, each moiety being independently selected from the group consisting of a phenylene, an alkylene containing 1-10 carbon atoms, an ethylenediyl (—C=C—), an ether (—O—), a thioether (—S—), a disulfide (—S—S—), an amide (—C(=O)—NH—, —NH—C(=O)—, —C(=O)—

$NCH_3$— and —$NCH_3$—C(=O)—), a thiourea (—NH—C(=S)—NH—), and a triazole.

6. The luminescent lanthanide chelate according to claim 1, wherein $R_5$ is $C_1$-$C_6$-alkyl.

7. The luminescent lanthanide chelate according to claim 3, wherein $R_1$ and $R_2$ each independently are —$CH_2$—COOH, —$CH_2$—COO$^-$, —$CH_2$CON($CH_2$COOH)$_2$, and —$CH_2$CON($CH_2$COO$^-$)$_2$.

8. The luminescent lanthanide chelate according to claim 1, wherein $R_1$ and $R_2$ are each independently —($CH_2CH_2O$)$_2$ $CH_2CH_2OCH_3$.

9. The luminescent lanthanide chelate according to claim 1, wherein $Ln^{3+}$ is $Eu^{3+}$.

10. The luminescent lanthanide chelate according to claim 1, wherein $R_3$ and —$CH_2$—$R_4$ each independently are selected from the group consisting of —$CH_2$—N($CH_2COOH$)$_2$, —$CH_2N(CH_2COO^-)_2$, and —$(CH_2)_{1-3}$N($R_8$)—$(CH_2)_{1-3}$-Chr, wherein $R_8$ is selected from the group consisting of —$(CH_2)_{1-6}$COOH, —$(CH_2)_{1-6}$COO$^-$, —$(CH_2)_{1-6}$SO$_3$H, —$(CH_2)_{1-6}$SO$_3^-$, —$(CH_2)_{1-6}$—O—PO$_3$H$_2$, —$(CH_2)_{1-6}$—O—PO$_3^{2-}$, —$(CH_2)_{1-6}$PO$_3$H$_2$, —$(CH_2)_{1-6}$PO$_3^{2-}$, and reactive group, or wherein $R_3$ and $R_4$ each independently are selected from the group consisting of —COOH, —COO$^-$, —PO$_3$H$_2$, —PO$_3^{2-}$, —P(CH$_3$)O$_2$H, —P(CH$_3$)O$_2^-$, —P(PH)O$_2$H, and —P(Ph)O$_2^-$.

* * * * *

UNITED STATES PATENT AND TRADEMARK OFFICE
CERTIFICATE OF CORRECTION

PATENT NO. : 10,365,286 B2
APPLICATION NO. : 15/308458
DATED : July 30, 2019
INVENTOR(S) : Harri Takalo Page 1 of 2

It is certified that error appears in the above-identified patent and that said Letters Patent is hereby corrected as shown below:

In the Claims

Claim 1, Column 74, below Formula (I), on Line 20, insert -- $Ln^{3+}$ --.

Claim 1, Column 74, Line 32, "-$(CH_{1-6}OH$," should read -- -$(CH_2)_{1-6}OH$, --.

Claim 1, Column 75, Line 16, "-$(CH_2)_{1-6}N(R_5)_5$," should read -- -$(CH_2)_{1-6}N(R_5)_2$, --.

Claim 4, Columns 79-80, in Formula (C-I) and Formula (D-I), "$\ominus OOC$" should read -- $^-OOC$ --.

Claim 4, Columns 79-80, in Formula (C-I) and Formula (D-I), "$COO\ominus$" should read -- $COO^-$ --.

Claim 5, Column 81, Line 30, "-$(CH_{1-6}COOH$," should read -- -$(CH_2)_{1-6}COOH$, --.

Claim 5, Column 81, Line 31, "-$(CH_{1-6}SO_3H$," should read -- -$(CH_2)_{1-6}SO_3H$, --.

Claim 5, Column 81, Lines 33-34, "-$(CH_{1-6}NCH_3R_5$," should read -- -$(CH_2)_{1-6}NCH_3R_5$, --.

Claim 5, Column 81, Line 34, "-$(CH_{1-6}N(R_5)_2$," should read -- -$(CH_2)_{1-6}N(R_5)_2$, --.

Claim 5, Column 81, Line 35, "-$(CH_{1-6}OH$," should read -- -$(CH_2)_{1-6}OH$, --.

Claim 5, Column 81, Line 39, "-$(CH_{1-6}C(=O)NEtR_5$," should read -- -$(CH_2)_{1-6}C(=O)NEtR_5$, --.

Claim 5, Column 81, Line 40, "-$(CH_{1-6}NHC(=O)NHR_5$," should read -- -$(CH_2)_{1-6}NHC(=O)NHR_5$, --.

Claim 5, Column 81, Lines 42-43, "-$CO(CH_{1-6}NHR_5$, and -$CO(CH_{1-6}NCH_3R_5$," should read -- -$CO(CH_2)_{1-6}NHR_5$, and -$CO(CH_2)_{1-6}NCH_3R_5$, --.

Signed and Sealed this
Twenty-second Day of October, 2019

Andrei Iancu
*Director of the United States Patent and Trademark Office*

CERTIFICATE OF CORRECTION (continued)
U.S. Pat. No. 10,365,286 B2

Claim 5, Column 82, Line 2, "-(Ph)$O_2^-$," should read -- -P(Ph)$O_2^-$, --.

Claim 10, Column 83, Line 19, "-$CH_2$N($CH_2COO^-$)$_2$," should read -- -$CH_2$-N($CH_2COO^-$)$_2$, --.

Claim 10, Column 83, Line 27, "-P(PH)$O_2$H," should read -- -P(Ph)$O_2$H, --.